US009975932B2

United States Patent
Wald et al.

(10) Patent No.: US 9,975,932 B2
(45) Date of Patent: May 22, 2018

(54) VARIANTS OF GROUP 5 ALLERGENS OF THE TRUE GRASSES HAVING REDUCED ALLERGENEITY DUE TO MUTAGENESIS OF PROLINE RESIDUES

(75) Inventors: Martin Wald, Hamburg (DE); Andreas Nandy, Hamburg (DE); Helmut Fiebig, Schwarzenbek (DE); Bernhard Weber, Hamburg (DE); Helga Kahlert, Hamburg (DE); Gerald Reese, Langen (DE); Oliver Cromwell, Suesel-Fassenberg (DE)

(73) Assignee: Merck Patent GmbH, Darmstadt (DE)

( * ) Notice: Subject to any disclaimer, the term of this patent is extended or adjusted under 35 U.S.C. 154(b) by 1103 days.

(21) Appl. No.: 13/522,093

(22) PCT Filed: Dec. 17, 2010

(86) PCT No.: PCT/EP2010/007746
§ 371 (c)(1),
(2), (4) Date: Jul. 13, 2012

(87) PCT Pub. No.: WO2011/085783
PCT Pub. Date: Jul. 21, 2011

(65) Prior Publication Data
US 2015/0140024 A1    May 21, 2015

(30) Foreign Application Priority Data
Jan. 14, 2010    (EP) ..................... 10000296

(51) Int. Cl.
| A61K 36/00 | (2006.01) |
| A61K 39/00 | (2006.01) |
| A61K 39/35 | (2006.01) |
| A61K 39/36 | (2006.01) |
| C07K 1/00 | (2006.01) |
| C07K 14/00 | (2006.01) |
| C07K 14/37 | (2006.01) |
| C07K 16/00 | (2006.01) |
| C07K 17/00 | (2006.01) |
| C07K 14/415 | (2006.01) |
| A61K 38/00 | (2006.01) |

(52) U.S. Cl.
CPC ............ C07K 14/415 (2013.01); A61K 39/36 (2013.01); A61K 38/00 (2013.01); A61K 39/00 (2013.01)

(58) Field of Classification Search
None
See application file for complete search history.

(56) References Cited

U.S. PATENT DOCUMENTS

| 6,919,086 B1 | 7/2005 | Kahlert et al. |
| 7,214,786 B2 * | 5/2007 | Kovalic ............... C07K 14/415 |
| | | 530/324 |
| 7,265,208 B2 * | 9/2007 | Saxon .................. C07K 16/00 |
| | | 530/387.1 |
| 7,879,334 B1 * | 2/2011 | Saxon .................. C07K 16/00 |
| | | 424/134.1 |
| 2003/0175312 A1 * | 9/2003 | Holm ................... C07K 14/415 |
| | | 424/275.1 |
| 2007/0044171 A1 | 2/2007 | Kovalic et al. |
| 2010/0158955 A1 | 6/2010 | Wald et al. |

FOREIGN PATENT DOCUMENTS

| GB | 2 455 108 | 6/2009 |
| WO | WO-98 43657 | 10/1998 |
| WO | WO-99 34826 | 7/1999 |
| WO | WO-02 40676 | 5/2002 |
| WO | WO-2004 108758 | 12/2004 |
| WO | 2006/138435 A2 | 12/2006 |
| WO | WO-2009 022155 | 2/2009 |
| WO | 2010-018378 A2 | 2/2010 |

OTHER PUBLICATIONS

Gangl et al.'Marker allergens and panallergens in tree and grass pollen allergy.' Allergo J. Int. 24:158-169, 2015.*
Andersson, K. et al., "Characteristics and Immunobiology of Grass Pollen Allergens," Int Arch Allergy Immunol, 2003, vol. 130, pp. 87-107.
Gehlhar, K. et al., "Investigation of different recombinant isoforms of grass group-V allergens (timothy grass pollen) isolated by low-stringency cDNA hybridization—Antibody binding capacity and allergenic activity," Eur. J. Biochem, 1997, vol. 247, pp. 217-233.
International Search Report for PCT/EP2010/007746 dated Apr. 26, 2011.
Multiple sequence alignment with GSP:AAY25618 as disclosed in WO-99 34826, Jul. 15, 1999, XP002632047.
Multiple sequence alignment with GSP:AAY25630 as disclosed in WO-99 34826, Jul. 15, 1999, XP002632094.
Multiple sequence alignment with GSP:AW128248 as disclosed in WO-2009 022155, Feb. 19, 2009, XP002632046.
Multiple sequence alignment with GSP:AWW38484 as disclosed in GB-2455108, Jun. 3, 2009, XP002632045.
Multiple sequence alignment with GSP:AWW38535 as disclosed in GB-2455108, Jun. 3, 2009, XP002632048.
Vrtala, S. et al., "cDNA Cloning of a Major Allergen from Timothy Grass (OPhleum pretense) Pollen; Characterization of the Recombinant Phl p V Allergen[1]," The Journal of Immunology, Nov. 1, 1993, vol. 151, No. 9, pp. 4773-4781.
Wald, M. et al., "Generation of a low Immunoglobulin E-binding mutant of the timothy grass pollen major allergen Phl p 5a," Clinical and Experimental Allergy, 2007, vol. 37, pp. 441-450.

(Continued)

Primary Examiner — Nora Rooney
(74) Attorney, Agent, or Firm — Millen White Zelano & Branigan, P.C.

(57) ABSTRACT

The present invention relates to the preparation and use of recombinant variants of group 5 allergens of the Poaceae (true grasses), which are characterized by reduced IgE reactivity compared with known wild-type allergens and at the same time substantially retained reactivity with T-lymphocytes.

4 Claims, 22 Drawing Sheets

(56) References Cited

OTHER PUBLICATIONS

Robert E. Esch, "Grass Pollen Allergens," in Allergens and Allergen Immunotherapy, Third Edition, CRC Press, pp. 133-150, Oct. 3, 2004.
Heimo Breiteneder and Martin D. Chapman, "Allergen Nomenclature," in Allergens and Allergen Immunotherapy, Third Edition, CRC Press, pp. 37-49, Oct. 3, 2004.
PTO Form 892 from co-pending related U.S. Appl. No. 15/700,430 dated Oct. 4, 2017.
Kuby Immunology, 4th Edition, Chapter 18, "Vaccines," pp. 449-465 (2001).
Kurucz etal. 'Current Animal Models of Bronchial Asthma.' Curr. Pharm. Des. 12:3175-3194, 2006.
Mukherjee et al. 'Allergic Asthma: Influence of Genetic and Environmental Factors.' J. Bioi. Chem. 286(38):32883-32889, 2011.
Hartl et al. 'DNA vaccines for allergy treatment.' Methods 32:328-339, 2004.

\* cited by examiner

Fig. 1a: Alignment of deduced amino acid sequences of group 5 allergens of the Poaceae

Fig. 1b: Preservation of the proline residues

| Phleum pratense (Timothy grass) | | | | Amino acid position | | | | | | | | | |
|---|---|---|---|---|---|---|---|---|---|---|---|---|---|
| Allergen name | IUIS sequence | UniprotKB | Reference | 57 | 58 | 85 | 117 | 146 | 155 | 180 | 211 | 229 | 256 |
| Phl p 5a | | | | | | | | | | | | | |
| Phl p 5.0101 | Phl p 5.0101 | Q40960 | Vrtala 1993, J Immun. 151, 4773-4781 | - | x | x | x | x | x | x | x | x | x |
| Phl p 5.0102 | Phl p 5.0102 | Q40962 | Bufe 1994, JACI 94, 2, 173-181, Gelhar 1997, Eu J Biochem 247, 217-223 | - | x | x | x | x | x | x | x | x | x |
| Phl p 5.0103 | Phl p 5.0103 | O81341 | Gelhar 1997, Eu J Biochem 247, 217-223 | x | x | x | x | x | x | x | x | x | x |
| Phl p 5.0104 | Phl p 5.0104 | P93467 | Gelhar 1997, Eu J Biochem 247, 217-223 | x | x | x | x | x | x | - | x | x | x |
| Phl p 5.0105 | Phl p 5.0105 | O65318 | Wissenbach 1998 | x | x | x | x | x | x | x | x | x | x |
| Phl p 5.0106 | Phl p 5.0106 | O65319 | Wissenbach 1998 | x | x | x | x | x | x | x | x | x | x |
| Phl p 5.0107 | Phl p 5.0107 | O65320 | Wissenbach 1998 | x | x | x | x | x | x | x | x | x | x |
| Phl p 5.0108 | Phl p 5.0108 | O65321 | Wissenbach 1998 | x | x | x | x | x | x | x | x | x | x |
| Phl p 5.0109 | Phl p 5.0109 | Q84U82 | Wald 2007, Clin Ex All 37, 441-450 | x | x | x | x | x | x | x | x | x | x |
| Phl p 5b | | | | | | | | | | | | | |
| Phl p 5.0201 | Phl p 5.0201 | Q40963 | Bufe 1995, FEBS Let 363, 6-12, Gelhar 1997, Eu J Biochem 247, 217-223 | x | | | x | x | x | x | x | x | x |
| Phl p 5.0202 | Phl p 5.0202 | P93466 | Gelhar 1997, Eu J Biochem 247, 217-223 | x | | | x | x | x | x | x | x | x |
| Phl p 5.0203 | Phl p 5.0203 | O81342 | Gelhar 1997, Eu J Biochem 247, 217-223 | x | | | x | x | x | x | x | x | x |
| Phl p 5.0204 | Phl p 5.0204 | N.A. | Gelhar 1997, Eu J Biochem 247, 217-223 | x | | | x | x | x | x | x | x | x |
| Phl p 5.0205 | Phl p 5.0205 | N.A. | Gelhar 1997, Eu J Biochem 247, 217-223 | x | | | x | x | x | x | x | x | x |
| Phl p 5.0206 | Phl p 5.0206 | O81343 | Gelhar 1997, Eu J Biochem 247, 217-223 | x | | | x | x | x | x | x | x | x |
| Phl p 5.0207 | Phl p 5.0207 | O81344 | Gelhar 1997, Eu J Biochem 247, 217-223 | x | | | x | x | x | x | x | x | x |
| Phl p 6 | | | | | | | | | | | | | |
| Phl p 6.0101 | Phl p 6.0101 | P43215 | Petersen (1995) IAAI 108:55-59 | x | x | | x | x | | | | | |
| Phl p 6.0102 | Phl p 6.0102 | O65868 | Vrtala (1999) J Imm 163:5489-5496 | x | x | | x | x | | | | | |
| Lolium perenne (Rye grass) | | | | | | | | | | | | | |
| Lol p 5.0101 | Lol p 5.0101 | Q40237 | Ong 1993, Gene 134(2):235-240 | x | x | | x | x | x | x | x | x | x |
| Lol p 5 C | N.A. | Q9SCI9 | Suphioglu 1999, FEBS Lett 462(3):435-441 | x | x | | x | x | x | x | x | x | x |
| Lol p 5A (clone 12R) | N.A. | Q9XF24 | Ong 1993, Gene 134(2):235-240 | x | x | | x | x | x | x | x | x | x |
| Dactylis glomerata (Orchard grass) | | | | | | | | | | | | | |
| Dac g 5 | N.A. | Q93X60 | van Oort 2001, IAAI 126:196-205 | x | x | | x | x | x | x | x | x | x |
| Dac g 5 | N.A. | Q93X09 | van Oort 2001, IAAI 126:196-205 | x | x | | x | x | x | x | x | x | x |
| Holcus lanatus (Velvet grass) | | | | | | | | | | | | | |
| Hol l 5.0101 | Hol l 5.0101 | O23972 | Schramm (1998), Eur J Biochem 252(2), 200-206 | x | x | | x | x | x | x | x | x | x |
| Hol l 5.0201 | Hol l 5.0201 | O23971 | Schramm (1998), Eur J Biochem 252(2), 200-206 | x | x | | x | x | x | x | x | x | x |
| Hol l 5b | N.A. | O9FPO6 | Sturaro&Viotti 2000, Milano, Italy | x | x | | x | x | x | x | x | x | x |
| Poa pratensis (Kentucky blue grass) | | | | | | | | | | | | | |
| Poa p 5.0101 | Poa p 5.0101 | Q8RVS9 | Sturaro&Viotti 2000, Milano, Italy | x | x | | x | x | x | x | x | x | x |
| Poa p 5 (Poa p 9/KBG31) | N.A. | P22284 | Silvanovich 1991, JBC 266(2): 1204-1210 | x | - | x | x | x | x | x | x | x | x |
| Poa p 5 (Poa p 9/KBG41) | N.A. | P22285 | Silvanovich 1991, JBC 266(2): 1204-1210 | x | - | x | x | x | x | x | x | x | x |
| Poa p 5 (Poa p 9/KBG60) | N.A. | P22286 | Silvanovich 1991, JBC 266(2): 1204-1210 | x | - | x | x | x | x | x | x | x | x |
| Phalaris aquatica (Canary grass) | | | | | | | | | | | | | |
| Pha a 5.0101 | Pha a 5.0101 | P56184 | Suphioglu & Singh 1995, Clin Exp All 25: 853-865 | x | x | | x | x | x | x | x | x | x |
| Hordeum vulgare (Barley) | | | | | | | | | | | | | |
| Hor v 5.0101 | Hor v 5.0101 | Q04828 | Astwood&Hill (1996), Gene 182: 53-62 | ? | ? | ? | x | x | x | x | x | x | x |
| Triticum aestivum (Wheat) | | | | | | | | | | | | | |
| Tri a 5 | N.A. | Q7XJP9 | Ciaffi 2005, Gene 346:221-230 | x | x | | x | x | x | x | x | x | |

Fig. 2: Working model of the position of the proline residues in the 3D structure of Phl p 5a
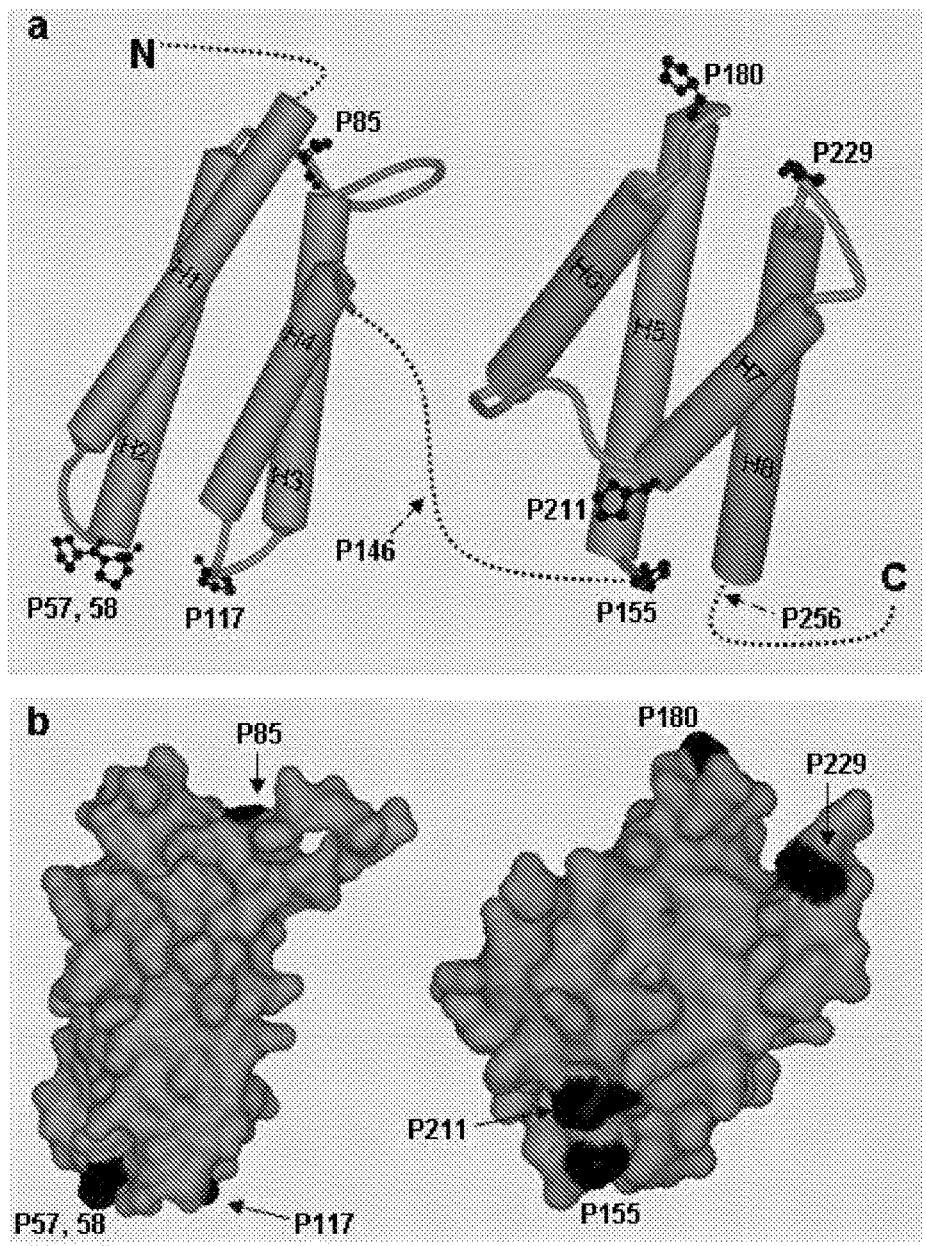

Fig. 3: rPhl p 5a wt (IUIS entry Phl p 5.0109); cDNA sequence (GenBank entry: AJ555152; 855 bp), SEQ ID NO:1

GCCGATCTAGGCTACGGCCCGGCCACCCCAGCTGCCCCGGCCGCCGGCTACACCCCC
GCCGCCCCGGCCGGAGCGGAGCCAGCAGGTAAGGCGACGACCGAGGAGCAGAAGCTG
ATCGAGAAGATCAACGCCGGCTTCAAGGCGGCCTTGGCCGCTGCCGCCGGCGTCCCGC
CAGCGGACAAGTACAGGACGTTCGTCGCAACCTTCGGCGCGGCCTCCAACAAGGCCTT
CGCGGAGGGCCTCTCGGGCGAGCCCAAGGGCGCCGCCGAATCCAGCTCCAAGGCCGC
GCTCACCTCCAAGCTCGACGCCGCCTACAAGCTCGCCTACAAGACAGCCGAGGGCGCG
ACGCCTGAGGCCAAGTACGACGCCTACGTCGCCACCCTAAGCGAGGCGCTCCGCATCA
TCGCCGGCACCCTCGAGGTCCACGCCGTCAAGCCCGCGGCCGAGGAGGTCAAGGTTAT
CCCTGCCGGCGAGCTGCAGGTCATCGAGAAGGTCGACGCCGCCTTCAAGGTCGCTGCC
ACCGCCGCCAACGCCGCGCCCGCCAACGACAAGTTCACCGTCTTCGAGGCCGCCTTCA
ACAACGCCATCAAGGCGAGCACGGGCGGCGCCTACGAGAGCTACAAGTTCATCCCCGC
CCTGGAGGCCGCCGTCAAGCAGGCCTACGCCGCCACCGTCGCCACCGCGCCGGAGGT
CAAGTACACCGTCTTTGAGACCGCGCTGAAAAAGGCCATCACCGCCATGTCCGAGGCCC
AGAAGGCTGCCAAGCCCGCTGCCGCTGCCACCGCCACCGCAACCTCCGCCGTTGGCGC
GGCCACCGGCGCCGCCACCGCCGCTACTGGTGGCTACAAAGTCTGA

Fig. 4: rPhl p 5a wt (IUIS entry Phl p 5.0109); deduced amino acid sequence (UniProtKB entry: Q84UI2; 284 aa), SEQ ID NO:2

ADLGYGPATPAAPAAGYTPAAPAGAEPAGKATTEEQKLIEKINAGFKAALAAAAGVPPADKYR
TFVATFGAASNKAFAEGLSGEPKGAAESSSKAALTSKLDAAYKLAYKTAEGATPEAKYDAYV
ATLSEALRIIAGTLEVHAVKPAAEEVKVIPAGELQVIEKVDAAFKVAATAANAAPANDKFTVFEA
AFNNAIKASTGGAYESYKFIPALEAAVKQAYAATVATAPEVKYTVFETALKKAITAMSEAQKAA
KPAAAATATATSAVGAATGAATAATGGYKV

Fig. 5: N-terminal histidine fusion component; DNA sequence (57 bp), SEQ ID NO:3

ATGGCCCTTCACCACCATCACCACCACGATATCCCGGAAAACCTGTACTTCCAGGGT

Fig. 6: N-terminal histidine fusion component; amino acid sequence (19 aa) SEQ ID:4

MALHHHHHHDIPENLYFQG

Fig. 7: Results of the IgE inhibition tests with Phl p 5a variants with proline deletions in individual loops on use of a serum pool

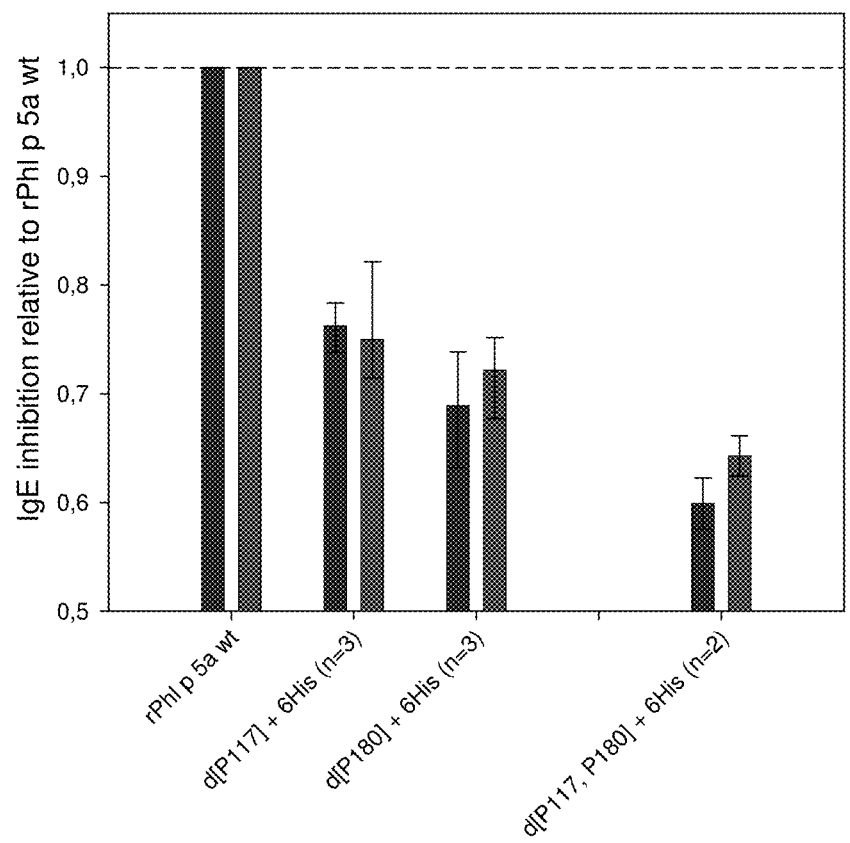
Fig. 8: Comparison of the IgE inhibition of rPhl p 5a d[P117, 180] + 6His with the single-position proline mutants rPhl p 5a d[P117] + 6His and d[P180] + 6His Fig. 9: Comparison of the IgE inhibition of MPV.3 + 6His with the single-position proline mutants rPhl p 5a d[P57, 58] + 6His and d[P229] + 6His Fig. 10: Comparison of the IgE inhibition of MPV.3 + 6His with the single-position proline mutants rPhl p 5a d[P211] + 6His, P211L + 6His, K61E + 6His and E205K + 6His Fig. 11: Test for functional allergeneity of MPV.3 + 6His Fig. 12: IgE inhibition test with MPV.4 + 6His and MPV.4

Fig. 13: Determination of the molecular weight of MPV.5
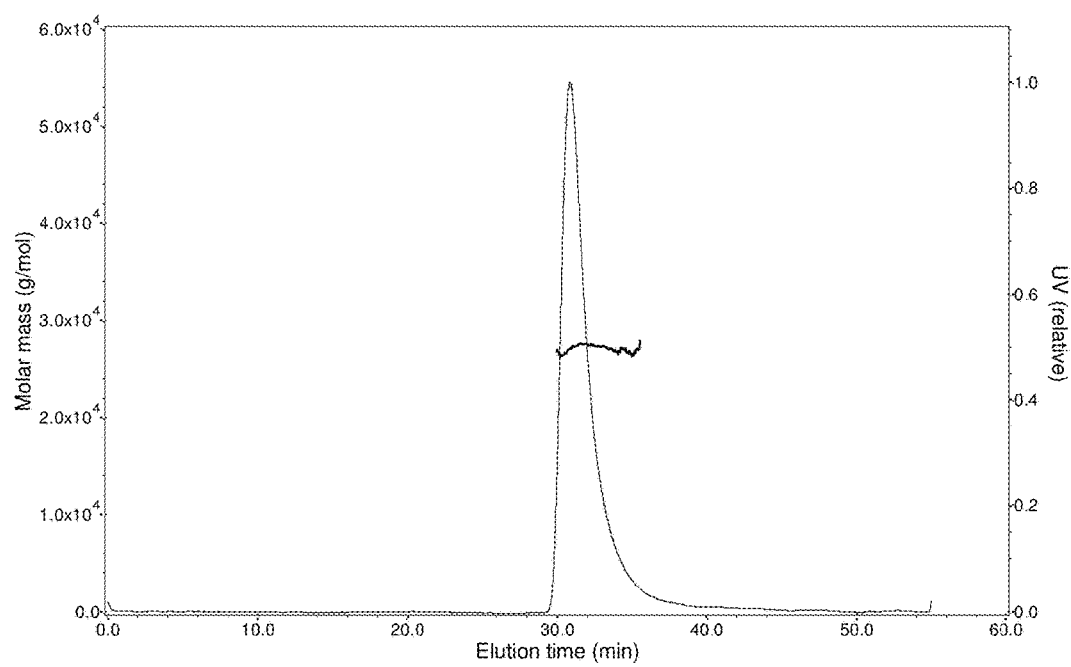

Fig. 14: Determination of the molecular weight of MPV.7
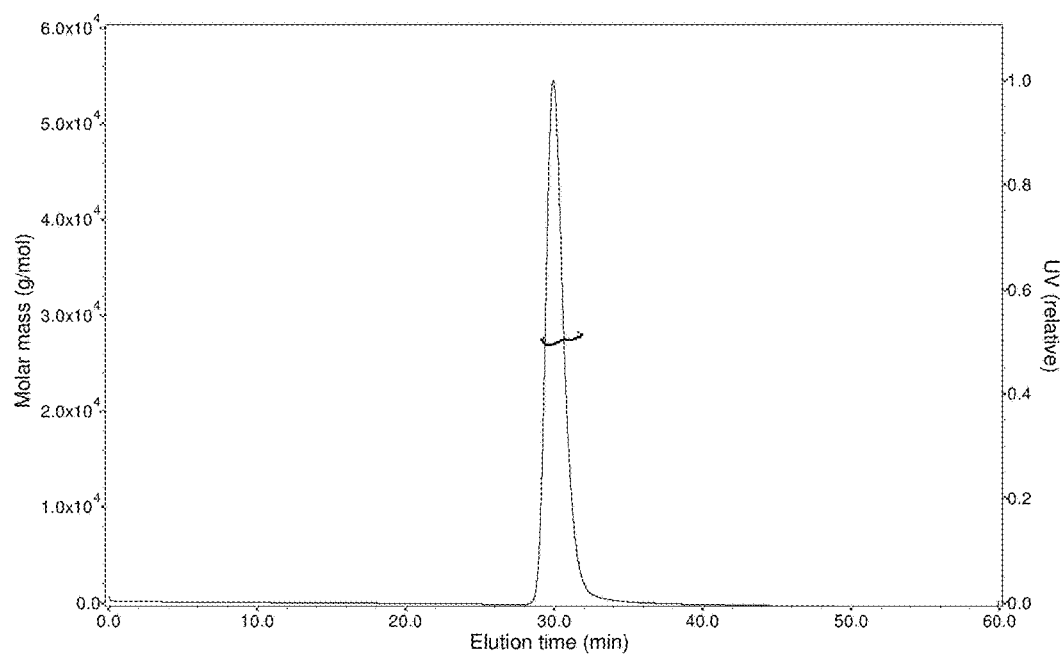

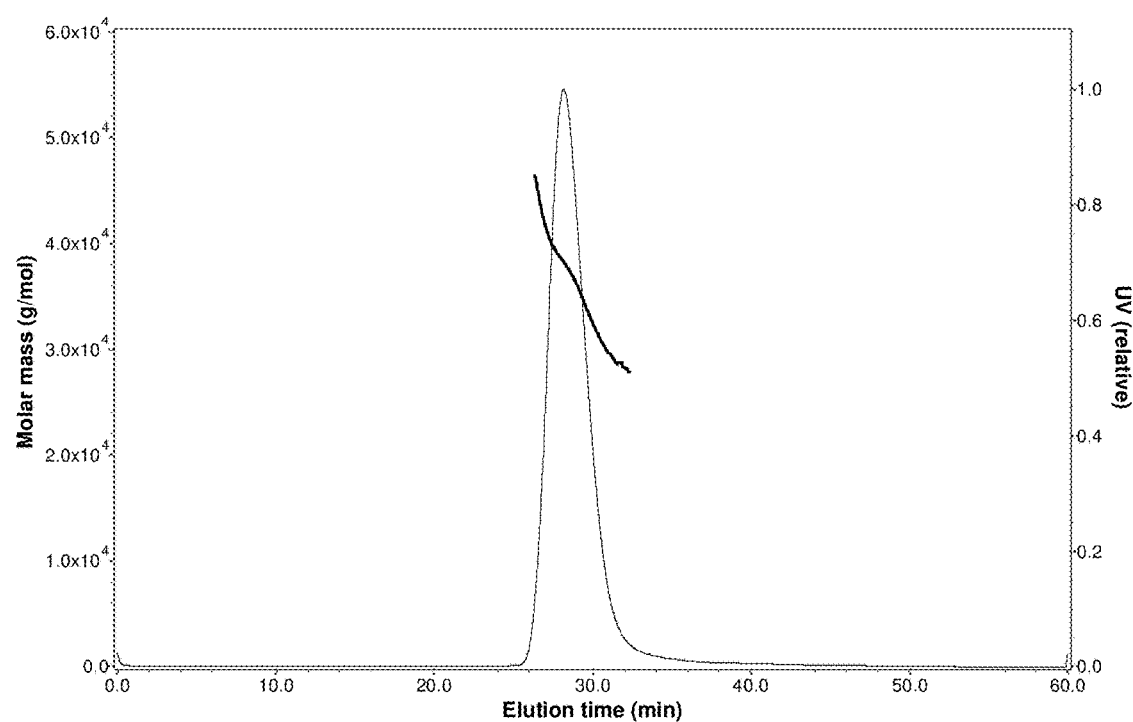
Fig. 15: Determination of the molecular weight of MPV.4

Fig. 16: Determination of the molecular weight of MPV.6
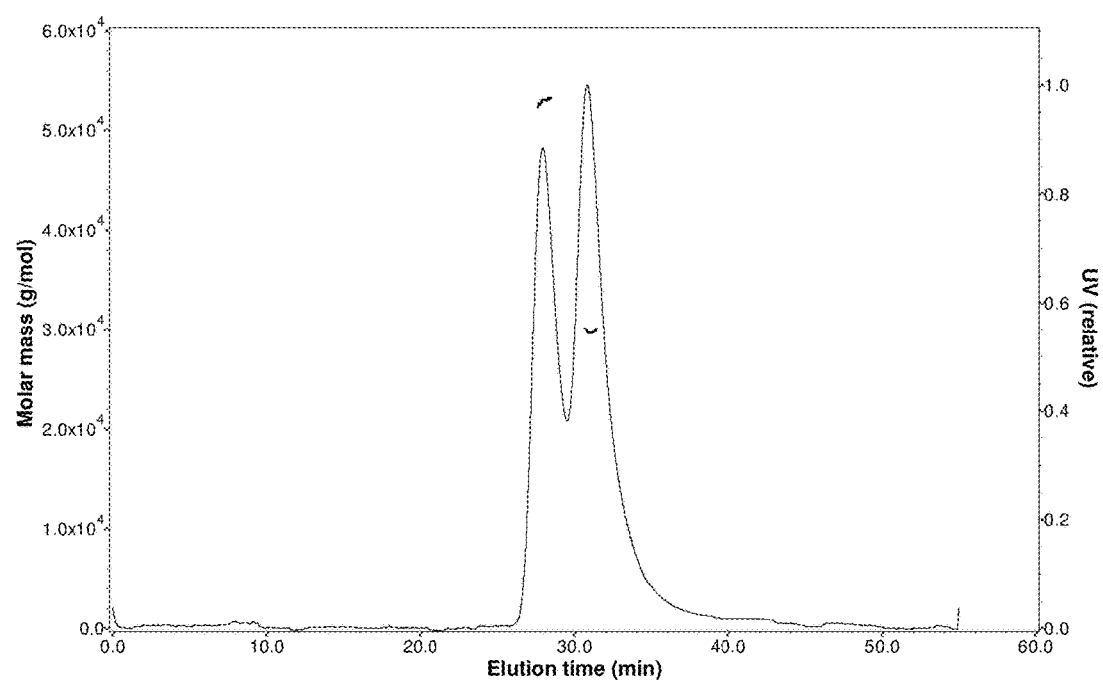

Fig. 17: IgE binding to immobilised MPV.4, MPV.5, MPV.6 and MPV.7
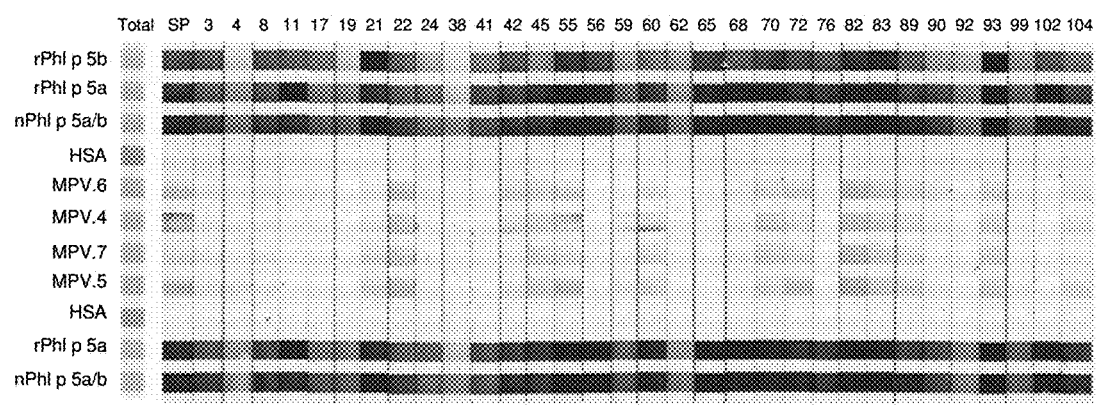

Fig. 18: IgE inhibition test with MPV.5 and MPV.4
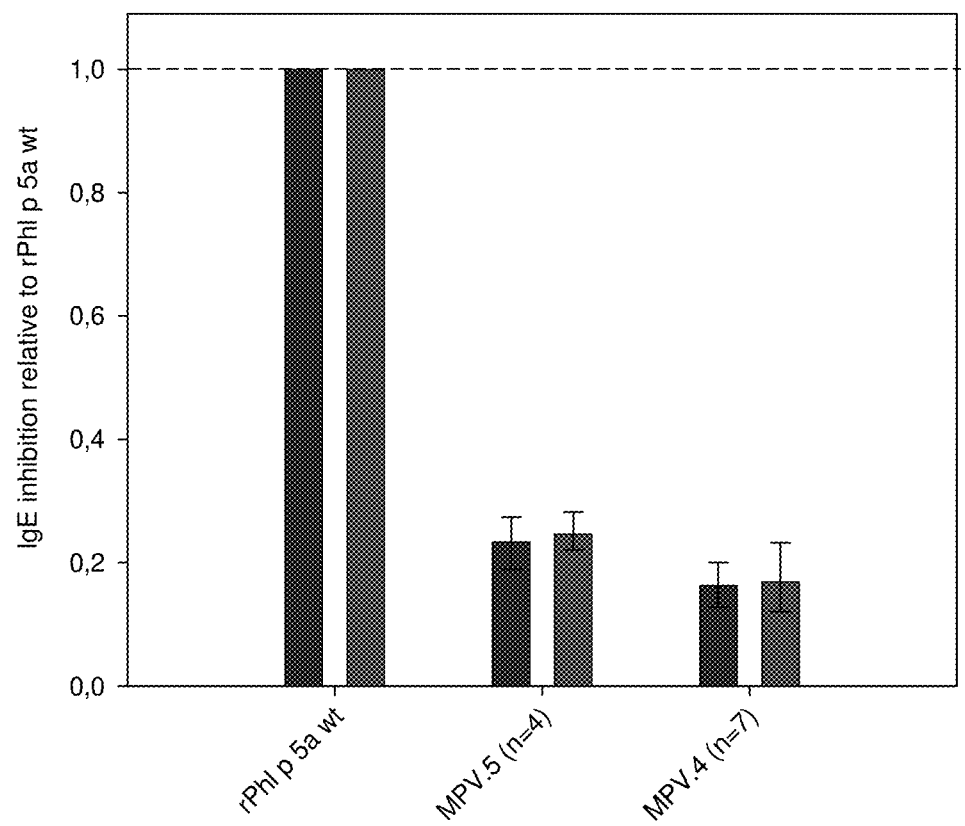

Fig. 19: IgE inhibition test with MPV.6 and MPV.7
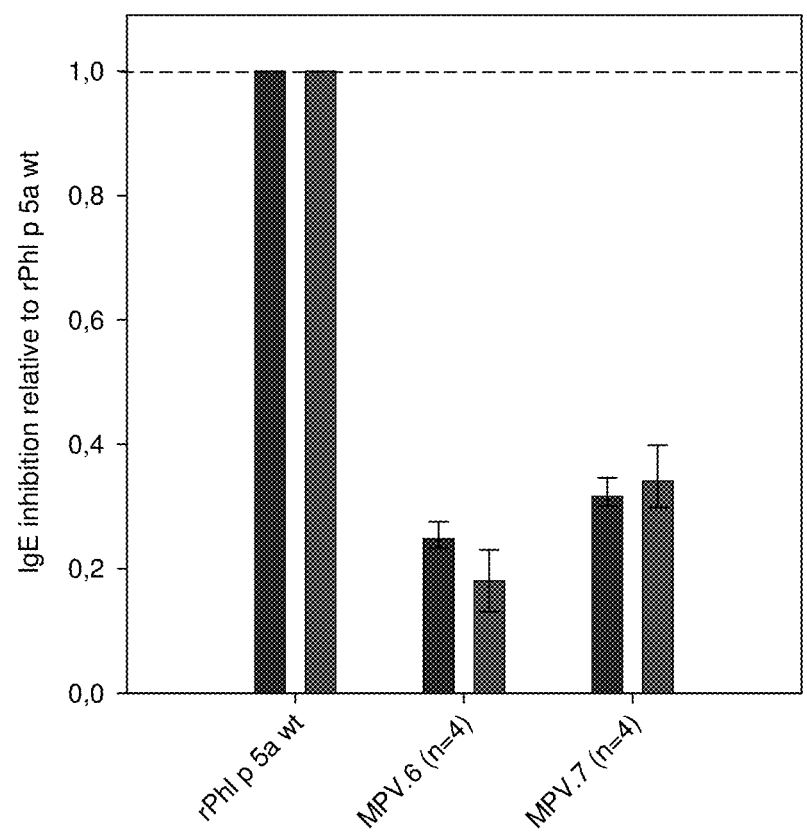

Fig. 20: Test for functional allergeneity of MPV.4

Fig. 21: Test for functional allergeneity of MPV.5

Fig. 22: Test for functional allergeneity of MPV.6

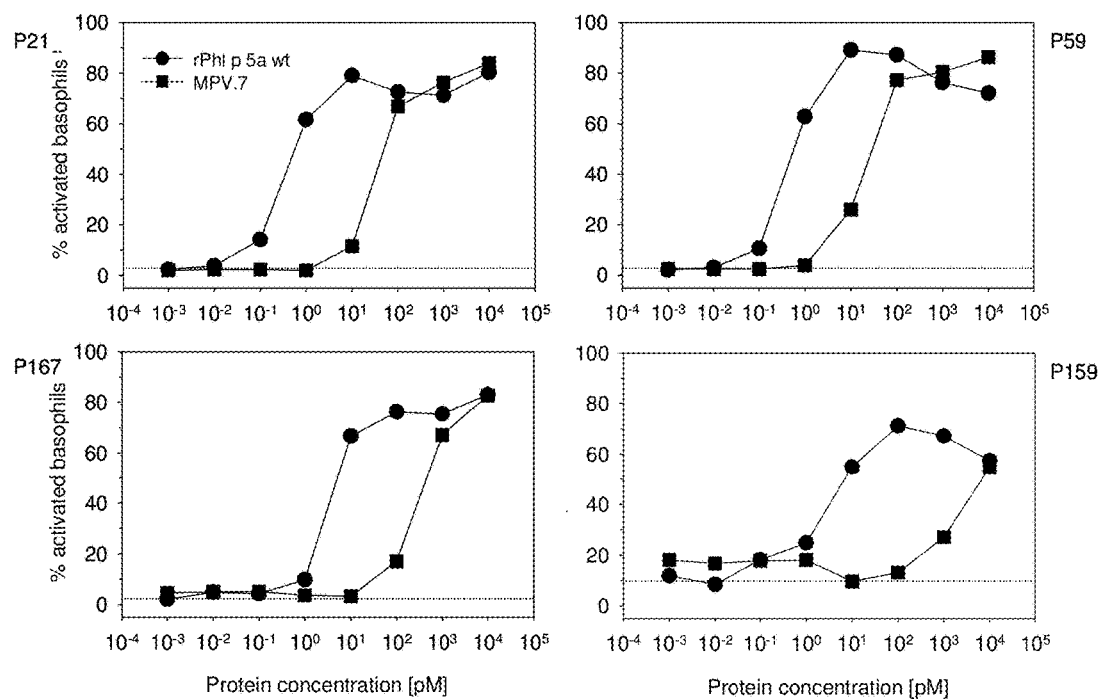
Fig. 23: Test for functional allergeneity; MPV.7

Fig. 24: rPhl p 5b wt precursor (IUIS entry Phl p 5.0201); deduced amino acid sequence 284 aa (Swiss prot: Q40963.2), SEQ ID NO:5

AAAAVPRRGPRGGPGRSYTADAGYAPATPAAAGAAAGKATTEEQKLIEDINVGFKAAVAAAA
SVPAADKFKTFEAAFTSSSKAAAAKAPGLVPKLDAAYSVAYKAAVGATPEAKFDSFVASLTEA
LRVIAGALEVHAVKPVTEEPGMAKIPAGELQIIDKIDAAFKVAATAAATAPADDKFTVFEAAFNK
AIKESTGGAYDTYKCIPSLEAAVKQAYAATVAAAPQVKYAVFEAALTKAITAMSEVQKVSQPA
TGAATVAAGAATTAAGAASGAATVAAGGYKV

SEQUENCE LISTING

<160> NUMBER OF SEQ ID NOS: 19

<210> SEQ ID NO 1
<211> LENGTH: 855
<212> TYPE: DNA
<213> ORGANISM: Phleum pratense

<400> SEQUENCE: 1

```
gccgatctag gctacggccc ggccacccca gctgccccgg ccgccggcta caccccgcc      60 gccccggccg gagcggagcc agcaggtaag gcgacgaccg aggagcagaa gctgatcgag     120
aagatcaacg ccggcttcaa ggcggccttg gccgctgccg ccggcgtccc gccagcggac     180
aagtacagga cgttcgtcgc aaccttcggc gcggcctcca caaggccttc gcggagggc      240 ctctcgggcg agcccaaggg cgccgccgaa tccagctcca aggccgcgct cacctccaag     300
ctcgacgccg cctacaagct cgcctacaag acagccgagg cgcgacgcc tgaggccaag      360 tacgacgcct acgtcgccac cctaagcgag gcgctccgca tcatcgccgg caccctcgag     420
gtccacgccg tcaagcccgc ggccgaggag gtcaaggtta tccctgccgg cgagctgcag     480
gtcatcgaga aggtcgacgc cgccttcaag gtcgctgcca ccgccgccaa cgccgcgccc     540
gccaacgaca agttcaccgt cttcgaggcc gccttcaaca acgccatcaa ggcgagcacg     600
ggcggcgcct acgagagcta caagttcatc cccgccctgg aggccgccgt caagcaggcc     660
tacgccgcca ccgtcgccac cgcgccggag gtcaagtaca ccgtctttga gaccgcgctg     720
aaaaaggcca tcaccgccat gtccgaggcc cagaaggctg ccaagcccgc tgccgctgcc     780
accgccaccg caacctccgc cgttggcgcg gccaccggcg ccgccaccgc cgctactggt     840
ggctacaaag tctga                                                      855
```

<210> SEQ ID NO 2
<211> LENGTH: 284
<212> TYPE: PRT
<213> ORGANISM: Phleum pratense

<400> SEQUENCE: 2

```
Ala Asp Leu Gly Tyr Gly Pro Ala Thr Pro Ala Ala Pro Ala Ala Gly
  1               5                  10                  15

Tyr Thr Pro Ala Ala Pro Ala Gly Ala Glu Pro Ala Gly Lys Ala Thr
             20                  25                  30

Thr Glu Glu Gln Lys Leu Ile Glu Lys Ile Asn Ala Gly Phe Lys Ala
         35                  40                  45

Ala Leu Ala Ala Ala Ala Gly Val Pro Pro Ala Asp Lys Tyr Arg Thr
 50                  55                  60

Phe Val Ala Thr Phe Gly Ala Ala Ser Asn Lys Ala Phe Ala Glu Gly
 65                  70                  75                  80

Leu Ser Gly Glu Pro Lys Gly Ala Ala Glu Ser Ser Lys Ala Ala
             85                  90                  95

Leu Thr Ser Lys Leu Asp Ala Ala Tyr Lys Leu Ala Tyr Lys Thr Ala
            100                 105                 110

Glu Gly Ala Thr Pro Glu Ala Lys Tyr Asp Ala Tyr Val Ala Thr Leu
            115                 120                 125

Ser Glu Ala Leu Arg Ile Ile Ala Gly Thr Leu Glu Val His Ala Val
130                 135                 140

Lys Pro Ala Ala Glu Glu Val Lys Val Ile Pro Ala Gly Glu Leu Gln
145                 150                 155                 160

Val Ile Glu Lys Val Asp Ala Ala Phe Lys Val Ala Thr Ala Ala
                165                 170                 175

Asn Ala Ala Pro Ala Asn Asp Lys Phe Thr Val Phe Glu Ala Ala Phe
            180                 185                 190

Asn Asn Ala Ile Lys Ala Ser Thr Gly Gly Ala Tyr Glu Ser Tyr Lys
        195                 200                 205

Phe Ile Pro Ala Leu Glu Ala Ala Val Lys Gln Ala Tyr Ala Ala Thr
    210                 215                 220

Val Ala Thr Ala Pro Glu Val Lys Tyr Thr Val Phe Glu Thr Ala Leu
225                 230                 235                 240

Lys Lys Ala Ile Thr Ala Met Ser Glu Ala Gln Lys Ala Ala Lys Pro
                245                 250                 255

Ala Ala Ala Ala Thr Ala Thr Ala Thr Ser Ala Val Gly Ala Ala Thr
            260                 265                 270

Gly Ala Ala Thr Ala Ala Thr Gly Gly Tyr Lys Val
            275                 280
```

<210> SEQ ID NO 3
<211> LENGTH: 57
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 3
atggcccttc accaccatca ccaccacgat atcccggaaa acctgtactt ccagggt     57

<210> SEQ ID NO 4
<211> LENGTH: 19
<212> TYPE: PRT
<213> ORGANISM: Artificial Sequence
<220> FEATURE:
<223> OTHER INFORMATION: Description of Artificial Sequence: Synthetic peptide

```
<400> SEQUENCE: 4

Met Ala Leu His His His His His His Asp Ile Pro Glu Asn Leu Tyr
1               5                   10                  15

Phe Gln Gly

<210> SEQ ID NO 5
<211> LENGTH: 284
<212> TYPE: PRT
<213> ORGANISM: Phleum pratense

<400> SEQUENCE: 5

Ala Ala Ala Ala Val Pro Arg Arg Gly Pro Arg Gly Gly Pro Gly Arg
1               5                   10                  15

Ser Tyr Thr Ala Asp Ala Gly Tyr Ala Pro Ala Thr Pro Ala Ala Ala
            20                  25                  30

Gly Ala Ala Ala Gly Lys Ala Thr Thr Glu Glu Gln Lys Leu Ile Glu
        35                  40                  45

Asp Ile Asn Val Gly Phe Lys Ala Ala Val Ala Ala Ala Ala Ser Val
    50                  55                  60

Pro Ala Ala Asp Lys Phe Lys Thr Phe Glu Ala Ala Phe Thr Ser Ser
65                  70                  75                  80

Ser Lys Ala Ala Ala Ala Lys Ala Pro Gly Leu Val Pro Lys Leu Asp
                85                  90                  95

Ala Ala Tyr Ser Val Ala Tyr Lys Ala Ala Val Gly Ala Thr Pro Glu
            100                 105                 110

Ala Lys Phe Asp Ser Phe Val Ala Ser Leu Thr Glu Ala Leu Arg Val
        115                 120                 125

Ile Ala Gly Ala Leu Glu Val His Ala Val Lys Pro Val Thr Glu Glu
    130                 135                 140

Pro Gly Met Ala Lys Ile Pro Ala Gly Glu Leu Gln Ile Ile Asp Lys
145                 150                 155                 160

Ile Asp Ala Ala Phe Lys Val Ala Ala Thr Ala Ala Thr Ala Pro
                165                 170                 175

Ala Asp Asp Lys Phe Thr Val Phe Glu Ala Ala Phe Asn Lys Ala Ile
            180                 185                 190

Lys Glu Ser Thr Gly Gly Ala Tyr Asp Thr Tyr Lys Cys Ile Pro Ser
        195                 200                 205

Leu Glu Ala Ala Val Lys Gln Ala Tyr Ala Ala Thr Val Ala Ala Ala
    210                 215                 220

Pro Gln Val Lys Tyr Ala Val Phe Glu Ala Ala Leu Thr Lys Ala Ile
225                 230                 235                 240

Thr Ala Met Ser Glu Val Gln Lys Val Ser Gln Pro Ala Thr Gly Ala
                245                 250                 255

Ala Thr Val Ala Ala Gly Ala Ala Thr Thr Ala Ala Gly Ala Ala Ser
            260                 265                 270

Gly Ala Ala Thr Val Ala Ala Gly Gly Tyr Lys Val
        275                 280

<210> SEQ ID NO 6
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 6
```

His His His His His His
1               5

<210> SEQ ID NO 7
<211> LENGTH: 9
<212> TYPE: PRT
<213> ORGANISM: Phleum pratense

<400> SEQUENCE: 7

Ala Asp Leu Gly Tyr Gly Pro Ala Thr
1               5

<210> SEQ ID NO 8
<211> LENGTH: 287
<212> TYPE: PRT
<213> ORGANISM: Phleum pratense

<400> SEQUENCE: 8

Ala Asp Leu Gly Tyr Gly Pro Ala Thr Pro Ala Ala Pro Ala Gly
1               5                   10                  15

Tyr Thr Pro Ala Thr Pro Ala Ala Pro Ala Glu Ala Ala Pro Ala Gly
                20                  25                  30

Lys Ala Thr Thr Glu Glu Gln Lys Leu Ile Glu Lys Ile Asn Ala Gly
            35                  40                  45

Phe Lys Ala Ala Leu Ala Ala Ala Gly Val Gln Pro Ala Asp Lys
 50                  55                  60

Tyr Arg Thr Phe Val Ala Thr Phe Gly Ala Ala Ser Asn Lys Ala Phe
 65                  70                  75                  80

Ala Glu Gly Leu Ser Gly Glu Pro Lys Gly Ala Ala Glu Ser Ser Ser
                85                  90                  95

Lys Ala Ala Leu Thr Ser Lys Leu Asp Ala Ala Tyr Lys Leu Ala Tyr
            100                 105                 110

Lys Thr Ala Glu Gly Ala Thr Pro Glu Ala Lys Tyr Asp Ala Tyr Val
        115                 120                 125

Ala Thr Leu Ser Glu Ala Leu Arg Ile Ile Ala Gly Thr Leu Glu Val
130                 135                 140

His Ala Val Lys Pro Ala Ala Glu Glu Val Lys Val Ile Pro Ala Gly
145                 150                 155                 160

Glu Leu Gln Val Ile Glu Lys Val Asp Ala Ala Phe Lys Val Ala Ala
                165                 170                 175

Thr Ala Ala Asn Ala Ala Pro Ala Asn Asp Lys Phe Thr Val Phe Glu
            180                 185                 190

Ala Ala Phe Asn Asp Ala Ile Lys Ala Ser Thr Gly Gly Ala Tyr Glu
        195                 200                 205

Ser Tyr Lys Phe Ile Pro Ala Leu Glu Ala Ala Val Lys Gln Ala Tyr
    210                 215                 220

Ala Ala Thr Val Ala Thr Ala Pro Glu Val Lys Tyr Thr Val Phe Glu
225                 230                 235                 240

Thr Ala Leu Lys Lys Ala Ile Thr Ala Met Ser Glu Ala Gln Lys Ala
                245                 250                 255

Ala Lys Pro Ala Ala Ala Ala Thr Ala Thr Ala Ala Val Gly
            260                 265                 270

Ala Ala Thr Gly Ala Ala Thr Ala Ala Thr Gly Gly Tyr Lys Val
        275                 280                 285

<210> SEQ ID NO 9

```
<211> LENGTH: 276
<212> TYPE: PRT
<213> ORGANISM: Phleum pratense

<400> SEQUENCE: 9

Ala Asp Leu Gly Tyr Gly Gly Pro Ala Thr Pro Ala Ala Pro Ala Glu
1               5                   10                  15

Ala Ala Pro Ala Gly Lys Ala Thr Thr Glu Glu Gln Lys Leu Ile Glu
            20                  25                  30

Lys Ile Asn Asp Gly Phe Lys Ala Leu Ala Ala Ala Ala Gly Val
        35                  40                  45

Pro Pro Ala Asp Lys Tyr Lys Thr Phe Val Ala Thr Phe Gly Ala Ala
    50                  55                  60

Ser Asn Lys Ala Phe Ala Glu Gly Leu Ser Ala Glu Pro Lys Gly Ala
65                  70                  75                  80

Ala Glu Ser Ser Ser Lys Gly Ala Leu Thr Ser Lys Leu Glu Ala Ala
                85                  90                  95

Tyr Lys Leu Ala Tyr Lys Thr Ser Glu Gly Ala Thr Pro Glu Ala Lys
            100                 105                 110

Tyr Asp Ala Tyr Val Ala Thr Leu Ser Glu Ala Leu Arg Ile Ile Ala
        115                 120                 125

Gly Thr Leu Glu Val His Ala Val Lys Pro Ala Ala Glu Glu Val Lys
    130                 135                 140

Val Ile Pro Ala Gly Glu Leu Gln Phe Ile Glu Lys Val Asp Ser Ala
145                 150                 155                 160

Leu Lys Val Ala Ala Thr Ala Ala Asn Ala Ala Ala Asn Asp Lys
                165                 170                 175

Phe Thr Val Phe Glu Ala Ala Phe Asn His Ala Ile Lys Ala Ser Thr
            180                 185                 190

Gly Gly Ala Tyr Glu Ser Tyr Lys Phe Ile Pro Ala Leu Glu Ala Ala
        195                 200                 205

Val Lys Gln Ala Tyr Ala Ala Thr Val Ala Thr Ala Pro Glu Val Lys
    210                 215                 220

Tyr Thr Val Phe Glu Thr Ala Leu Lys Lys Ala Ile Thr Ala Met Ser
225                 230                 235                 240

Glu Ala Gln Lys Ala Ala Lys Pro Ala Thr Glu Ala Thr Ala Thr Ala
                245                 250                 255

Thr Ala Ala Val Gly Ala Ala Thr Gly Ala Ala Thr Ala Ala Thr Gly
                260                 265                 270

Gly Tyr Lys Val
        275

<210> SEQ ID NO 10
<211> LENGTH: 265
<212> TYPE: PRT
<213> ORGANISM: Phleum pratense

<400> SEQUENCE: 10

Ala Asp Ala Gly Tyr Ala Pro Ala Thr Pro Ala Ala Ala Gly Ala Ala
1               5                   10                  15

Ala Gly Lys Ala Thr Thr Glu Glu Gln Lys Leu Ile Glu Asp Ile Asn
            20                  25                  30

Val Gly Phe Lys Ala Ala Val Ala Ala Ala Ser Val Pro Ala Ala
        35                  40                  45

Asp Lys Phe Lys Thr Phe Glu Ala Ala Phe Thr Ser Ser Ser Lys Ala
    50                  55                  60
```

```
Ala Ala Ala Lys Ala Pro Gly Leu Val Pro Lys Leu Asp Ala Tyr
 65                  70                  75                  80

Ser Val Ala Tyr Lys Ala Val Gly Ala Thr Pro Glu Ala Lys Phe
                 85                  90                  95

Asp Ser Phe Val Ala Ser Leu Thr Glu Ala Leu Arg Val Ile Ala Gly
            100                 105                 110

Ala Leu Glu Val His Ala Val Lys Pro Val Thr Glu Pro Gly Met
            115                 120                 125

Ala Lys Ile Pro Ala Gly Glu Leu Gln Ile Ile Asp Lys Ile Asp Ala
        130                 135                 140

Ala Phe Lys Val Ala Ala Thr Ala Ala Thr Ala Pro Ala Asp Asp
145                 150                 155                 160

Lys Phe Thr Val Phe Glu Ala Ala Phe Asn Lys Ala Ile Lys Glu Ser
                165                 170                 175

Thr Gly Gly Ala Tyr Asp Thr Tyr Lys Cys Ile Pro Ser Leu Glu Ala
            180                 185                 190

Ala Val Lys Gln Ala Tyr Ala Ala Thr Val Ala Ala Pro Gln Val
            195                 200                 205

Lys Tyr Ala Val Phe Glu Ala Ala Leu Thr Lys Ala Ile Thr Ala Met
210                 215                 220

Ser Glu Val Gln Lys Val Ser Gln Pro Ala Thr Gly Ala Ala Thr Val
225                 230                 235                 240

Ala Ala Gly Ala Ala Thr Thr Ala Ala Gly Ala Ala Ser Gly Ala Ala
            245                 250                 255

Thr Val Ala Ala Gly Gly Tyr Lys Val
            260                 265

<210> SEQ ID NO 11
<211> LENGTH: 110
<212> TYPE: PRT
<213> ORGANISM: Phleum pratense

<400> SEQUENCE: 11

Gly Lys Ala Thr Thr Glu Glu Gln Lys Leu Ile Glu Asp Val Asn Ala
1               5                   10                  15

Ser Phe Arg Ala Ala Met Ala Thr Thr Ala Asn Val Pro Pro Ala Asp
                20                  25                  30

Lys Tyr Lys Thr Phe Glu Ala Ala Phe Thr Val Ser Ser Lys Arg Asn
            35                  40                  45

Leu Ala Asp Ala Val Ser Lys Ala Pro Gln Leu Val Pro Lys Leu Asp
        50                  55                  60

Glu Val Tyr Asn Ala Ala Tyr Asn Ala Ala Asp His Ala Ala Pro Glu
65                  70                  75                  80

Asp Lys Tyr Glu Ala Phe Val Leu His Phe Ser Glu Ala Leu Arg Ile
                85                  90                  95

Ile Ala Gly Thr Pro Glu Val His Ala Val Lys Pro Gly Ala
            100                 105                 110

<210> SEQ ID NO 12
<211> LENGTH: 314
<212> TYPE: PRT
<213> ORGANISM: Lolium perenne

<400> SEQUENCE: 12

Ala Asp Ala Gly Tyr Ala Pro Ala Thr Pro Ala Thr Pro Ala Ala Pro
1               5                   10                  15
```

```
Ala Thr Ala Ala Thr Pro Ala Thr Pro Ala Thr Pro Ala
            20                  25                  30
Ala Val Pro Ser Gly Lys Ala Thr Glu Glu Gln Lys Leu Ile Glu
            35                  40                  45
Lys Ile Asn Ala Gly Phe Lys Ala Val Ala Ala Ala Val Val
 50                  55                  60
Pro Pro Ala Asp Lys Tyr Lys Thr Phe Val Glu Thr Phe Gly Thr Ala
 65                  70                  75                  80
Thr Asn Lys Ala Phe Val Glu Gly Leu Ala Ser Gly Tyr Ala Asp Gln
                     85                  90                  95
Ser Lys Asn Gln Leu Thr Ser Lys Leu Asp Ala Ala Leu Lys Leu Ala
                100                 105                 110
Tyr Glu Ala Ala Gln Gly Ala Thr Pro Glu Ala Lys Tyr Asp Ala Tyr
                115                 120                 125
Val Ala Thr Leu Thr Glu Ala Leu Arg Val Ile Ala Gly Thr Leu Glu
130                 135                 140
Val His Ala Val Lys Pro Ala Ala Glu Glu Val Lys Val Gly Ala Ile
145                 150                 155                 160
Pro Ala Ala Glu Val Gln Leu Ile Asp Lys Val Asp Ala Ala Tyr Arg
                165                 170                 175
Thr Ala Ala Thr Ala Ala Asn Ala Ala Pro Ala Asn Asp Lys Phe Thr
                180                 185                 190
Val Phe Glu Asn Thr Phe Asn Asn Ala Ile Lys Val Ser Leu Gly Ala
                195                 200                 205
Ala Tyr Asp Ser Tyr Lys Phe Ile Pro Thr Leu Val Ala Ala Val Lys
                210                 215                 220
Gln Ala Tyr Ala Ala Lys Gln Ala Thr Ala Pro Glu Val Lys Tyr Thr
225                 230                 235                 240
Val Ser Glu Thr Ala Leu Lys Lys Ala Val Thr Ala Met Ser Glu Ala
                245                 250                 255
Glu Lys Glu Ala Thr Pro Ala Ala Ala Thr Ala Thr Pro Thr Pro
                260                 265                 270
Ala Ala Ala Thr Ala Thr Ala Thr Pro Ala Ala Ala Tyr Ala Thr Ala
                275                 280                 285
Thr Pro Ala Ala Ala Thr Ala Thr Ala Thr Pro Ala Ala Ala Thr Ala
                290                 295                 300
Thr Pro Ala Ala Ala Gly Gly Tyr Lys Val
305                 310

<210> SEQ ID NO 13
<211> LENGTH: 297
<212> TYPE: PRT
<213> ORGANISM: Phalaris aquatica

<400> SEQUENCE: 13

Thr Pro Pro Thr Pro Arg Thr Pro Pro Leu Leu Pro Pro Pro Arg Ala
 1               5                  10                  15
Arg Asp Lys Ala Thr Leu Thr Ser Arg Ser Val Glu Asp Ile Asn Ala
                20                  25                  30
Ala Ser Arg Arg Pro Trp Trp Ala Ser Val Pro Pro Ala Asp Lys Phe
                35                  40                  45
Lys Thr Phe Ala Asp His Val Leu Cys Val Pro Asn Ala Asp Val Thr
 50                  55                  60
Ser Ala Ala Thr Lys Ala Pro Gln Leu Lys Ala Lys Leu Asp Ala Ala
```

```
                65                  70                  75                  80
Tyr Arg Val Ala Tyr Glu Ala Ala Glu Gly Ser Thr Pro Glu Ala Lys
                    85                  90                  95
Tyr Asp Ala Phe Ile Ala Ala Leu Thr Glu Ala Leu Arg Val Ile Ala
                100                 105                 110
Gly Ala Phe Glu Val His Ala Val Lys Pro Ala Thr Glu Val Val
                115                 120                 125
Ala Asp Pro Val Gly Glu Leu Gln Ile Val Asp Lys Ile Asp Ala Ala
130                 135                 140
Phe Lys Ile Ala Ala Thr Ala Ala Asn Ser Ala Pro Ala Asn Asp Lys
145                 150                 155                 160
Phe Thr Val Phe Glu Gly Ala Phe Asn Lys Ala Ile Lys Glu Ser Thr
                165                 170                 175
Ala Gly Ala Tyr Glu Thr Tyr Lys Phe Ile Pro Ser Leu Glu Ala Ala
                180                 185                 190
Val Lys Gln Ala Tyr Gly Ala Thr Val Ala Arg Ala Pro Glu Val Lys
                195                 200                 205
Tyr Ala Val Phe Glu Ala Gly Leu Thr Lys Ala Ile Thr Ala Met Ser
210                 215                 220
Glu Ala Gln Lys Val Ala Lys Pro Pro Leu Ser Pro Gln Pro Pro Gln
225                 230                 235                 240
Val Leu Pro Leu Ala Ala Gly Ala Ala Thr Val Ala Ala Ala Ser
                245                 250                 255
Asp Val Arg Val Cys Arg Ser His Gly Thr Leu Gln Asp Ala Cys Leu
                260                 265                 270
Leu Arg Cys Arg Gly Gly Cys Gln Pro Val Val Trp Arg Gly Gly Ser
                275                 280                 285
His Arg Ala Arg Gly Gly Tyr Lys Val
                290                 295

<210> SEQ ID NO 14
<211> LENGTH: 265
<212> TYPE: PRT
<213> ORGANISM: Dactylis glomerata

<400> SEQUENCE: 14

Ala Asp Ala Gly Tyr Thr Pro Ala Ala Ala Thr Pro Ala Thr Ala
1               5                   10                  15
Gly Gly Lys Ala Met Thr Glu Glu Gln Thr Leu Ile Glu Asp Val Asn
                20                  25                  30
Ala Gly Phe Lys Ala Ala Val Ala Ala Ala Ser Ser Ala Pro Pro Ala
                35                  40                  45
Asp Lys Phe Lys Thr Phe Glu Ala Thr Phe Thr Ala Ala Cys Lys Ala
                50                  55                  60
Asn Ile Ala Ala Ala Ala Thr Lys Val Pro Leu Phe Val Ala Lys Leu
65                  70                  75                  80
Asp Ala Ala Tyr Ala Val Ala Tyr Lys Thr Ala Thr Gly Pro Thr Pro
                85                  90                  95
Glu Ala Lys Tyr Asp Ala Phe Val Ala Ala Leu Thr Glu Ala Leu Arg
                100                 105                 110
Val Ile Ala Gly Ala Leu Glu Val His Ala Val Lys Pro Ala Ala Glu
                115                 120                 125
Glu Val Pro Ala Ala Lys Ile Pro Ala Gly Glu Leu Gln Ile Val Asp
                130                 135                 140
```

```
Lys Ile Asp Ala Ala Tyr Lys Ile Ala Ala Thr Ala Asn Ala Ala
145                 150                 155                 160

Pro Ala Asn Asp Lys Phe Thr Val Phe Glu Gly Ala Phe Asn Lys Ala
                165                 170                 175

Ile Lys Glu Ser Thr Gly Gly Ala Tyr Glu Ser Tyr Lys Phe Ile Pro
            180                 185                 190

Thr Leu Glu Ala Ala Val Lys Gln Ala Tyr Ala Ala Thr Val Ala Ala
        195                 200                 205

Ala Pro Glu Val Lys Tyr Ala Val Phe Glu Ala Ala Leu Thr Lys Ala
    210                 215                 220

Ile Thr Ala Met Ser Glu Ala Gln Lys Val Ala Thr Pro Ala Ala Val
225                 230                 235                 240

Ala Thr Gly Ala Ala Thr Ala Ala Ala Ser Ala Ala Thr Gly Ala Ala
                245                 250                 255

Thr Ala Ala Ala Gly Gly Tyr Lys Val
            260                 265

<210> SEQ ID NO 15
<211> LENGTH: 264
<212> TYPE: PRT
<213> ORGANISM: Holcus lanatus

<400> SEQUENCE: 15

Ala Asp Ala Gly Tyr Thr Pro Ala Ala Pro Ala Ala Gly Ala Gly
1               5                   10                  15

Gly Lys Ala Thr Thr Asp Glu Gln Lys Leu Leu Glu Asp Val Asn Ala
                20                  25                  30

Gly Phe Lys Thr Ala Val Ala Ala Ala Asn Val Pro Pro Ala Asp
            35                  40                  45

Lys Tyr Lys Thr Phe Glu Ala Ala Phe Thr Ala Ser Ser Lys Ala Ser
50                  55                  60

Ile Ala Ala Ala Thr Lys Ala Pro Gly Leu Ile Pro Gln Leu Asn
65                  70                  75                  80

Ala Ala Thr Asn Thr Ala Tyr Ala Ala Ala Gln Gly Ala Thr Pro Glu
                85                  90                  95

Ala Lys Tyr Asp Ala Phe Val Thr Thr Leu Thr Glu Ala Leu Arg Val
            100                 105                 110

Ile Ala Gly Ala Leu Glu Val His Ala Val Lys Pro Ala Thr Glu Glu
        115                 120                 125

Val Gly Ala Ala Lys Ile Pro Ala Gly Glu Leu Gln Ile Val Asp Lys
    130                 135                 140

Ile Asp Ala Ala Phe Arg Ile Ala Ala Thr Ala Ala Asn Ala Ala Pro
145                 150                 155                 160

Val Asn Asp Lys Phe Thr Val Phe Glu Gly Ala Phe Asn Lys Ala Ile
                165                 170                 175

Lys Glu Ser Thr Gly Gly Ala Tyr Glu Ala Tyr Lys Phe Ile Pro Ser
            180                 185                 190

Leu Glu Thr Ala Val Lys Gln Ala Tyr Ala Ala Thr Val Ala Thr Ala
        195                 200                 205

Pro Glu Val Lys Tyr Thr Val Phe Glu Thr Ala Leu Lys Lys Ala Ile
    210                 215                 220

Thr Ala Met Ser Glu Ala Gln Lys Glu Ala Lys Pro Val Ala Ala Ala
225                 230                 235                 240

Thr Gly Ala Ala Thr Ala Ala Ala Gly Val Ala Ala Gly Ala Ala Thr
                245                 250                 255
```

-continued

```
Ala Ala Ala Gly Gly Tyr Lys Val
            260

<210> SEQ ID NO 16
<211> LENGTH: 240
<212> TYPE: PRT
<213> ORGANISM: Holcus lanatus

<400> SEQUENCE: 16

Gln Lys Leu Leu Glu Asp Val Asn Ala Ser Phe Lys Ala Val Ala
1               5                   10                  15

Ala Ala Ala Lys Val Pro Pro Ala Asp Lys Tyr Lys Thr Phe Leu Arg
                20                  25                  30

Ala Phe Thr Val Leu Asp Arg Gly Ser Thr Glu Gln Ser Lys Ala Glu
            35                  40                  45

Glu Thr Lys Met Pro Glu Leu Ser Ser Lys Leu Val Asp Ala Tyr Met
        50                  55                  60

Ala Ala Phe Lys Ala Ser Thr Gly Gly Thr Gln Glu Ala Lys Tyr Asp
65                  70                  75                  80

Ala Phe Val Thr Thr Leu Thr Glu Ala Leu Arg Val Ile Ala Gly Ala
                85                  90                  95

Leu Glu Val His Ala Val Lys Pro Ala Thr Glu Glu Val Pro Ala Ala
            100                 105                 110

Lys Ile Pro Ala Gly Asp Leu Gln Val Val Asp Lys Ile Asp Ala Ser
        115                 120                 125

Phe Lys Ile Ala Ala Thr Ala Ala Asn Ala Ala Pro Ala Asn Asp Lys
130                 135                 140

Phe Thr Val Phe Glu Thr Ala Phe Asn Lys Ala Leu Lys Glu Ser Thr
145                 150                 155                 160

Gly Gly Ala Tyr Glu Ser Tyr Lys Phe Ile Pro Ser Leu Glu Ala Ala
                165                 170                 175

Val Lys Gln Ala Tyr Ala Ser Thr Val Ala Ala Ala Pro Glu Val Lys
            180                 185                 190

Tyr Ala Val Phe Glu Ala Ala Leu Thr Lys Ala Ile Thr Ala Met Ser
        195                 200                 205

Gln Ala Gln Lys Val Ala Gln Pro Ala Ala Ala Thr Gly Ala Ala
            210                 215                 220

Thr Val Ala Ala Gly Ala Ala Thr Thr Ala Ala Gly Gly Tyr Lys Val
225                 230                 235                 240

<210> SEQ ID NO 17
<211> LENGTH: 278
<212> TYPE: PRT
<213> ORGANISM: Poa pratensis

<400> SEQUENCE: 17

Ala Asp Ala Gly Tyr Ala Pro Ala Thr Pro Ala Ala Ala Gly Ala Ala
1               5                   10                  15

Ala Gly Lys Ile Thr Pro Thr Gln Glu Gln Lys Leu Met Glu Asp Ile
                20                  25                  30

Asn Val Gly Phe Lys Ala Ala Val Ala Ala Ala Ala Gly Ala Pro Pro
            35                  40                  45

Ala Asp Lys Phe Lys Thr Phe Gln Ala Ala Phe Ser Ala Ser Val Glu
        50                  55                  60

Ala Ser Ala Ala Lys Leu Asn Ala Ala Gln Ala Pro Gly Phe Val Ser
65                  70                  75                  80
```

```
His Val Ala Ala Thr Ser Asp Ala Thr Tyr Lys Ala Ala Val Gly Ala
                85                  90                  95

Thr Pro Glu Ala Lys Phe Asp Ser Phe Val Ala Ala Phe Thr Glu Ala
            100                 105                 110

Leu Arg Ile Ile Ala Gly Val Leu Lys Val His Ala Val Lys Pro Ile
        115                 120                 125

Thr Glu Glu Thr Gly Ala Ala Lys Ile Pro Ala Gly Glu Gln Gln Ile
    130                 135                 140

Ile Asp Lys Ile Asp Ala Ala Phe Lys Val Ala Ala Thr Ala Ala Asn
145                 150                 155                 160

Ala Ala Pro Ala Asn Asp Lys Phe Thr Val Phe Glu Ala Ala Phe Asn
                165                 170                 175

Asn Ala Ile Lys Glu Ser Thr Gly Gly Ala Tyr Asp Thr Tyr Lys Ser
            180                 185                 190

Ile Pro Ser Leu Glu Ala Ala Val Lys Gln Ala Tyr Ala Ala Thr Ile
        195                 200                 205

Ala Ala Ala Pro Glu Val Lys Phe Ala Val Phe Lys Ala Ala Leu Thr
    210                 215                 220

Lys Ala Ile Thr Ala Met Ala Glu Val Gln Lys Val Ser Lys Pro Val
225                 230                 235                 240

Ala Gly Ala Ala Thr Val Ala Ala Gly Ala Ala Thr Ala Ala Thr Gly
                245                 250                 255

Ala Ala Thr Gly Ala Ala Gly Ala Ala Thr Gly Ala Ala Thr Val Ser
            260                 265                 270

Ala Gly Gly Tyr Lys Val
        275

<210> SEQ ID NO 18
<211> LENGTH: 231
<212> TYPE: PRT
<213> ORGANISM: Triticum aestivum

<400> SEQUENCE: 18

Thr Thr Glu Glu Gln Asn Val Met Glu Gln Val Asn Asn Ala Phe Lys
1               5                   10                  15

Ala Ala Val Ala Ala Ala Val Val Pro Gly Pro Asp Lys Tyr Lys Lys
            20                  25                  30

Lys Phe Thr Asp Thr Tyr Ile Pro Asp Val Asp Arg Ala Ile Ala Asp
        35                  40                  45

Val Phe Lys Gly Ser Asn Ala Ser Thr Phe Thr Ala Lys Ile Gly Met
    50                  55                  60

Ala Gln Lys Leu Ala Tyr Asp Ser Ala Asp Gly Ala Thr Pro Glu Ala
65                  70                  75                  80

Lys Tyr Asp Ser Phe Ile Ala Ile Leu Ser Glu Ser Leu Arg Ile Ile
                85                  90                  95

Ala Gly Thr Leu Glu Ile His Gly Val Lys Pro Ala Thr Glu Glu Val
            100                 105                 110

Lys Gly Pro Ile Pro Ala Ala Glu Met Gln Ala Val Asn Gln Ile Asp
        115                 120                 125

Thr Ala Phe Arg Ile Ala Ala Thr Ala Ala Asp Ala Pro Val Asn
    130                 135                 140

Asp Lys Phe Thr Val Phe Glu Ser Ala Phe Asp Lys Ala Ile Lys Glu
145                 150                 155                 160

Thr Thr Gly Gly Ala Tyr Ala Gly Tyr Lys Phe Val Pro Ala Leu Glu
```

```
                            165                 170                 175
Ser Ala Val Lys Lys Ala Tyr Ala Ala Thr Val Ala Glu Ala Pro Glu
                180                 185                 190

Val Lys Phe Thr Val Phe Glu Ala Ala Leu Thr Arg Thr Ile Ala Ala
            195                 200                 205

Met Cys Val Ala Ala Lys Gly Ala Ala Gly Ala Ser Asn Gly Thr Asp
210                 215                 220

Ala Ala Gly Gly Tyr Lys Ala
225                 230

<210> SEQ ID NO 19
<211> LENGTH: 275
<212> TYPE: PRT
<213> ORGANISM: Hordeum vulgare

<400> SEQUENCE: 19

Tyr Ala Thr Tyr Ala Pro Ala Ala Pro Ala Ala Thr Tyr Ala Pro Ala
1               5                   10                  15

Ala Gly Ala Gln Pro Lys Ala Thr Thr Pro Glu Gln Lys Leu Met Glu
                20                  25                  30

Cys Ile Asn Asp Gly Phe Lys Ala Ala Val Ala Ala Ala Ala Gly Val
            35                  40                  45

Pro Pro Ala Asp Lys Tyr Lys Thr Phe Glu Ala Thr Phe Ala Ala Ala
50                  55                  60

Ser Asn Lys Ala Phe Ala Glu Val Leu Lys Gly Ala Ala Thr Gly Gln
65                  70                  75                  80

Ile Ala Gly Gln Ser Ser Met Ala Lys Leu Ser Ser Ser Leu Glu
                85                  90                  95

Leu Ser Tyr Lys Leu Ala Tyr Asp Lys Ala Gln Gly Ala Thr Pro Glu
            100                 105                 110

Ala Lys Tyr Asp Ala Tyr Val Ala Thr Leu Thr Glu Ser Leu Arg Val
            115                 120                 125

Ile Ser Gly Thr Leu Glu Val His Ser Val Lys Pro Ala Ala Glu Glu
130                 135                 140

Val Lys Gly Val Pro Ala Gly Glu Leu Lys Ala Ile Asp Gln Val Asp
145                 150                 155                 160

Ala Ala Phe Arg Thr Ala Ala Thr Ala Ala Asp Ala Pro Ala Asn
                165                 170                 175

Asp Lys Phe Thr Val Phe Glu Ser Ala Phe Asn Lys Ala Ile Lys Glu
            180                 185                 190

Thr Thr Gly Gly Ala Tyr Glu Ser Tyr Lys Phe Ile Pro Ala Leu Glu
            195                 200                 205

Ala Ala Val Lys Gln Ala Tyr Ala Ala Thr Val Ala Ala Ala Pro Glu
            210                 215                 220

Val Lys Phe Thr Val Phe Gln Thr Ala Leu Ser Lys Ala Ile Asn Ala
225                 230                 235                 240

Met Thr Glu Ala Gly Lys Val Ala Asn Pro Val Ala Ala Val Ala Ala
                245                 250                 255

Thr Ala Thr Ala Ala Ala Gly Ala Gly Ala Thr Ala Thr Ala Gly Gly
                260                 265                 270

Tyr Lys Val
        275
```

VARIANTS OF GROUP 5 ALLERGENS OF THE TRUE GRASSES HAVING REDUCED ALLERGENEITY DUE TO MUTAGENESIS OF PROLINE RESIDUES

SEQUENCE LISTING

The instant application contains a Sequence Listing which has been submitted in ASCII format via EFS-Web and is hereby incorporated by reference in its entirety. Said ASCII copy, created on Nov. 15, 2012, is named MERCK397.txt and is 34,834 bytes in size.

AREA OF THE INVENTION

The present invention relates to the preparation and use of recombinant variants of group 5 allergens of the Poaceae (true grasses), which are characterised by reduced IgE reactivity compared with known wild-type allergens and at the same time substantially retained reactivity with T-lymphocytes.

The reduced IgE reactivity is achieved principally by substitution or deletion of certain proline residues, which are strongly preserved in group 5 allergens. In addition, the amino acid proline at position 211 (Phl p 5.0109 numbering) has been recognised as key position for specifically influencing the solubility behaviour of the variants in aqueous formulations.

These hypoallergenic allergen variants can be employed for specific immunotherapy (hyposensitisation) of patients having grass pollen allergy or for the preventative treatment for preventing the development of grass pollen allergies.

A preferred embodiment of the invention relates to variants of the principal allergen Phl p 5 from the pollen of Timothy grass (*Phleum pratense*).

BACKGROUND OF THE INVENTION

Type 1 allergies have worldwide importance. Up to 20% of the population in industrialised countries suffer from complaints such as allergic rhinitis, conjunctivitis or bronchial asthma.

These allergies are caused by sources of various origin, such as trees and grasses (pollen), fungi (spores), mites (excrement), cats or dogs. The allergen sources are released directly into the air (pollen, spores) or can reach the air bonded to diesel soot particles (pollen) or house dust (mite excrement, skin particles, hair). Since the allergy-triggering substances are located in the air, the term aeroallergens is also used.

The type 1 allergy-triggering substances are proteins, glycoproteins or poly-peptides. After uptake via mucous membranes, these allergens react with the IgE molecules bound to the surface of mast cells in sensitised persons. If these IgE molecules are crosslinked with one another by an allergen, this results in the secretion of mediators (for example histamine, prostaglandins) and cytokines by the effector cell and thus in the corresponding allergic symptoms.

Up to 40% of type 1 allergy sufferers exhibit specific IgE reactivity with pollen extracts of true grasses (Burney et al., 1997, J. Allergy Clin. Immunol. 99:314-322; D'Amato et al., 1998, Allergy 53: 567-578; Freidhoff et al., 1986, J. Allergy Clin Immunology, 78, 1190-2002). The family of the true grasses (Poaceae) encompasses more than 10000 species, many more than 20 of which are hitherto known as triggers of allergic symptoms (Andersson & Lidholm, 2003, Int. Arch. Allergy Immunol. 130:87-107; Esch, 2008, Allergens and Allergen Immunotherapy, Clinical Allergy and Immunology Series, 107-126).

Most of the allergy-triggering true grasses belong to the Pooideae sub-family. Besides the grass species occurring as wild forms, such as, for example, *Holcus lanatus* (velvet grass), *Phalaris aquatica* (canary grass), *Anthoxanthum odoratum* (sweet vernal grass), *Dactylis glomerata* (orchard grass), *Festuca pratensis* (meadow fescue), *Poa pratensis* (Kentucky blue grass) or *Lolium perenne* (rye grass), cultivated cereals, such as *Triticum aestivum* (wheat), *Secale cereale* (rye) and *Hordeum vulgare* (barley), are also known members of this sub-family.

One of the Pooideae species which has been investigated best with respect to its allergens is Timothy grass (*Phleum pratense*), which is widespread worldwide as a wild plant and also plays a commercial role as a pasture plant and hardy feed grass.

Depending on the relative frequency in a population with which the individual allergen molecules react with the IgE antibodies of allergy sufferers, a distinction is made between major and minor allergens.

Six allergens of Timothy grass can be regarded as major allergens: Phl p 1 (Petersen et al., 1993, J. Allergy Clin. Immunol. 92: 789-796), Phl p 5 (Matthie-sen and Löwenstein, 1991, Clin. Exp. Allergy 21: 297-307; Petersen et al., 1992, Int. Arch. Allergy Immunol. 98: 105-109), Phl p 6 (Petersen et al., 1995, Int. Arch. Allergy Immunol. 108, 49-54), Phl p 2/3 (Dolecek et al., 1993, FEBS 335 (3): 299-304), Phl p 4 (Haavik et al., 1985, Int. Arch. Allergy Appl. Immunol. 78: 260-268; Valenta et al., 1992, Int. Arch. Allergy Immunol. 97: 287-294; Nandy et al., Biochem. Biophys. Res. Commun., 2005, 337(2): 563-70) and Phl p 13 (Suck et al., 2000, Clin. Exp. Allergy 30: 1395-1402).

The dominant major allergens of Timothy grass are Phl p 1 and Phl p 5 (Andersson & Lidholm, 2003, Int. Arch. Allergy Immunol. 130:87-107), where Phl p 5 occurs in the two forms 5a and 5b, which are encoded by independent genes and differ with respect to their molecular weight. Following the official nomenclature of allergens, Phl p 5a is called Phl p 5.01 and Phl p 5b is called Phl p 5.02 (WHO/IUIS Allergen Nomenclature Subcommittee, www.allergen.org). The amino acid sequences both of Phl p 5a and also of Phl p 5b have been derived from the cloned cDNA sequences. Natural variants of both isoforms have been identified, which differ from one another through point mutations and correspond to different allelic forms (Vrtala et al., 1993, J. Immunol., 151: 4773-4781; Gelhar et al., 1997, Eur. J. Biochem., 247: 217-23). These variants are recorded in the WHO/IUIS database as Phl p 5.01xx and Phl p 5.02xx.

Natural Phl p 5a (nPhl p 5a) is a protein of about 32 kDa and reacts with IgE antibodies of 85-90% of grass pollen allergy sufferers (Rossi et al., 2000, Allergy Int., 49: 93-97).

The pollen of the related true grass species from the Poaceae family and in particular the Pooideae sub-family, such as *Lolium perenne* or *Poa pratensis*, contain allergens which are homologous with Phl p 5 and together are known as group 5 allergens. The high structural homology of these group 5 allergens causes correspondingly high cross-reactivity of the molecules with IgE antibodies (Lorenz et al., 2009, Int. Arch. Immunol. 148:1-17). Finally, this cross-reactivity means that sensitisation by one grass species may be sufficient to trigger an allergic reaction by other related grasses.

The high cross-reactivity of group 5 allergens is ultimately based on a similar primary sequence of the homologous allergens. This is shown by an amino acid sequence comparison of group 5 allergens of selected Pooideae species (FIG. 1).

Besides the cross-reactivity of the group 5 allergens with one another, cross-reactivity of Phl p 5 with another major allergen of Timothy grass is also known (Løwenstein, 1978, Allergy 33: 30-41; Petersen et al., 1995, Int. Arch. Allergy Immunol. 108: 55-59; Blume et al., 2004, Proteomics 4: 1366-71). The polypeptide chain of the allergen Phl p 6 exhibits great similarity with the N-terminal half of the various Phl p 5 sequences (FIG. 1). It is thought that the allergens can be traced back to a common original gene. The similarity between the allergens of the two groups has the effect that some of the Phl p 5-reactive IgE antibodies also bind to Phl p 6 (Petersen et al., 1995, Int. Arch. Allergy Immunol. 108: 49-54; Andersson & Lidholm, 2003, Int. Arch. Allergy Immunol. 130:87-107).

The 3D structure of many allergens has been explained in the past by NMR spectroscopy or X-ray structural analysis and served, inter alia, as the basis for localisation of IgE-binding epitopes on the protein surface. In the case of group 5 allergens of grass pollen, it has hitherto not been possible to generate a model which encompasses the entire polypeptide chain (Rajashankar et al., 2002, Acta Cryst. D58:1175-1181; Maglio et al., 2002, Protein Engineering 15: 635-642).

On the basis of 3D structures of the allergen Phl p 6 (RCSB protein data bank entry: 1NLX) and of a Phl p 5b half-molecule (RCSB protein data bank entry: 1L3P), it has been possible to generate a homology model of Phl p 5a (Wald et al., 2007, Clin. Exp. Allergy 37:441-450). According to this model, Phl p 5a is built up from two helix bundles, but the precise position of the two bundles to one another cannot be explained by the homology model (FIG. 2).

Specific immunotherapy (SIT) or hyposensitisation is regarded as an effective approach to the therapeutic treatment of allergies (Fiebig 1995 Allergo J. 4 (6):336-339, Bousquet et al., 1998, J. Allergy Clin. Immunol. 102 (4): 558-562); Cox et al., 2007, J. Allergy Clin. Immunol. 120:S25-85; James & Durham, 2008, Clin. Exp. Allergy 38: 1074-1088).

The classical therapy form of injection therapy (SCIT), in which natural allergen extracts are injected subcutaneously into the patient in increasing doses, has been used successfully for about 100 years. In this therapy, the immune system of the allergy sufferer is repeatedly confronted with allergens, causing reprogramming of the immune system to be achieved together with tolerance of the allergens. After uptake of the antigens from the allergen preparations by antigen-presenting cells, peptides are presented to the antigens on the cell surface. Some particular peptides which contain so-called T-cell epitopes are recognised by antigen-specific T-cells. This binding results, inter alia, in the development of various types of T-cells having a regulatory function. In the course of SIT, the regulatory T-cell response results in tolerance of the allergen, the downregulation of $T_H2$ cytokines, the restoration of the $T_H1/T_H2$ equilibrium, the suppression of allergen-specific IgE, the induction of IgG4, IgG1 and IgA antibodies, the suppression of effector cells (mast cells, basophils and eosinophils) and the renewal of inflamed tissue (Akdis et al., 2007, J. Allergy Clin. Immunol. 119 (4):780-789; Larchè et al., 2008, Nature Reviews 6:761-771). The T-cell epitopes are thus of crucial importance for the therapeutic action of allergen preparations in the case of hyposensitisation.

Owing to the cross-reactivity of the major allergens of the true grasses which is present at the IgE and also the T-cell level, successful therapy with an allergen extract of a single representative grass species is usually sufficient (Malling et al., 1993, EAACI Position Paper: Immunotherapy, Allergy 48: 9-35; Cox et al., 2007, J Allergy Clin Immunol 120: 25-85).

Besides subcutaneous immunotherapy, a sublingual therapy form, in which the allergens or allergen derivatives are taken up via the oral mucous membrane, is undergoing clinical trials and use as an alternative to injection therapy (James & Durham, 2008, Clin. Exp. Allergy 38: 1074-1088).

A further possibility is treatment with expressible DNA which encodes for the relevant allergens (immunotherapeutic vaccination). Experimental evidence of the allergen-specific influencing of the immune response has been furnished in rodents by injection of allergen-encoding DNA (Hsu et al. 1996, Nature Medicine 2 (5):540-544, Weiss et al., 2006, Int. Arch. Allergy Immunol. 139: 332-345).

In all these therapy forms, there is a fundamental risk of allergic reactions or even anaphylactic shock (Kleine-Tebbe, 2006, Allergologie, 4:135-156). In order to minimise these risks, innovative preparations in the form of allergoids are employed. These are chemically modified allergen extracts which have significantly reduced IgE reactivity, but identical T-cell reactivity compared with the untreated extract (Fiebig 1995 Allergo J. 4 (6):336-339, Kahlert et al., 1999, Int. Arch. Allergy Immunol, 120: 146-157).

Therapy optimisation is possible with allergens prepared by recombinant methods. Defined cocktails of high-purity allergens prepared by recombinant methods, which are optionally matched to the individual sensitisation patterns of the patients, could replace extracts from natural allergen sources, since, apart from the various allergens, the latter contain a relatively large number of immunogenic, but non-allergenic accompanying proteins. Initial clinical studies with recombinant allergens have already been carried out with success (Jutel et al., 2005, J. Allergy Clin. Immunol., 116: 608-613; Valenta & Niederberger, 2007, J. Allergy Clin. Immunol. 119: 826-830).

Realistic prospects which may result in safe hyposensitisation with recombinant expression products are offered specifically by mutated recombinant allergens in which IgE epitopes are modified without impairing the T-cell epitopes which are essential for the therapy (Schramm et al. 1999, J. Immunol. 162:2406-2414). These hypoallergenic proteins could be employed in relatively high doses during SIT without increasing the probability of undesired IgE-promoted side effects.

In the past, such "hypoallergenic" variants with reduced IgE binding have been published for many aeroallergens (inter alia pollen and house dust mite allergens) and food allergens. On the basis of the DNA of unmodified allergens, it has been possible to prepare and express a recombinant DNA, inter alia by fragmentation, oligomerisation, deletions, point mutations or recombination of individual sections of an allergen (DNA shuffling) (Ferreira et al., 2006, Inflamm. & Allergy—Drug Targets 5: 5-14; Bhalla & Singh, 2008, Trends in Biotechnology 26:153-161).

With respect to grass pollen allergens, hypoallergenic variants of groups 1, 2, 5a, 5b, 6, 7 and 12 have been described (Ferreira et al., 2006, Inflamm. & Allergy—Drug Targets 5: 5-14; Westritschnig et al., 2007, J. Immunol. 179: 7624-7634).

A number of publications have to date described approaches to the development of hypoallergenic group 5 allergens. For Phl p 5a and Phl p 5b, it has been shown that the combined deletion of two sequence sections results in a considerable reduction in IgE binding and reduced ability to stimulate basophilic effector cells. However, the T-cell reactivity of the deletion mutants was modified slightly compared with that of the unmodified allergen (Schramm et al., 1999, J. Immunol. 162: 2406-2414; Wald et al., 2007, Clin. Exp. Allergy 37:441-450).

In another paper, the group 5 allergen from *Lolium perenne* (Lol p 5) was modified by amino acid substitutions and/or short deletions at the C terminal (Swoboda et al., 2002, Eur. J. Immunol. 32: 270-280). The mutations were not restricted to a particular amino acid type. The substituted amino acids were lysine, phenylalanine, threonine, valine or alanine. The conceptional approach of generating hypoallergenic mutants by specific mutation of a number of residues of an individual amino acid has likewise been described. Gelhar et al. described the generation of a recombinant Phl p 5b fragment by substitution of ten lysine residues localised at the protein surface by alanine (Gelhar et al., 2006, Int. Arch. Allergy Immunol. 140:285-294). However, a mutation strategy based on point mutations in proline residues has hitherto not been published for group 5 grass pollen allergens.

The object on which the present invention is based consisted in the provision of novel recombinant variants of group 5 allergens of the Poaceae at the protein and DNA level which are distinguished by reduced IgE reactivity at the same time as substantial retention of the T-cell reactivity and are therefore suitable for curative and preventive specific immunotherapy and immunotherapeutic DNA vaccination.

DESCRIPTION OF THE INVENTION

Surprisingly, it has been found that variants of group 5 allergens of the true grass family (Poaceae) in which the prolines which correspond in an alignment to the prolines in positions 57, 58, 117, 146, 155, 211, 229 in the amino acid sequence of wild-type Phl p 5.0109 have mutated singly or in combinations, have reduced IgE reactivity compared with the wild-type allergens and at the same time have substantially retained reactivity with T-lymphocytes and are thus hypoallergenic.

The invention accordingly relates to hypoallergenic variants of group 5 allergens of the true grass family (Poaceae) in which the prolines which correspond in an alignment to the prolines in positions 57, 58, 117, 146, 155, 211, 229 in the amino acid sequence of wild-type Phl p 5.0109 have mutated singly or in combinations.

Particular preference is given to allergen variants according to the invention, characterised in that the prolines have been deleted or substituted.

Preference is given to hypoallergenic variants according to the invention of group 5 allergens from the Pooideae sub-family, preferably from the groups Poodae and Triticodae, preferably represented by *Phleum pratense, Holcus lanatus, Phalaris aquatica, Anthoxanthum odoratum, Dactylis glomerata, Lolium perenne, Poa pratensis, Festuca pratensis, Hordeum vulgare, Secale cereale* and *Triticum aestivum*. They are preferably hypoallergenic variants according to the invention of Tri a 5, Sec c 5 and Hor v 5 from *Triticum aestivum, Secale cereale* and *Hordeum vulgare*. Particular preference is given to hypoallergenic variants according to the invention of group 5 allergens of the Poodae. These group 5 allergens are preferably Poa p 5, Dac g 5, Hol p 5, Lol p 5 and Pha a 5 from *Poa pratensis, Dactylis glomerata, Holcus lanatus, Lolium perenne* and *Phalaris aquatica* and very particularly preferably Phl p 5 from *Phleum pratense*. All naturally occurring isomers, polymorphs and variants of the above-mentioned allergens, and precursor proteins thereof, are also in accordance with the invention.

In the hypoallergenic variants according to the invention, the mutated prolines are preferably those which correspond in an alignment (FIG. 1a) to the prolines in positions 57, 58, 117, 146, 155, 211 or 229 in the amino acid sequence of ripe Phl p 5.0109 (Phl p 5 a, UniProtKB entry: Q84UI2) FIGS. 3 and 4, SEQ ID NO:1, SEQ ID NO:2) or variants thereof (FIG. 1b) or of ripe Phl p 5.0201 (Phl p5 b; Swiss-Prot: Q40963.2; FIG. 24, SEQ ID NO: 5) or variants thereof (FIG. 1b), particularly preferably of ripe Phl p 5.0109.

Although it was known that prolines can exert an influence on the protein structure, specific point mutations of proline residues as starting point for the generation of hypoallergenic mutants of allergens were merely investigated for the group 2 principal allergen of the house dust mite *Dermatophaogides farinae* (Der f 2, replacement of proline residues by alanine) (Takai et al., 2000, Eur. J. Biochem. 267: 6650-6656). However, the IgE binding ability and ability to stimulate basophilic cells was only slightly reduced in the case of three point mutants, while the other three behaved like the unmodified allergen. The proline mutations in the case of Der f 2 thus exhibited an only very weak reduction in allergeneity, or none at all. Further strategies for the preparation of hypoallergenic mutants by proline exchange mutations have not been published. Thus, the person skilled in the art would not have expected proline mutations to be successful as starting point for the generation of hypoallergenic mutants of allergens.

In addition, it has hitherto not been investigated for any allergen how a specific deletion of proline residues affects the entire IgE binding ability of the expression product and what effects occur on the activation of allergy-relevant effector cells.

The amino acid sequence of Phl p 5.0109 (UniProtKB: Q84UI2) contains 16 proline residues (FIG. 1). The six proline residues P7, P10, P13, P19, P22 and P27 are localised in the N-terminal region, which is preserved to a low extent within the group 5 allergens. The prolines in amino acid positions 57, 58, 85, 117, 146, 155, 211, 229 and 256 are located at the beginning or end of α-helices or in loops which connect the α-helices and are strongly preserved apart from amino acid P85 (FIG. 1, 2).

Starting from the amino acid sequence of the Phl p 5a isoform Phl p 5.0109, the recombinant unmodified wild-type allergen (rPhl p 5a wt; FIG. 4, SEQ ID NO:2) and variants modified by genetic engineering are prepared. Analogously to the preparation process described below, the wild-type proteins and the hypoallergenic variants according to the invention of the other group 5 allergens according to the invention of the true grasses, for example Lol p 5; Poa p 5, Pha a 5, Dac g 5; Hol l 5, Tri a 5 and Hor v 5, can also be prepared. To this end, the prolines which correspond in an alignment to the prolines in positions in positions 57, 58, 117, 146, 155, 211, 229 in the amino acid sequence of wild-type Phl p 5 have mutated singly6 or in combinations, preferably by substitution or deletion.

In addition to the variations described of group 5 allergens, further modifications at other positions—for example in order to increase the hypoallergeneity—are naturally also possible. These modifications can be, for example, amino acid insertions, deletions, replacements and cleavages of the protein into fragments and fusions of the protein or fragments thereof with other proteins or peptides, and multimers through fusions of identical proteins or fragments.

Fragments according to the invention preferably comprise 20-109 amino acids, preferably 30-100 amino acids, particularly preferably 40-90 amino acids. Variants according to the invention additionally include precursor proteins, such as, for example, ProPhl p 5, with a prior natural or artificial signal sequence. Also in accordance with the invention are fusion proteins having N- or C-terminal fusion tags (for example His tag, as in FIGS. 5 and 6, MBP tag, expression control sequences, etc.), hybrid molecules, such as, for example, fusions with other allergens or hypoallergenic variants thereof or fusions of fragments in any desired sequence. In addition, the variants according to the invention also comprise homologous sequences (polymorphs (SNPs), isoforms) having an identity of the amino acid sequence of at least 80% with the relevant group 5 wild-type allergen, preferably of at least 90% with the relevant group 5 wild-type allergen, particularly preferably of at least 95% with the relevant group 5 wild-type allergen. In these variants, one or a few amino acids are preferably replaced conservatively, for example a polar amino acid is substituted by another polar amino acid or a neutral amino acid is substituted by another neutral amino acid, but variants due to non-conservative replacement are also in accordance with the invention. Multimers preferably include dimers or trimers of the hypoallergenic variants according to the invention connected by a linker sequence or subjected to direct fusion.

Examples of isoforms are the allergens Phl p 5a and Phl p 5b, in which individual amino acids which are not relevant for the action according to the invention have been replaced, or in which regions in the amino acid sequence are missing or have been added (see FIG. 1a). These wild-type allergen isoforms have, for example, an identity of the amino acid sequence of 63%-71%. Further examples of variants according to the invention are variants of the wild-type allergen isoforms Phl p 5a and Phl p 5b, such as, for example, Phl p 5.0109, Phl p 5.0201, Phl p 5.0204, Phl p 5.0206, Phl p 5.0207 and the like, and further variants with replacement of one or more amino acids, omission of one or more amino acids at the N- and/or C-terminal or with corresponding deletion gaps within the amino acid sequence. Likewise in accordance with the invention are variants with insertions of single or multiple amino acids individually at various positions or as a group at a position within the amino acid sequence or at the N and/or C terminal.

The invention thus also relates to hypoallergenic variants of group 5 allergens of the true grasses (Poaceae), characterised in that it is a fragment or a variant of a hypoallergenic variant according to the invention or a multimer of one or more hypoallergenic variants according to the invention or characterised in that one or more hypoallergenic variants according to the invention or fragments, variants or multimers thereof are a constituent of a recombinant fusion protein.

In addition, the invention relates to a DNA molecule which encodes for a hypoallergenic variant according to the invention.

The invention furthermore relates to a recombinant expression vector containing a DNA molecule according to the invention of this type functionally connected to an expression control sequence. An expression control sequence is taken to mean, for example, a promoter or a sequence section with the aid of which the expression of the target protein is influenced and which is functionally connected to the target gene, but does not necessarily have to be localised in the direct vicinity of the target gene.

The invention also relates to a non-human host organism transformed by means of a DNA molecule according to the invention or an expression vector according to the invention.

The invention relates to a process for the preparation of a hypoallergenic variant according to the invention by cultivation of a non-human host organism according to the invention and isolation of the corresponding allergen variant from the culture.

Suitable non-human host organisms can be pro- or eukaryotic, single- or multicelled organisms, such as bacteria or yeasts. A host organism which is preferred in accordance with the invention is *E. coli*.

The influence of the deletion of single or of two closely adjacent prolines on the IgE binding ability of Phl p 5a can be investigated by deletion of prolines 57+58, of proline 85, proline 117, proline 146+155, proline 180, proline 221, proline 229 and of proline 256. In the Phl p 5 wild-type protein, these prolines are localised in the loop regions at the beginning or end of α-helices (FIG. 3). The influence of proline mutations in the corresponding homologous positions of the other group 5 allergens according to the invention of the true grasses, for example Poa p 5 and Lol p 5, on the IgE binding ability can be investigated analogously.

For faster high-yield purification, the encoding DNA for these investigations is provided with a sequence encoding for an N-terminal hexahistidine (SEQ ID NO: 6) fusion component (+6His ("6His" disclosed as SEQ ID NO: 6)) (FIG. 5, SEQ ID NO:3; FIG. 6, SEQ ID NO:4). The tag-free variants according to the invention and wild-type proteins which can be employed for pharmaceutical purposes are likewise purified by standard methods and confirm the results of the His-tag proteins.

Sequences encoding for the proteins rPhl p 5a d[P57, P58]+6His, rPhl p 5a d[P85]+6His, rPhl p 5a d[P117]+6His, rPhl p 5a d[P146, P155]+6His, rPhl p 5a d[P180]+6His, rPhl p 5a d[P211]+6His, rPhl p 5a d[P229]+6His and rPhl p 5a d[P256]+6His are prepared correspondingly ("6His" disclosed as SEQ ID NO: 6). The sequences can be expressed in all known eukaryotic and prokaryotic expression systems, preferably in *E. coli*. The proteins are subsequently purified as soluble monomers by standard methods. Finally, purity can be checked by analysis in a denaturing polyacrylamide gel (SDS-PAGE).

Analytical gel filtration (SEC) with coupling of a refractometer (RI detector) and a multiangle light-scattering detector (MALS detector) allows online determination of the molecular weight of the eluted proteins (SEC/MALS/RI method).

The recombinant variants according to the invention can, in addition, be investigated with respect to their binding ability to human IgE antibodies by IgE inhibition tests (EAST). In this method, the allergen/IgE interaction can be investigated in solution, which enables interfering masking of epitopes of the test substance, for example due to immobilisation on a membrane, to be excluded.

Reduced IgE binding of the mutants rPhl p 5a d[P57, P58]+6His, rPhl p 5a d[P117]+6His, rPhl p 5a d[P146, P155]+6His, rPhl p 5a d[P180]+6His, rPhl p 5a d[P211]+6His and rPhl p 5a d[P229]+6His can be observed compared with the unmodified rPhl p 5a wt (FIG. 7) ("6His" disclosed as SEQ ID NO: 6).

This basically proves that the deletion of proline residues from group 5 allergens reduces the IgE binding ability of these allergens. On the other hand, only the deletion of certain prolines results in reduced IgE binding.

The present invention therefore furthermore relates to hypoallergenic variants of group 5 allergens of the true grass family (Poaceae) in which the prolines which correspond in an alignment to the prolines in positions 57, 58, 117, 146, 155, 211 or 229 in the amino acid sequence of wild-type Phl p 5.0109 have mutated singly.

The present invention preferably relates to hypoallergenic variants of Phl p 5, Poa p 5, Lol p 5, Dac g 5, Hol l 5, Pha a 5 in which the prolines which correspond in an alignment to the prolines in positions 57, 58, 117, 146, 155, 211 or 229 in the amino acid sequence of wild-type Phl p 5.0109 have mutated singly.

The present invention particularly preferably relates to hypoallergenic variants of Phl p 5 in which the prolines which correspond in an alignment to the prolines in positions 57, 58, 117, 146, 155, 211 or 229 in the amino acid sequence of wild-type Phl p 5.0109 have mutated singly.

The present invention furthermore preferably relates to hypoallergenic variants according to the invention of group 5 allergens of the true grass family (Poaceae) in which the prolines which correspond in an alignment to the prolines in positions 57, 58, 117, 146, 155, 211 or 229 in the amino acid sequence of wild-type Phl p 5.0109 have been removed singly.

In addition, the present invention furthermore relates to hypoallergenic variants according to the invention of group 5 allergens of the true grass family (Poaceae) in which the prolines which correspond in an alignment to the prolines in positions 57, 58, 117, 146, 155, 211 or 229 in the amino acid sequence of wild-type Phl p 5.0109 have been substituted individually. Here, proline is replaced by way of example by leucine (L). In accordance with the invention, however, the prolines according to the invention can be replaced by any amino acid.

In particular, the hypoallergenic variants rPhl p 5a d[P57], rPhl p 5a d[P58], rPhl p 5a d[P57, P58], rPhl p 5a d[P117], rPhl p 5a d[P146], rPhl p 5a d[P155], rPhl p 5a d[P146, P155], rPhl p 5a d[P180], rPhl p 5a d[P211], rPhl p 5a d[P229], rPhl p 5a P57L, rPhl p 5a P58L, rPhl p 5a P57, P58L, rPhl p 5a P117L, rPhl p 5a P146L, rPhl p 5a P155L, rPhl p 5a P146L, P155L, rPhl p 5a P180L, rPhl p 5a P211 L and rPhl p 5a P229L, and the like, including all hypoallergenic variants according to the invention described below, are in accordance with the invention, where the numbering follows the sequence of Phl p 5.0109.

Furthermore, these examples are not restricted to variants of Phl p 5a, but also relate, in particular, to Phl p 5b, Poa p 5, Hol l 5, Pha a 5, Ant o 5, Dac g 5, Lol p 5, Fes p 5, Hor v 5, Sec c 5, Tri a 5 and the group 5 allergens of all other true grasses. Corresponding variants of Poa p 5, Lol p 5, Dac g 5, Hol l 5, Pha a 5 and Phl p 5b should be particularly emphasised.

Surprisingly, variants with combinations of deletions from the group of mutations d[P57, P58], d[P117], d[P146, P155], d[P180], d[P211] and d[P229] exhibit significantly more reduced IgE binding ability in the EAST method, as shown for the example of variant rPhl p 5a d[P117, 180]+ 6His ("6His" disclosed as SEQ ID NO: 6) (FIG. 8).

The present invention therefore furthermore relates to hypoallergenic variants of group 5 allergens of the true grass family (Poaceae) in which the prolines which correspond in an alignment to the prolines in positions 57, 58, 117, 146, 155, 180, 211, 229 in the amino acid sequence of wild-type Phl p 5.0109 have mutated in combinations. Preference is given to mutations through deletion and through substitution by other amino acids. Any amino acid can be selected here for replacement by proline.

The present invention preferably relates to hypoallergenic variants of Phl p 5, *Poa p 5*, Lol p 5, Dac g 5, Hol l 5, Pha a 5 in which the prolines which correspond in an alignment to the prolines in positions 57, 58, 117, 146, 155, 180, 211, 229 in the amino acid sequence of wild-type Phl p 5.0109 have mutated in combinations.

The present invention particularly preferably relates to hypoallergenic variants of Phl p 5 in which the prolines which correspond in an alignment to the prolines in positions 57, 58, 117, 146, 155, 180, 211, 229 in the amino acid sequence of wild-type Phl p 5.0109 have mutated in combinations.

These examples are furthermore not restricted to variants of Phl p 5, but also relate, in particular, to Poa p 5, Hol l 5, Pha a 5, Ant o 5, Dac g 5, Lol p 5, Fes p 5, Hor v 5, Sec c 5, Tri a 5 and the group 5 allergens of all other true grasses. Corresponding variants of Phl p 5a, Phl p 5b, Poa p 5, Lol p 5, Dac g 5, Hol l 5, Pha a 5 should be particularly emphasised.

Particular preference is given to hypoallergenic variants according to the invention in which prolines 57, 58, 117, 146, 155, 180, 211, 229 have been removed in combinations. Particular preference is also given to hypoallergenic variants according to the invention in which prolines 57, 58, 117, 146, 155, 180, 211, 229 have been substituted in combinations.

In addition, particular preference is given to hypoallergenic variants according to the invention in which prolines 57, 58, 117, 146, 155, 180, 211, 229 have been removed and/or substituted in combinations. Hypoallergenic variants rPhl p 5a d[57, 58, 117], rPhl p 5a d[57, 58, 146], rPhl p 5a d[57, 58, 150], rPhl p 5a d[57, 58, 180], rPhl p 5a d[57, 58, 211], rPhl p 5a d[57, 58, 229], rPhl p 5a d[117, 146, 155], rPhl p 5a d[117, 146, 155, 180], rPhl p 5a d[117, 146, 155, 229], rPhl pa 5 P117L, P146L, P155L, P211L, rPhl p 5a d[117, 180, 229] P211 L, rPhl p 5a d[117, 180, 229] P211 L, rPhl p 5a d[57, 58, 117, 180, 229] P211 L and the like, including all hypoallergenic variants according to the invention described below, for example, are therefore in accordance with the invention, where the numbering follows the sequence of Phl p 5.0109.

Here, proline is replaced by way of example by leucine (L). In accordance with the invention, however, the prolines according to the invention can be replaced by any amino acid. Accordingly, all hypoallergenic variants mentioned or conceivable in which one or more prolines according to the invention have been substituted by another amino acid are in accordance with the invention. Furthermore, these examples are not restricted to variants of Phl p 5, but also relate, in particular, to Phl p 5b, Poa p 5, Hol l 5, Pha a 5, Ant o 5, Dac g 5, Lol p 5, Fes p 5, Hor v 5, Sec c 5, Tri a 5 and the group 5 allergens of all other true grasses. However, particular preference is given to all mentioned hypoallergenic variants according to the invention of *Phleum pratense* Phl p 5a and Phl p 5b, in particular based on Phl p 5.0109.

On the basis of this knowledge, variants rPhl p 5a d[P57, P58, P85, P117, P146, P155, P180, P211, P229, P256]+6His (short form: MPV.1+6His) and rPhl p 5a d[P57, P58, P117, P146, P155, P180, P211, P229]+6His (short form: MPV.2+ 6His) which contain the largest possible number of combined deletions can be prepared ("6His" disclosed as SEQ ID NO: 6).

When they are expressed, these proteins are deposited in the *E. coli* cells as insoluble aggregates (inclusion bodies). Inclusion bodies are usually solubilised in denaturing agents, such as 6-8 molar guanidinium hydrochloride or urea solution, and later converted into a non-denaturing aqueous solution. This conversion into a non-denaturing solvent environment represents a crucial step in protein purification.

In general, only proteins which behave in a soluble manner after this process can be included in end formulations of therapeutic agents. An industrially used routine method for the conversion of the denatured solubilised proteins into the aqueous solvent is the method of "rapid dilution". In this method, the proteins dissolved in a denaturing agent are added to a large volume of the non-denaturing solvent, with the denaturing agent being highly diluted.

The solubility behaviour of the mutants described here can be investigated systematically. In this investigation, the inclusion bodies prepared in E. coli and dissolved in guanidinium hydrochloride are diluted in ten different aqueous buffered solutions, and the degree of solubility is subsequently determined by UV-Vis spectroscopy.

In the UV-Vis spectroscopy, an absorption spectrum of the protein solution is recorded in the wavelength range from 240-800 nm. Insoluble aggregates in protein solutions absorb in the wavelength range >300 nm, while highly soluble proteins do not absorb in this range.

The test solutions cover a broad pH range (4.5-9.0) and in some cases comprise stabilising additives. The additives glycerol, Tween 80 and L-arginine monohydrochloride are very often employed as aid in the solubilisation of recombinant proteins which are difficult to prepare. They represent the three most important groups of such co-solvents: glycerol as polyalcohol, Tween as nonionic surfactant and L-arginine monohydrochloride as amino acid derivative.

Although variants MPV.1+6His and MPV.2+6His ("6His" disclosed as SEQ ID NO: 6) can be solubilised through the use of the denaturing agent guanidinium hydrochloride, the systematic investigation of the solubility shows, however, that subsequent conversion of the proteins into a guanidinium hydrochloride-free formulation is always accompanied by the formation of insoluble protein aggregates and is thus not possible (Table 1, 2).

During the PCR experiments carried out for the DNA synthesis, a DNA encoding for the protein rPhl p 5a d[P57, P58, P229] K61E, E205K, P211 L+6His (short form: MPV.3+6His) ("6His" disclosed as SEQ ID NO: 6) is formed in the present example through a plurality of polymerase errors. This DNA is likewise expressed in E. coli. Like the variants MPV.1 and MPV.2, the protein is deposited as inclusion bodies in the E. coli cell.

However, the protein MPV.3+6His ("6His" disclosed as SEQ ID NO: 6) can, surprisingly, easily be converted into a non-denaturing buffer solution (Table 3).

EAST-IgE inhibition tests show significantly reduced binding ability of the protein to IgE antibodies compared with variants rPhl p 5a d[P57, P58]+6His and rPhl p 5a d[P229]+6His ("6His" disclosed as SEQ ID NO: 6), which have proline deletions in only one loop (FIG. 9).

For further characterisation of mutations K61E, E205K and P211 L of variant MPV.3+6His, the DNA of the three variants rPhl p 5a K61E+6His, rPhl p 5a E205K+6His and rPhl p 5a P211 L+6His are prepared and investigated in the EAST ("6His" disclosed as SEQ ID NO: 6). All three mutants exhibit slightly reduced IgE binding ability, which indicates a synergistic influence of all mutations on the reduced allergeneity of MPV.3+6His ("6His" disclosed as SEQ ID NO: 6) (FIG. 10). Both the deletion and also the replacement of proline 211 shows a significantly greater individual effect than mutations K61E or E205K (FIG. 10).

By means of a test with basophilic granulocytes isolated from the whole blood of grass pollen allergy sufferers, the effect of the reduced IgE binding ability of MPV.3+6His ("6His" disclosed as SEQ ID NO: 6) on the activation of human effector cells is investigated in vitro. At the same concentration of rPhl p 5a wt and of MPV.3+6His ("6His" disclosed as SEQ ID NO: 6), the latter exhibits lower activation of basophilic granulocytes. This indicates functionally reduced allergeneity of MPV.3+6His ("6His" disclosed as SEQ ID NO: 6) (FIG. 11).

The variant MPV.3+6His ("6His" disclosed as SEQ ID NO: 6) DNA generated randomly now serves as starting point for the targeted construction of further variants. The high solubility of MPV.3+6His ("6His" disclosed as SEQ ID NO: 6) should be retained and the IgE binding ability should be reduced further by the insertion of additional proline mutations.

Firstly, the DNA of variants rPhl p 5a d[P57, P58, P117, P146, P155, P180, P229] K61E, E205K, P211 L (short form: MPV.4) and rPhl p 5a d[P57, P58, P117, P180, P229] K61E, E205K, P211L (short form: MPV.5) is prepared. This DNA is constructed both with and without histidine fusion component and expressed in E. coli. The proteins can be purified as soluble proteins from the inclusion bodies of E. coli cells by a simple purification procedure.

Figure 12:
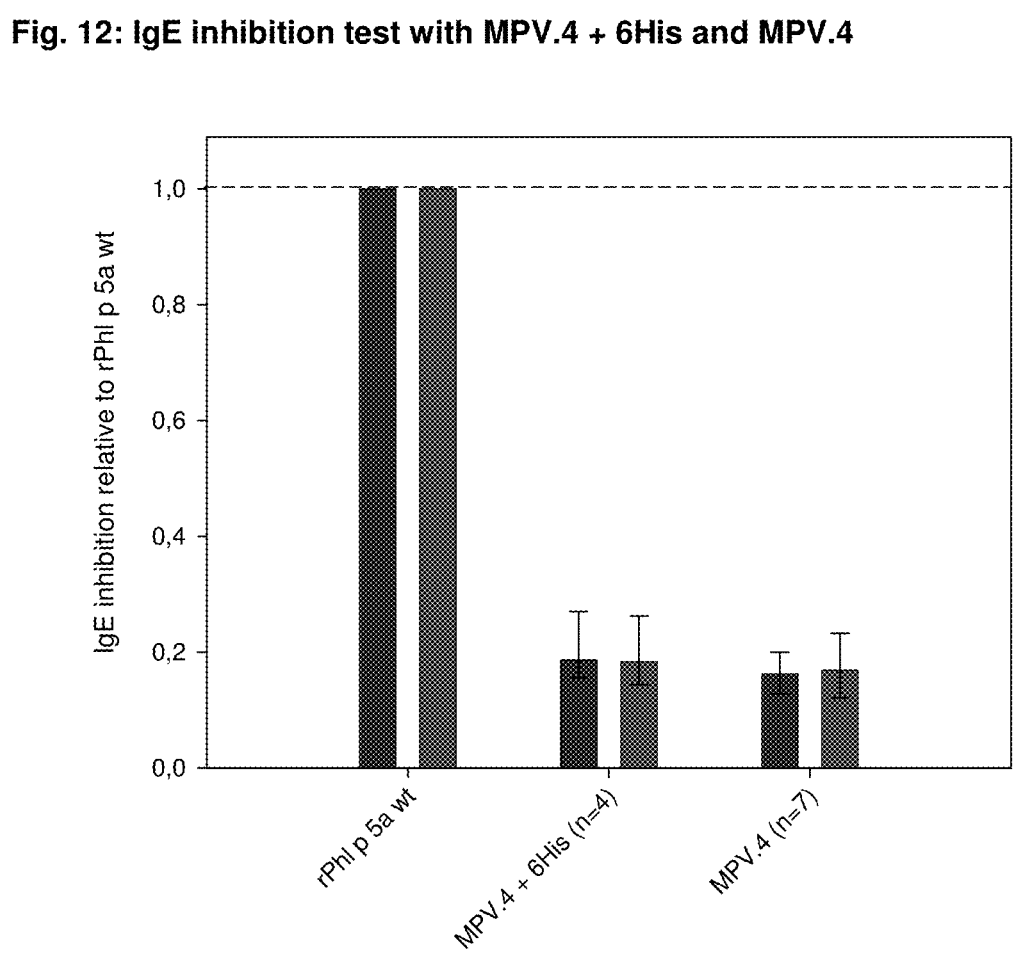

Since both the proteins with and also without fusion component can be purified in a soluble manner, the solubility is not dependent on the presence of the histidine fusion component. The histidine fusion component likewise has no influence on the IgE binding ability, as shown by IgE inhibition tests with proteins with and without fusion component (FIG. 12).

The DNA of variants rPhl p 5a d[P57, P58, P117, P146, P155, P180, P229] P211L (short form: MPV.6) and rPhl p 5a d[P57, P58, P117, P180, P229] P211 L (short form: MPV.7) are generated exclusively without fusion components and expressed in E. coli. They can likewise be purified as highly soluble proteins from inclusion bodies by a simple purification procedure.

Variant MPV.6 differs from variant MPV.2 only through the modification at position 211. Instead of the deletion of P211, MPV.6 contains an amino acid exchange to leucine. The extremely different solubility behaviour is thus directly dependent on position 211. All mutants which carry mutation P211 L (MPV.3-MPV.7) are distinguished by high solubility in various aqueous formulations, whereas the mutants with a deletion at position 211 remain insoluble (Table 1-Table 5).

The present invention therefore relates to hypoallergenic variants according to the invention of group 5 allergens of the true grasses in which the proline residue of amino acid position 211 corresponding to ripe Phl p 5.0109 is not deleted, but instead is replaced by another amino acid.

The present invention therefore relates to hypoallergenic variants according to the invention of group 5 allergens of the true grasses in which the proline residue which corresponds in an alignment to proline 211 in the amino acid sequence of wild-type Phl p 5 or ripe Phl p 5.0109 is not deleted, but instead is replaced by leucine.

In analytical gel filtration (SEC), protein species are not separated exclusively in accordance with their molecular weight (molar mass); the conformation, the specific hydrodynamic radius and possible interactions with the matrix likewise play an important role here. A true online determination of the molecular weight can be achieved by coupling of a refractometer (RI detector) and a multiangle light-scattering detector (MALS detector) to the SEC chromatography system (SEC/MALS/RI method). The particle concentration given at the measurement time is determined by the RI detector here, and the light scattering by the particle is recorded by the MALS detector (Wen et al., 1996, Anal.

Biochem. 240:155-166). Monomers, dimers, multimers and aggregates can be detected unambiguously by SEC/MALS/RI.

The result of the SEC/MALS/RI of MPV.5 and MPV.7 shows that these variants are in pure form and in the form of soluble monomers (FIG. 13; FIG. 14; Table 6). The two variants MPV.4 and MPV.6 are in each case detected as a mixture of soluble monomers and dimers (FIG. 15; FIG. 16; Table 6). Variants MPV.5 and MPV.7 differ from variants MPV.4 and MPV.6 in each case only at position 146 and 155. Prolines P146 and P155 are present in MPV.5 and MPV.7. This shows that deletion d[P146, P155] causes a strong tendency towards dimerisation of the corresponding variants.

The IgE binding ability of the optimised variants MPV.4 to MPV.7 is firstly investigated by a method in which the proteins are immobilised on a nitrocellulose membrane and incubated with sera of individual grass pollen allergy sufferers comprising IgE antibodies. The allergen variant/antibody complexes are subsequently stained by an enzymatic reaction. In this method, very greatly reduced IgE binding ability of all four proteins is apparent (FIG. 17).

This result is confirmed by an EAST-IgE inhibition test with a representative human allergy sufferer serum pool, where variants MPV.4 and MPV.6 have IgE binding which is in each case somewhat lower than the corresponding mutants MPV.5 and MPV.7 without mutation d[P146, P155] (FIG. 18; FIG. 19).

The lower IgE binding if mutation d[P146, P155] is present can probably be ascribed to the dimerisation tendency of these variants, which possibly results in masking of IgE epitopes at the contact areas of the dimerisation partners.

The test results for activation of basophilic granulocytes show functionally greatly reduced allergeneity for all four variants (FIG. 20; FIG. 21; FIG. 22; FIG. 23).

The present invention therefore relates to hypoallergenic variants according to the invention of group 5 allergens of the true grasses, characterised in that the proline which corresponds in an alignment to proline 211 of wild-type Phl p 5.0109 is not deleted, but instead is replaced by another amino acid.

The invention thus preferably also relates to hypoallergenic variants according to the invention of group 5 allergens of the true grasses in which the prolines which correspond in an alignment to the prolines at positions 57, 58, 117, 180 and 229 in the amino acid sequence of wild-type Phl p 5.0109 have mutated singly or in combinations, has preferably been deleted, and proline 211 has been replaced by leucine.

The invention thus preferably also relates to hypoallergenic variants according to the invention of group 5 allergens of the true grasses in which the prolines which correspond in an alignment to the prolines at positions 57, 58 and 229 in the amino acid sequence of wild-type Phl p 5.0109 have been deleted and proline 211 has been replaced by leucine.

The present invention accordingly also relates to hypoallergenic variants according to the invention in which the prolines which correspond in an alignment to the prolines at positions 146 and 155 in the amino acid sequence of wild-type Phl p 5.0109 are not mutated. These are preferably in the form of the monomer.

Also in accordance with the invention are all abovementioned hypoallergenic variants according to the invention in which, in addition, the amino acids which correspond in an alignment to lysine at position 61 and glutamic acid at position 205 in the amino acid sequence of wild-type Phl p 5 have mutated singly or in combinations. These amino acids have preferably been substituted.

The T-cell reactivity on which the efficacy of specific immunotherapy is based is checked in vitro by a proliferation test with Phl p 5-specific T-lymphocytes of grass pollen allergy sufferers. The results of allergen variants MPV.4 and MPV.7 are described here by way of example. The dimerising variant MPV.4 carries all mutations (d[P57, P58, P117, P146, P155, P180, P229] K61E, E205K, P211L) investigated here and thus represents a molecule having an amino acid sequence which has been modified to the maximum. Mutant MPV.7 is selected as an example of a monomeric form with pure proline mutations. Both mutants exhibit a T-cell reactivity which is comparably good to the unmodified allergen (Table 7; Table 8). The retention of the crucial T-cell epitopes enables immunotherapeutic use of the variants described.

T-helper lymphocytes react with peptide fragments of the allergens which form through degradation processes in antigen-presenting cells (APCs) and are presented bound to MHC class II molecules at the surface of the APCs. The peptides generally have a length of 13-18 amino acids, but may also be longer owing to the MHC class 2 binding site which is open laterally. The principal contact points of the peptide with the MHC class molecule are to be found in a core sequence of about 7-10 amino acids. The allergen-specific activation of the T-helper lymphocytes is the prerequisite for proliferation and functional differentiation thereof (for example Treg, $T_H1$ and $T_H2$). The ability of an allergen or allergen variant to stimulate allergen-specific T-lymphocytes is regarded as a key for therapeutic efficacy thereof.

All allergen variants produced on the basis of Phl p 5 or Phl p 5.0109 and described here exhibit substantial retention of crucial T-cell epitopes in experiments.

Thus, variants of group 5 allergens of the Poaceae which have novel protein properties through the modification of proline residues are described for the first time. The proline residues concerned are localised in loop regions. Only the modification of certain proline residues results in the novel variants, which are distinguished by reduced IgE reactivity with substantial retention of the T-cell reactivity and are therefore suitable for curative and preventive specific immunotherapy. Corresponding DNA molecules are suitable for immunotherapeutic vaccination.

The present invention therefore relates to the described allergen variants, DNA molecules and recombinant expression vectors according to the invention as medicaments.

Hypoallergenic variants, DNA molecules and recombinant expression vectors according to the invention or medicaments according to the invention can be used, in particular, for the prophylaxis and/or for the treatment of diseases and conditions. Medicaments according to the invention are particularly suitable for the treatment and/or prophylaxis of type 1 allergies, i.e. for the specific immunotherapy (hyposensitisation) of patients having grass pollen allergy or for the preventive immunotherapy of grass pollen allergies in the triggering of which group 5 allergens of Poaceae species are involved. DNA molecules and recombinant expression vectors according to the invention can be employed for corresponding immunotherapeutic and -prophylactic DNA vaccination.

The invention also relates to the use of at least one hypoallergenic variant according to the invention for the preparation of a medicament for the prevention and/or therapeutic treatment of type 1 allergies in the triggering of which group 5 allergens of the true grasses are causally involved.

Also in accordance with the invention is the use of at least one DNA molecule according to the invention and/or a recombinant expression vector according to the invention, including mixtures thereof in all ratios, for the preparation of a medicament for immunotherapeutic DNA vaccination.

The invention furthermore relates to a pharmaceutical preparation comprising at least one hypoallergenic variant according to the invention, at least one DNA molecule according to the invention and/or at least one recombinant expression vector according to the invention, including mixtures thereof in all ratios, and optionally further excipients and/or assistants for the prevention and/or therapeutic treatment of type 1 allergies.

In particular, pharmaceutical preparations according to the invention are suitable for the prevention and/or therapeutic treatment of type 1 allergies in the triggering of which group 5 allergens of the true grasses are causally involved.

Pharmaceutical preparations in the sense of this invention can be used as therapeutic agents in human or veterinary medicine and can accordingly be administered to humans and animals, in particular mammals, such as monkeys, dogs, cats, rats or mice, and can be used in the therapeutic treatment of the human or animal body and in the combating of the above-mentioned diseases. They can furthermore be used as diagnostic agents or as reagents.

On use of preparations or medicaments according to the invention, the hypoallergenic variants, DNA molecules or recombinant expression vectors according to the invention are generally used analogously to known, commercially available preparations, preferably in doses between 0.001 and 500 mg, in the case of hypoallergenic variants about 1-500 µg, preferably 5-200 µg, per dose in the maintenance phase. The preparation can be administered once or a number of times per day, for example twice, three times or four times per day. The doses are typically increased to the maintenance dose in a dosage-increase phase. Various dosage-increase and maintenance schemes are possible for this purpose. In the case of subcutaneous immunotherapy (SCIT), for example, these may include short-term therapies (limited number of injections before commencement of seasonal complaints, typically 4-7 injections), pre-seasonal therapies (beginning of therapy before the pollen season, typically with weekly injections during the increase phase and monthly injections with the maintenance dose until the beginning of the pollen season) or full-year therapies (dosage-increase phase typically with up to 16 weekly injections followed by monthly injections with the maintenance dose, if necessary reduced dose during the pollen season). In the case of sublingual immunotherapy with aqueous, or solid preparations (tablets, wafers etc.), the therapy can be introduced with or without a dosage-increase phase. The therapy is preferably carried out with daily doses throughout the year, but can also be carried out pre-seasonally or with other application schemes (for example every second day, weekly, monthly).

The expression "effective amount" means the amount of a medicament or pharmaceutical active compound which causes a biological or medical response in a tissue, system, animal or human which is sought or aimed at, for example, by a researcher or physician.

In addition, the expression "therapeutically effective amount" means an amount which, compared with a corresponding subject who has not received this amount, has the following consequence: improved treatment, healing, prevention or elimination of a disease, syndrome, condition, complaint, disorder or prevention of side effects or also the reduction in the progress of a disease, complaint or disorder. The term "therapeutically effective amount" also encompasses the amounts which are effective in increasing normal physiological function.

Medicaments can be adapted for administration via any desired suitable route, for example by oral (including buccal or sublingual), rectal, pulmonary, nasal, topical (including buccal, sublingual or transdermal), vaginal or parenteral (including subcutaneous, intramuscular, intravenous or intradermal) routes. Such medicaments can be prepared using all processes known in the pharmaceutical area, for example by combining the active compound with the excipient(s) or assistant(s).

Suitable for parenteral use are, in particular, solutions, preferably oily or aqueous solutions, furthermore suspensions, emulsions or implants. The allergen variants according to the invention can also be lyophilised and the resultant lyophilisates used, for example, for the preparation of injection preparations. The preparations indicated may be sterilised and/or comprise adjuvants, such as lubricants, preservatives, stabilisers and/or wetting agents, emulsifiers, salts for modifying the osmotic pressure, buffer substances and/or a plurality of further active compounds. Furthermore, depot preparations can be obtained by corresponding formulation of the allergen variants according to the invention, for example by adsorption onto aluminium hydroxide, calcium phosphate or tyrosine.

Suitable excipients are organic or inorganic substances which are suitable for parenteral administration and do not react with group 5 allergen variants according to the invention. Examples thereof are excipients such as water, vegetable oils, benzyl alcohols, polyethylene glycols, glycerol triacetate, gelatine, carbohydrates, such as lactose or starch, magnesium stearate, talc, lanolin or Vaseline.

Parenteral administration is preferably suitable for the administration of the medicaments according to the invention. In the case of parenteral administration, intravenous, subcutaneous, intradermal or intralymphatic administration are particularly preferred. In the case of intravenous administration, the injection can take place directly or as an addition to infusion solutions.

Medicaments which are adapted to parenteral administration include aqueous and non-aqueous sterile injection solutions, which comprise antioxidants, buff-ers, bacteriostatics and solubilisers by means of which the formulation is rendered isotonic with the blood of the recipient to be treated, and aqueous and non-aqueous sterile suspensions, which may comprise suspension agents and thickeners. The formulations can be administered in single-dose or multi-dose containers, for example sealed ampoules and vials, and stored in freeze-dried (lyophilised) state, meaning that only the addition of the sterile carrier liquid, for example water for injection purposes, immediately before use is necessary. Injection solutions and suspensions prepared in accordance with the formulation can be prepared from sterile powders, granules and tablets.

If desired, preparations or medicaments according to the invention may comprise one or more further active compounds and/or one or more action enhancers (adjuvants).

The present invention thus furthermore relates to pharmaceutical preparations comprising further active compounds and/or assistants. The invention preferably relates to pharmaceutical preparations according to the invention, characterised in that the further active compounds are allergens or variants thereof. Examples of suitable further active compounds are other allergens, in particular allergens of the true grasses, particularly preferably allergens from the Pooideae sub-family, preferably from the groups Poodae and Triticodae, preferably represented by *Phleum pratense, Holcus lanatus, Phalaris aquatica, Dactylis glomerata, Lolium perenne, Poa pratensis, Hordeum vulgare, Secale cereale* and *Triticum aestivum*, for example group 1, 2, 3, 4, 5, 6, 7, 10, 12 or 13 allergens and variants thereof, for example hypoallergenic variants, fragments, multimers, hybrid molecules or recombinant fusion proteins. The present invention furthermore relates to pharmaceutical preparations comprising at least one further assistant, particularly preferably so-called adjuvants. Examples of adjuvants are aluminium hydroxide, monophosphoryl lipid A, activators of Toll-like receptors, such as, for example, lipopolysaccharides and CpG oligonucleotides, vitamin D3, mycobacterial antigens and molecules from parasites (for example schistosomes or filariae), such as, for example, Cystatin or ES-62.

The invention also relates to sets (kits) consisting of separate packs of a) a pharmaceutical preparation according to the invention comprising an effective amount of a hypoallergenic variant, DNA molecule or recombinant expression vector according to the invention b) a pharmaceutical preparation comprising an effective amount of a further pharmaceutical active compound and/or adjuvant.

The set contains suitable containers, such as boxes or cartons, individual bottles, bags or ampoules. The set may contain, for example, separate ampoules each containing a formulation according to the invention comprising an effective amount of a hypoallergenic variant, DNA molecule or recombinant expression vector according to the invention and a formulation of a further medicament active compound in dissolved or lyophilised form.

EXPLANATIONS OF THE FIGURES

FIG. 1*a*: Alignment of deduced amino acid sequences of the group 5 allergens of the Poaceae: Alignment of ripe group 5 sequences of various species. The boxes show the position of the α-helices of Phl p 6 (PDB entry 1NLX) and the C-terminal half of a Phl p 5.02 fragment (PDB entry 1 L3P). The amino acid positions of the proline residues are labelled in accordance with their position in ripe Phl p 5.0109.

Sequence references: Phl p 5.0101 (SEQ ID NO: 8) (*Phleum pratense* IUIS sequence, UniProtKB Q40960), Phl p 5.0104 (SEQ ID NO: 9) (*Phleum pratense* IUIS sequence, UniProtKB P93467), Phl p 5.0109 (SEQ ID NO: 2) (*Phleum pratense* IUIS sequence, UniProtKB Q84UI2), Phl p 5.0201 (SEQ ID NO: 10) (*Phleum pratense* IUIS sequence, UniProtKB Q40963), Phl p 6.0101 (SEQ ID NO: 11) (*Phleum pratense* IUIS sequence, UniProtKB P43215), Lol p 5.0101 (SEQ ID NO: 12) (*Lolium perenne* IUIS sequence, UniProtKB Q40237), Pha a 5.0101 (SEQ ID NO: 13) (*Phalaris aquatica* IUIS sequence, UniProtKB P56164), Dac g 5 (SEQ ID NO: 14) (*Dactylis glomerata*, UniProtKB Q93XD9), Hal I 5.0101 (SEQ ID NO: 15) (*Holcus lanatus* IUIS sequence, UniProtKB O23972), Hal I 5.0201 (SEQ ID NO: 16) (*Holcus lanatus* IUIS sequence, UniProtKB 23971), Poa p 5.0101 (SEQ ID NO: 17) (*Poa pratensis* IUIS sequence, UniProtKB Q9FPR0), Tri a 5 (SEQ ID NO: 18) (*Triticum aestivum*, UniProtKB Q70JP9), Hor v 5 (SEQ ID NO: 19) (*Hordeum vulgare*, EST TC190653).

FIG. 1 *b*: Preservation of the proline residues

FIG. 2: Working model of the position of the proline residues in the 3D structure of Phl p 5a 3D homology model of the N-terminal (amino acids 31-139 of Phl p 5.0109; model molecule: Phl p 6, PDB entry 1 NLX; depicted on the left-hand side) and C-terminal 4-helix bundle (amino acids 155-255; model molecule: Phl p 5b fragment, PDB entry 1 L3P; right).

a. Highly simplified model of the two 4-helix bundles. H1-H8: helices 1-8. Prolines are shown with their position designation and atomic structure. Proline residues P146 and P256 are in regions which it has not been possible to show owing to the lack of structural data in the 3D models of the model molecules (dotted lines). The loop depicted between helix 2 and 3 is speculative, since the model molecule Phl p 6 has no region which is homologous to this Phl p 5a region.

b. Surface model. All proline residues which can be depicted are exposed at the surface (coloured black).

FIG. 3: rPhl p 5a wt (IUIS entry Phl p 5.0109); cDNA sequence (GenBank entry: AJ555152; 855 bp), SEQ ID NO:1

FIG. 4: rPhl p 5a wt (IUIS entry Phl p 5.0109); deduced amino acid sequence (UniProtKB entry: Q84UI2; 284 aa), SEQ ID NO:2

FIG. 5: N-terminal histidine fusion component; DNA sequence (57 bp), SEQ ID NO:3

FIG. 6: N-terminal histidine fusion component; amino acid sequence (19 aa) SEQ ID:4

FIG. 7: Results of the IgE inhibition tests with Phl p 5a variants with proline deletions in individual loops on use of a serum pool ("6His" disclosed as SEQ ID NO: 6)

(a)+(b): Data from one individual experiment in each case with double determination. The symbols represent the means of the duplicates on measurement of eight inhibitor concentrations in each case. The horizontal lines of the error bars show the individual values of the double determination.

(c): Summary of the results of a number of individual experiments.

Left-hand bar (dark grey): IgE inhibition relative to rPhl p 5a wt at an inhibitor concentration of 5 μg/ml.

Right-hand bar (pale grey): IgE inhibition relative to rPhl p 5a wt at an inhibitor concentration of 1.25 μg/ml.

The bar height shows the mean obtained from a number (n) of individual experiments. The error bars show maximum (horizontal line of the upper error bar) and minimum (horizontal line of the lower error bar) values obtained in a number (n) of evaluated individual experiments.

Solid phase: rPhl p 5a wt. Serum pool: Bor 18/100, Allergopharma.

FIG. 8: Comparison of the IgE inhibition of rPhl p 5a d[P117, 180]+6His with the single-position proline mutants rPhl p 5a d[P117]+6His and d[P180]+6His ("6His" disclosed as SEQ ID NO: 6)

Summary of the results of a number of individual experiments:

Left-hand bar (dark grey): IgE inhibition relative to rPhl p 5a wt at an inhibitor concentration of 5 μg/ml.

Right-hand bar (pale grey): IgE inhibition relative to rPhl p 5a wt at an inhibitor concentration of 1.25 μg/ml.

The bar height shows the mean obtained from a number (n) of individual experiments. The error bars show maximum (horizontal line of the upper error bar) and minimum (horizontal line of the lower error bar) values obtained in a number (n) of evaluated individual experiments.

Solid phase: rPhl p 5a wt. Serum pool: Bor 18/100, Allergopharma.

FIG. 9: Comparison of the IgE inhibition of MPV.3+6His with the single-position proline mutants rPhl p 5a d[P57, 58]+6His and d[P229]+6His ("6His" disclosed as SEQ ID NO: 6)

Summary of the results of a number of individual experiments:

Left-hand bar (dark grey): IgE inhibition relative to rPhl p 5a wt at an inhibitor concentration of 5 µg/ml.

Right-hand bar (pale grey): IgE inhibition relative to rPhl p 5a wt at an inhibitor concentration of 1.25 µg/ml.

The bar height shows the mean obtained from a number (n) of individual experiments.

The error bars show maximum (horizontal line of the upper error bar) and minimum (horizontal line of the lower error bar) values obtained in a number (n) of evaluated individual experiments.

Solid phase: rPhl p 5a wt. Serum pool: Bor 18/100, Allergopharma.

FIG. 10: Comparison of the IgE inhibition of MPV.3+6His with the single-position proline mutants rPhl p 5a d[P211]+6His, P211L+6His, K61E+6His and E205K+6His ("6His" disclosed as SEQ ID NO: 6)

Summary of the results of a number of individual experiments:

Left-hand bar (dark grey): IgE inhibition relative to rPhl p 5a wt at an inhibitor concentration of 5 µg/ml.

Right-hand bar (pale grey): IgE inhibition relative to rPhl p 5a wt at an inhibitor concentration of 1.25 µg/ml.

The bar height shows the mean obtained from a number (n) of individual experiments.

The error bars show maximum (horizontal line of the upper error bar) and minimum (horizontal line of the lower error bar) values obtained in a number (n) of evaluated individual experiments.

Solid phase: rPhl p 5a wt. Serum pool: Bor 18/100, Allergopharma.

FIG. 11: Test for functional allergeneity of MPV.3+6His ("6His" disclosed as SEQ ID NO: 6)

Evidence of the reduced functional allergeneity of MPV.3+6His ("6His" disclosed as SEQ ID NO: 6) by means of basophil activation test with basophils of four clinically defined grass pollen allergy sufferers (P). Horizontal line: level of stimulation by a negative control.

FIG. 12: IgE inhibition test with MPV.4+6His ("6His" disclosed as SEQ ID NO: 6) and MPV.4

Left-hand bar (dark grey): IgE inhibition relative to rPhl p 5a wt at an inhibitor concentration of 5 μg/ml.

Right-hand bar (pale grey): IgE inhibition relative to rPhl p 5a wt at an inhibitor concentration of 1.25 μg/ml.

The bar height shows the mean obtained from a number (n) of individual experiments.

The error bars show maximum (horizontal line of the upper error bar) and minimum (horizontal line of the lower error bar) values obtained in a number (n) of evaluated individual experiments.

Solid phase: rPhl p 5a wt. Serum pool: Bor 18/100, Allergopharma.

FIG. 13: Determination of the molecular weight of MPV.5 Chromatogram of an analytical SEC with online molecular weight determination.

The figure shows the relative UV signal at 280 nm (right-hand Y axis) and the molecular weight (left-hand Y axis; measurement point line in the peak region), plotted against the elution time (X axis).

For online determination of the protein concentration, the OptilabrEX refractive index detector (Wyatt, Santa Barbara, USA) was employed. The light scattering by the particles was determined using the MiniDAWN Treos multiangle detector (Wyatt). The particle weight was calculated using the ASTRA 5.3.2.17 software (Wyatt) via Debeye formalism with a refractive-index increment of 0.180 ml/g.

Column: Superdex 200 GL 10/300 (GE Healthcare, Uppsala, Sweden). The size exclusion ($t_0$) is at 20.45 min (corresponds to ~670 kD).

Eluent: 20 mM Tris 8.0, 150 mM NaCl

FIG. 14: Determination of the molecular weight of MPV.7 Chromatogram of an analytical SEC with online molecular weight determination.

The figure shows the relative UV signal at 280 nm (right-hand Y axis) and the molecular weight (left-hand Y axis; measurement point line in the peak region), plotted against the elution time (X axis).

For online determination of the protein concentration, the OptilabrEX refractive index detector (Wyatt, Santa Barbara, USA) was employed. The light scattering by the particles was determined using the MiniDAWN multiangle detector Treos (Wyatt). The particle weight was calculated using ASTRA 5.3.2.17 software (Wyatt) via Debeye formalism with a refractive-index increment of 0.180 ml/g.

Column: Superdex 200 GL 10/300 (GE Healthcare, Uppsala, Sweden). The size exclusion ($t_0$) is at 20.45 min (corresponds to ~670 kD).

Eluent: 20 mM Tris 8.0, 150 mM NaCl

FIG. 15: Determination of the molecular weight of MPV.4 Chromatogram of an analytical SEC with online molecular weight determination.

The figure shows the relative UV signal at 280 nm (right-hand Y axis) and the molecular weight (left-hand Y axis; measurement point line in the peak region), plotted against the elution time (X axis).

For online determination of the protein concentration, the OptilabrEX refractive index detector (Wyatt, Santa Barbara, USA) was employed. The light scattering by the particles was determined using the MiniDAWN Treos multiangle detector (Wyatt). The particle weight was calculated using ASTRA 5.3.2.17 software (Wyatt) via Debeye formalism with a refractive-index increment of 0.180 ml/g.

Column: Superdex 200 GL 10/300 (GE Healthcare, Uppsala, Sweden). The size exclusion ($t_0$) is at 20.45 min (corresponds to ~670 kD).

Eluent: 20 mM Tris 8.0, 150 mM NaCl

FIG. 16: Determination of the molecular weight of MPV.6 Chromatogram of an analytical SEC with online molecular weight determination.

The figure shows the relative UV signal at 280 nm (right-hand Y axis) and the molecular weight (left-hand Y axis; measurement point line in the peak region), plotted against the elution time (X axis).

For online determination of the protein concentration, the OptilabrEX refractive index detector (Wyatt, Santa Barbara, USA) was employed. The light scattering by the particles was determined using the MiniDAWN Treos multiangle detector (Wyatt). The particle weight was calculated using ASTRA 5.3.2.17 software (Wyatt) via Debeye formalism with a refractive-index increment of 0.180 ml/g.

Column: Superdex 200 GL 10/300 (GE Healthcare, Uppsala, Sweden). The size exclusion ($t_0$) is at 20.45 min (corresponds to ~670 kD).

Eluent: 20 mM Tris 8.0, 150 mM NaCl

FIG. 17: IgE binding to immobilised MPV.4, MPV.5, MPV.6 and MPV.7 Test for binding of IgE to Phl p 5 proteins immobilised on nitrocellulose membrane strips.

rPhl p 5b wt: recombinant Phl p 5b isoform rPhl p 5a wt: recombinant Phl p 5a isoform nPhl p 5a/b: Phl p 5 allergen of natural origin, consisting of protein of the a and b isoform (Allergopharma)

MPV.4: d[P57, P58, P117, P146, P155, P180, P229] K61E E205K P211L

MPV.5: d[P57, P58, P117, P180, P229] K61E E205K P211 L

MPV.6: d[P57, P58, P117, P146, P155, P180, P229] P211L

MPV.7: d[P57, P58, P117, P180, P229] P211L

HSA: albumin from human serum (negative control).

Total: control for uniform charging of the strips. Staining with reagent DB71 (Sigma, USA)

SP: serum pool Bor18/100 (Allergopharma)

FIG. 18: IgE inhibition test with MPV.5 and MPV.4

Left-hand bar (dark grey): IgE inhibition relative to rPhl p 5a wt at an inhibitor concentration of 5 µg/ml.

Right-hand bar (pale grey): IgE inhibition relative to rPhl p 5a wt at an inhibitor concentration of 1.25 µg/ml.

The bar height shows the mean obtained from a number (n) of individual experiments.

The error bars show maximum (horizontal line of the upper error bar) and minimum (horizontal line of the lower error bar) values obtained in a number (n) of evaluated individual experiments.

Solid phase: rPhl p 5a wt. Serum pool: Bor 18/100, Allergopharma.

FIG. 19: IgE inhibition test with MPV.6 and MPV.7

Left-hand bar (dark grey): IgE inhibition relative to rPhl p 5a wt at an inhibitor concentration of 5 µg/ml.

Right-hand bar (pale grey): IgE inhibition relative to rPhl p 5a wt at an inhibitor concentration of 1.25 µg/ml.

The bar height shows the mean obtained from a number (n) of individual experiments.

The error bars show maximum (horizontal line of the upper error bar) and minimum (horizontal line of the lower error bar) values obtained in a number (n) of evaluated individual experiments.

Solid phase: rPhl p 5a wt. Serum pool: Bor 18/100, Allergopharma.

FIG. 20: Test for functional allergeneity of MPV.4

Evidence of the reduced functional allergeneity of MPV.4 by means of basophil activation test with basophils of four clinically defined grass pollen allergy sufferers (P).

Horizontal line: level of stimulation by a negative control.

FIG. 21: Test for functional allergeneity of MPV.5

Evidence of the reduced functional allergeneity of MPV.5 by means of basophil activation test with basophils of four clinically defined grass pollen allergy sufferers (P).

Horizontal line: level of stimulation by a negative control.

FIG. 22: Test for functional allergeneity of MPV.6

Evidence of the reduced functional allergeneity of MPV.6 by means of basophil activation test with basophils of clinically defined grass pollen allergy sufferers (P).

Horizontal line: level of stimulation by a negative control.

FIG. 23: Test for functional allergeneity; MPV.7

Evidence of the reduced functional allergeneity of MPV.7 by means of basophil activation test with basophils of four clinically defined grass pollen allergy sufferers (P).

Horizontal line: level of stimulation by a negative control.

FIG. 24: rPhl p 5b wt precursor (IUIS entry Phl p 5.0201); deduced amino acid sequence 284 aa (Swiss prot: Q40963.2), SEQ ID NO:5

Even without further embodiments, it is assumed that a person skilled in the art will be able to utilise the above description in the broadest scope. The preferred embodiments should therefore merely be regarded as descriptive disclosure, which is, however, in no way limiting in any way.

The following examples are thus intended to explain the invention without limiting it. Unless indicated otherwise, percent data mean percent by weight. All temperatures are indicated in degrees Celsius. "Conventional work-up": water is added if necessary, the pH is adjusted, if necessary, to values between 2 and 10, depending on the constitution of the end product.

The following hypoallergenic variants according to the invention were prepared by biotechnological methods and characterised. However, the preparation and characterisation of the substances can also be carried out by other methods for the person skilled in the art. For example, the hypoallergenic variants according to the invention can also be synthesised chemically. The invention likewise relates to the hypoallergenic variants according to the invention described below.

EXAMPLE 1: VARIANTS OF PHL P 5A WITH ONE OR TWO ADJACENT PROLINE DELETIONS

The preparation of variants rPhl p 5a d[P57, P58]+6His, rPhl p 5a d[P85]+6His, rPhl p 5a d[P117]+6His, rPhl p 5a d[P146, P155]+6His, rPhl p 5a d[P180]+6His, rPhl p 5a d[P211]+6His, rPhl p 5a d[P229]+6His and rPhl p 5a d[P256]+6His and immunological characterisation thereof is described below ("6His" disclosed as SEQ ID NO: 6). The recombinant unmodified allergen (rPhl p 5 wt+6His ("6His" disclosed as SEQ ID NO: 6)) is prepared and investigated analogously, and the hypoallergenic variants of the other group 5 allergens according to the invention of the true grasses and their wild-type proteins, in particular Lol p 5 and Poa p 5, can also be prepared and investigated analogously.

Construction by Genetic Engineering:

The DNA of the variants are synthesised by the bonding of long overlapping DNA oligonucleotides and amplification of the DNA by a PCR standard method. The codons are selected so that the deduced amino acid sequence is based on that of Phl p 5.0109 (FIG. 3, 4). The mutations for the proline deletions are introduced using specific oligonucleotides which lack the corresponding codons for proline in the PCR reactions. The oligonucleotides are selected so that the deduced protein carries a hexahistidine (SEQ ID NO: 6) fusion component at the 5' end (FIG. 5, 6). The cDNAs are ligated into expression vector pTrcHis2 Topo (Invitrogen, Carlsbad, USA). The correctness of the DNA is confirmed by sequencing.

Expression, Purification and Biochemical Analysis:

The expression is carried out in *Escherichia coli* (Top10 strain; Invitrogen). rPhl p 5a wt and the variants are purified by specific binding of the N-terminal histidine residues to an Ni2+ chelate matrix (immobilised metal ion affinity chromatography, IMAC; material: HiTrap, GE Healthcare, Uppsala, Sweden). The absence of insoluble protein aggregates is confirmed by UV-Vis spectroscopy.

Evidence of Reduced IgE Binding:

The investigation of the IgE binding ability of the test substances is carried out using an EAST-IgE inhibition test (enzyme allergosorbent test). In this method, the allergen/IgE interaction can be investigated in solution, enabling interfering masking of epitopes of the test substance to be excluded, for example by immobilisation on a membrane.

The EAST inhibition test is carried out as follows. Microtitre plates are coated with the allergens, here recombinant wild-type Phl p 5.0109 (rPhl p 5a wt). After removal of the unbound allergen molecules by washing, the plate is blocked with bovine serum albumin in order to prevent later nonspecific binding. IgE antibodies of allergy sufferers in the form of a representative pool of individual allergy sufferer sera (serum pool) in suitable dilution are incubated with the allergen-coated microtitre plates. The amount of allergen-bound IgE antibodies is quantified photometrically via an anti-human-IgE/alkaline phosphatase conjugate by the reaction of a substrate to give a coloured end product.

The binding of the IgE antibodies is inhibited substance-specifically by a soluble allergen or the substance to be tested (recombinant modified allergen) as a function of the concentration. The results depicted in FIG. 7. of IgE inhibition tests with the recombinant allergen variants of Phl p 5a show that reduced IgE binding ability of Phl p 5a is caused by deletion of proline residues P57 and P58; P117; P146 and P155; P180; P211 or P229, but not by deletion of P85 or P256. A reduced inhibitory action indicates a loss of IgE epitopes.

EXAMPLE 2: VARIANTS OF PHL P 5A WITH COMBINATIONS OF PROLINE DELETIONS

The preparation and immunological characterisation of variant rPhl p 5a d[P117, P180]+6His ("6His" disclosed as SEQ ID NO: 6) is described below by way of example for hypoallergenic variants according to the invention of group 5 allergens of the Poaceae with combinations of a plurality of proline deletions corresponding to amino acid positions of 57 and 58, 117, 146, and 155, 180, 211 and 229, based on Phl p 5.0109. The recombinant unmodified allergen (rPhl p 5 wt+6His ("6His" disclosed as SEQ ID NO: 6)) is prepared and investigated analogously, and the hypoallergenic variants of the other group 5 allergens according to the invention of the true grasses and their wild-type proteins, in particular Lol p 5 and Poa p 5, can also be prepared and investigated analogously.

Construction by Genetic Engineering:

The variants are synthesised by the bonding of long overlapping DNA oligonucleotides and amplification of the DNA by PCR. The codons are selected so that the deduced amino acid sequence is based on that of Phl p 5.0109. The mutations for the proline deletions are introduced using specific oligonucleotides which lack the corresponding codons for proline in the PCR reactions. The oligonucleotides are selected so that the deduced protein carries a hexahistidine (SEQ ID NO: 6) fusion component at the 5' end. The cDNAs are transformed into expression vector pTrcHis2 Topo (Invitrogen) and in *Escherichia coli*. The correctness of the DNA is confirmed by sequencing.

Expression, Purification and Biochemical Analysis:

The expression is carried out in *Escherichia coli* (Top10 strain; Invitrogen). The variants are purified by IMAC. The purity of the eluted proteins is checked by SDS-PAGE, and the absence of insoluble protein aggregates is confirmed by UV-Vis spectroscopy.

Evidence of Reduced IgE Binding:

The investigation of the IgE binding ability of the test substances is carried out using an EAST inhibition test with IgE antibodies of allergy sufferers which were employed in the form of a representative serum pool. The results depicted in FIG. 8 show that IgE inhibition of variant rPhl p 5a d[P117, P180]+6His is significantly lower than that of the variants with only one of proline deletions rPhl p 5a d[P117]+6His and rPhl p 5a d[P180]+6His ("6His" disclosed as SEQ ID NO: 6). This result shows that the combination of individual proline deletions can result in increased reduction of the IgE binding ability of Phl p 5a.

EXAMPLE 3: HYPOALLERGENIC VARIANT RPHL P 5A D[P57, P58, P85, P117, P146, P155, P180, P211, P229, P256] (MPV.1+6HIS ("6HIS" DISCLOSED AS SEQ ID NO: 6))

Allergen variant MPV.1+6His ("6His" disclosed as SEQ ID NO: 6) has a combination of the deletions of all Phl 5a proline residues investigated. The aim of the preparation is IgE binding ability reduced to the maximum with acceptable protein solubility.

Construction by Genetic Engineering:

The variants are synthesised by the bonding of long overlapping DNA oligonucleotides and amplification of the DNA by PCR. The codons are selected so that the deduced amino acid sequence is based on that of Phl p 5.0109. The mutations for the proline deletions are introduced using specific oligonucleotides which lack the corresponding codons for proline in the PCR reactions.

The oligonucleotides are selected so that the deduced protein carries a hexahistidine (SEQ ID NO: 6) fusion component at the 5' end. The cDNA are transformed into expression vector pTrcHis2 Topo (Invitrogen) and in *Escherichia coli*. The correctness of the DNA is confirmed by sequencing.

Expression:

The expression is carried out in *Escherichia coli* (Top10 strain; Invitrogen). The proteins are deposited by the host cell as insoluble inclusion bodies.

Test of Solubility:

The protein aggregates are isolated in a purity of about 80% after cell digestion using a standard method and solubilised in a denaturing manner by treatment with a 6 molar solution of guanidinium hydrochloride.

The denatured proteins are diluted 1:50 in a volume of 25 ml for this testing at 4° C. and kept at 4° C. overnight. On the following day, any visible precipitate formation is checked organoleptically. After partial concentration, the samples are centrifuged, and the clear supernatants are investigated for the presence of insoluble microaggregates by means of UV-Vis spectroscopy.

The systematic investigation of the solubility behaviour of variant MPV.1+6His ("6His" disclosed as SEQ ID NO: 6) shows that subsequent conversion of the proteins into a guanidinium hydrochloride-free formulation is always accompanied by the formation of protein aggregates and is thus not possible (Table 1)

EXAMPLE 4: HYPOALLERGENIC VARIANT RPHL P 5A D[P57, P58, P117, P146, P155, P180, P211, P229] (MPV.2+6HIS ("6HIS" DISCLOSED AS SEQ ID NO: 6))

The preparation and immunological characterisation of variant MPV.2+6His ("6His" disclosed as SEQ ID NO: 6) is described below by way of example for hypoallergenic variants of group 5 allergens of the Poaceae with combinations of protein deletions corresponding to amino acid positions 57, 58, 117, 146, 155, 180, 211 and 229, based on Phl p 5.0109. The recombinant unmodified allergen (rPhl p 5 wt+6His ("6His" disclosed as SEQ ID NO: 6)) is prepared and investigated analogously, and the hypoallergenic variants of the other group 5 allergens according to the invention of the true grasses and their wild-type proteins, in particular Lol p 5 and Poa p 5, can also be prepared and investigated analogously.

Construction by Genetic Engineering:

The variants are synthesised by the bonding of long overlapping DNA oligonucleotides and amplification of the DNA by PCR. The codons are selected so that the deduced amino acid sequence is based on that of Phl p 5.0109.

The mutations for the proline deletions are introduced using specific oligonucleotides which lack the corresponding codons for proline in the PCR reactions.

The oligonucleotides are selected so that the deduced protein carries a hexahistidine (SEQ ID NO: 6) fusion component at the 5' end. The cDNA are ligated into expression vector pTrcHis2 Topo (Invitrogen) and transformed in Escherichia coli. The correctness of the DNA is confirmed by sequencing.

Expression:

The expression is carried out in Escherichia coli (Top10 strain; Invitrogen). The proteins are deposited by the host cell as insoluble inclusion bodies.

Test of Solubility:

MPV.2+6His ("6His" disclosed as SEQ ID NO: 6) exhibits poor solubility throughout the pH range of 4.5-9.0 investigated. The formation of visible precipitates can only be prevented with a solutions comprising Tween 80 and L-arginine monohydrochloride, but microaggregates are also detected in this batch below (Table 2).

EXAMPLE 5: HYPOALLERGENIC VARIANT RPHL P 5A D[P57, P58, P229] K61E, E205K, P211 L (MPV.3+6HIS ("6HIS" DISCLOSED AS SEQ ID NO: 6))

The preparation and immunological characterisation of variant MPV.3+6His ("6His" disclosed as SEQ ID NO: 6) is described below by way of example for hypoallergenic variants of group 5 allergens of the Poaceae with combinations of deletions of proline residues 57, 58, 117, 146, 155, 180 or 229 corresponding to the amino acid positions in Phl p 5 5.0109, in which proline residue 211 is mutated into any desired other amino acid or in which lysine 61 is additionally converted into glutamate or glutamate 205 is converted into lysine. The recombinant unmodified allergen (rPhl p 5 wt+6His ("6His" disclosed as SEQ ID NO: 6)) is prepared and investigated analogously, and the hypoallergenic variants of the other group 5 allergens according to the invention of the true grasses and their wild-type proteins, in particular Lol p 5 and Poa p 5, can also be prepared and investigated analogously.

The effect of mutations K61E, E205K and P211 L present in the amino acid sequence of MPV.3+6His on the IgE binding ability is investigated by preparing variants rPhl p 5a K61E+6His, rPhl p 5a E205K+6His and rPhl p 5a P211 L+6His and characterising them immunologically ("6His" disclosed as SEQ ID NO: 6).

Construction by Genetic Engineering:

The nucleotide sequence encoding for MPV.3+6His ("6His" disclosed as SEQ ID NO: 6) is surprisingly generated in this example by a number of polymerase errors in a cDNA synthesis. The DNA is ligated into expression vector pTrcHis2 Topo (Invitrogen). The DNA encoding for variants rPhl p 5a K61E+6His, rPhl p 5a E205K+6His and rPhl p 5a P211 L+6His are prepared specifically and ligated into expression vector pTrcHis2 Topo ("6His" disclosed as SEQ ID NO: 6). The correctness of the generated cDNA sequences is checked by DNA sequencing.

Expression:

The expression is carried out in Escherichia coli (Top10 strain; Invitrogen). The proteins are deposited by the host cell as insoluble inclusion bodies.

Test of the Solubility of MPV.3+6His ("6His" Disclosed as SEQ ID NO: 6):

The protein aggregates are isolated in a purity of about 80% after cell digestion and solubilised in a denaturing manner by treatment with a 6 molar solution of guanidinium hydrochloride. The series testing of various solutions in order to check the solubility properties of MPV.3+6His in a non-denaturing environment is carried out analogously to the experiments with variants MPV.1+6His and MPV.2+6His ("6His" disclosed as SEQ ID NO: 6).

Surprisingly, it is observed that variant MPV.3+6His ("6His" disclosed as SEQ ID NO: 6) has high solubility at slightly basic pH during the dilution process (Table 3). This behaviour is in contrast to variants MPV.1+6His and MPV.2+6His investigated above and represents a crucial advantage for the preparation of the protein in a non-denaturing environment ("6His" disclosed as SEQ ID NO: 6).

Purification of MPV.3+6His, and Mutants rPhl p 5a K61E+6His, rPhl p 5a E205K+6His and rPhl p 5a P211 L+6His ("6His" Disclosed as SEQ ID NO: 6):

The denatured proteins are diluted 1:50 in 20 mM Tris, 150 mM NaCl, pH 9.0, and kept at 8° C. overnight. The chromatographic purification is carried out by IMAC (HiTrap material, GE Healthcare) and SEC (Superdex 75 material, GE Healthcare). The proteins are finally in stable and soluble form in 25 mM sodium phosphate buffer with 150 mM NaCl, pH 7.5.

Biochemical Analysis:

The purity is checked by SDS-PAGE. The absence of insoluble protein aggregates is confirmed by UV-Vis spectroscopy.

Evidence of the Reduced IgE Binding of MPV.3+6His ("6His" Disclosed as SEQ ID NO: 6):

The investigation of the IgE binding ability of MPV.3+6His ("6His" disclosed as SEQ ID NO: 6) is carried out using an EAST inhibition test with IgE antibodies of allergy sufferers which are employed in the form of a representative serum pool. The results depicted in FIG. 9 show that the IgE inhibition of MPV.3+6His is significantly lower than that of variants rPhl p 5a d[P57, P58]+6His and rPhl p 5a d[P229]+6His ("6His" disclosed as SEQ ID NO: 6).

For further characterisation of mutations K61E, E205K and P211 L of variant MPV.3+6His, the three variants rPhl p 5a K61E+6His, rPhl p 5a E205K+6His and rPhl p 5a P211 L+6His are investigated by EAST ("6His" disclosed as SEQ ID NO: 6).

Variant rPhl p 5a P211 L+6His exhibits a comparably low inhibition behaviour to the point mutant rPhl p 5a d[P211]+6His tested previously ("6His" disclosed as SEQ ID NO: 6). Variants rPhl p 5a K61E+6His and rPhl p 5a E205K+6His exhibit slightly reduced IgE binding (FIG. 10) ("6His" disclosed as SEQ ID NO: 6).

It can be concluded that the three point mutations K61E, E205K and P211 L contribute to the significantly reduced IgE binding of MPV.3+6His ("6His" disclosed as SEQ ID NO: 6).

Evidence of the Reduction of the Functional Allergeneity of MPV.3+6His ("6His" Disclosed as SEQ ID NO: 6):

The functional action of MPV.3+6His ("6His" disclosed as SEQ ID NO: 6) in the crosslinking of membrane-bound IgE of the effector cells and activation thereof is investigated in vitro.

For the basophil activation test, heparinised whole blood of grass pollen allergy sufferers is incubated with various concentrations of the test substances. Allergenic substances are able to bind specific IgE antibodies which are associated with the high-affinity IgE receptors of the basophilic granulocytes. The crosslinking of the IgE/receptor complexes triggered by the allergen molecules results in signal transduction, which results in degranulation of the effector cells and thus the triggering of the allergic reactions in vivo.

The allergen-induced activation of basophilic immunocytes can be determined in vitro by quantification of the expression of a surface protein (CD203c) coupled to the signal transduction of IgE-receptor crosslinking (Kahlert et al., Clinical Immunology and Allergy in Medicine Proceedings of the EAACI 2002 (2003) Naples, Italy 739-744). The number of surface proteins expressed on a cell and the percentage value of the activated cells of a cell pool is measured highly sensitively via the binding of a fluorescence-labelled monoclonal antibody to the surface protein and subsequent analysis by fluorescence-activated flow cytometry.

MPV.3+6His ("6His" disclosed as SEQ ID NO: 6) exhibits reduced activation of basophilic granulocytes of grass pollen allergy sufferers here compared with rPhl p 5a wt and thus functionally reduced allergeneity (FIG. 11)

EXAMPLE 6: HYPOALLERGENIC VARIANT RPHL P 5A D[P57, P58, 117, 146, 155, 180, P229] K61E, E205K, P211 L (MPV.4)

The preparation and immunological characterisation of variant MPV.4 is described below by way of example for hypoallergenic variants of group 5 allergens of the Poaceae with combinations of deletions of proline residues 57, 58, 117, 146, 155, 180 or 229 corresponding to the amino acid positions in Phl p 5.0109), in which proline residue 211 is mutated into any desired other amino acid or in which lysine 61 is additionally converted into glutamate or glutamate 205 is converted into lysine. The recombinant unmodified allergen (rPhl p 5 wt+6His ("6His" disclosed as SEQ ID NO: 6)) is prepared and investigated analogously, and the hypoallergenic variants of the other group 5 allergens according to the invention of the true grasses and their wild-type proteins, in particular Lol p 5 and Poa p 5, can also be prepared and investigated analogously.

Construction of MPV.4 (+6His ("6His" Disclosed as SEQ ID NO: 6)) by Genetic Engineering:

In order to prepare the cDNA of the histidine fusion protein of MPV.4 (MPV.4+6His), a fragment of the already cloned cDNA of MPV.1+6His is re-cloned into the plasmid MPV.3+6His/pTrcHis2 Topo which is already present ("6His" disclosed as SEQ ID NO: 6).

In order to prepare the fusion component-free protein (MPV.4), the DNA is ligated into vector pTMP (Allergopharma, Reinbek) without the section encoding for the histidine fusion component. The correctness of the sequence is checked by DNA sequencing.

Expression of MPV.4 (+6His ("6His" disclosed as SEQ ID NO: 6)):

The expression is carried out either as histidine fusion protein (expression vector pTrcHis2Topo; Invitrogen) in *Escherichia coli* (Top10 strain; Invitrogen) or without fusion component (expression vector pTMP) in *Escherichia coli* (BL21 strain; Merck, Darmstadt). In both cases, the recombinant proteins are deposited as inclusion bodies. The proteins are solubilised using a 6 molar solution of guanidinium hydrochloride.

Test of the Solubility of MPV.4+6His ("6His" Disclosed as SEQ ID NO: 6):

The series testing of various solutions in order to check the solubility properties of MPV.4+6His in a non-denaturing environment is carried out analogously to the experiments with variant MPV.1+6His ("6His" disclosed as SEQ ID NO: 6). It is observed that variant MPV.4+6His ("6His" disclosed as SEQ ID NO: 6) has solubility at slightly basic pH (Table 4)

Purification of MPV.4+6His ("6His" Disclosed as SEQ ID NO: 6):

The fusion protein is purified on a preparative scale by IMAC (HiTrap material, GE Healthcare) and SEC (Superdex 75 material, GE Healthcare) and is finally present in 25 mM sodium phosphate buffer with 150 mM NaCl, pH 7.5.

Purification of the Non-Fusion Protein MPV.4:

The solution of the denatured non-fusion protein are firstly diluted 1:50 with 20 mM Tris, 150 mM NaCl, pH 9.0, analogously to the purification scheme of the fusion protein and kept at 4° overnight. In a first purification step, the target protein is enriched by hydrophobic interaction chromatography (HIC).

At high ion strength, proteins bind to an HIC column with specific strength, depending on their surface hydrophobicity, enabling them to be eluted selectively by gradual reduction of the salt concentration.

The diluted protein solution is firstly diluted further 1:2 with 20 mM Tris, 2 M ammonium sulfate, 150 mM NaCl, pH 9.0, in order to achieve a final ammonium sulfate concentration of 1 M. This protein solution is then passed through a HiTrap butyl-S FF HIC column (GE Healthcare, Uppsala, Sweden) and, after binding of the target protein, eluted gradually with 20 mM Tris, 150 mM NaCl, pH 9.0.

As preparation for the second purification step, the HIC eluates are re-buffered in 20 mM Tris, 50 mM NaCl, pH 8.0, via a Sephadex G25 column (GE Healthcare).

As the second purification step, the eluates are applied to an anion exchange chromatography column (HiTrap Q HP, GE Healthcare), and the material passing through the column is collected. The target protein is located in the material passing through the column, while foreign proteins bind to the column and are effectively removed.

In the AIEX process, proteins having a negative surface charge are bound to the column material at low ion strength, while uncharged or positively charged proteins do not bind.

In the final step, the AIEX output is subsequently purified via an SEC column (Superdex 75, GE Healthcare), so that the target protein is finally present in 20 mM Tris, 150 mM NaCl, pH 8.0.

Biochemical Analysis of MPV.4 (+6His ("6His" Disclosed as SEQ ID NO: 6)):

The purity of the proteins is checked by SDS-PAGE. The identity of the fusion component-free MPV.4 is confirmed by determination of the molecular weight by means of mass spectroscopy (MALDI-TOF) and sequencing of the N-terminal amino acids (sequence: A-D-L-G-Y-G-P-A-T (SEQ ID NO: 7)) (Table 6). The absence of insoluble protein aggregates is confirmed by UV-Vis spectroscopy.

Molecular weight analysis of MPV.4 by means of SEC/MALS/RI surprisingly shows that the mass of the eluted proteins is between 28.2 and 49.3 kD (average mass 36.9 kD). Since the theoretical mass of the monomer is 27.6 kD, it can be assumed that a mixture of monomers and dimers is present (FIG. 15, Table 6). Qualitatively the same result is obtained with the fusion protein.

Evidence of the Reduced IgE Binding of MPV.4 (+6His ("6His" Disclosed as SEQ ID NO: 6)):

The investigation of the IgE binding ability is carried out using an EAST inhibition test with IgE antibodies of allergy sufferers which are employed in the form of a representative serum pool.

The results depicted in FIG. 12 show that MPV.4 has IgE binding reduced to the same extent both with and without fusion component. It is thus shown that the reduced IgE reactivity is not dependent on the presence of the histidine tag.

A simple test method for the determination of the IgE reactivity of specific IgE from allergy sufferer sera on membrane-bound test proteins is the strip test. For this purpose, the test substances in the same concentration and amount are bound alongside one another to a strip of nitrocellulose membrane under non-denaturing conditions. A series of such membrane strips can be incubated in parallel with different allergy sufferer sera. After a washing step, the specifically bound IgE antibodies are rendered visible on the membrane by a colour reaction, promoted by an anti-human IgE/alkaline phosphatase conjugate.

The results of variant MPV.4 using individual grass pollen allergy sufferer sera are depicted in FIG. 17. Sera of allergy sufferers with antibodies against natural Phl p 5 (nPhl p 5a/b, mixture of Phl p 5a and b isoform) are used. The IgE antibodies likewise react with the recombinant rPhl p 5a wt and the likewise investigated recombinant wild-type b isoform (rPhl p 5b wt).

It is clear that the Phl p 5-specific IgE antibodies of all allergy sufferer sera bind variant MPV.4 to a greatly reduced extent, while recombinant wild-type proteins rPhl p 5a wt and rPhl p 5b wt are bound just as strongly as nPhl p 5a/b.

Evidence of the Reduction of the Functional Allergeneity of MPV.4:

The functional action of MPV.4 in the crosslinking of membrane-bound IgE of the effector cells and activation thereof is investigated both with fusion proteins and with non-fusion proteins in vitro. Both the fusion protein and the fusion component-free MPV.4 exhibit greatly reduced activation of basophilic granulocytes of grass pollen allergy sufferers here compared with rPhl p 5a wt and thus highly functionally reduced allergeneity (FIG. 20).

EXAMPLE 7: HYPOALLERGENIC VARIANT RPHL P 5A D[P57, P58, P117, P180, P229] K61E, E205K, P211 L (MPV.5)

The preparation and immunological characterisation of variant MPV.5 is described below by way of example for hypoallergenic variants of group 5 allergens of the Poaceae with combinations of deletions of proline residues 57, 58, 117, 180 or 229 corresponding to the amino acid positions in Phl p 5.0109, in which proline residue 211 is mutated into any desired other amino acid or in which lysine 61 is additionally converted into glutamate or glutamate 205 is converted into lysine. The recombinant unmodified allergen (rPhl p 5 wt+6His ("6His" disclosed as SEQ ID NO: 6)) is prepared and investigated analogously, and the hypoallergenic variants of the other group 5 allergens according to the invention of the true grasses and their wild-type proteins, in particular Lol p 5 and Poa p 5, can also be prepared and investigated analogously.

Construction of Mpv.5 (+6His ("6His" Disclosed as SEQ ID NO: 6)) by Genetic Engineering:

In order to prepare the cDNA of the histidine fusion protein (MPV.5+6His), a fragment of the already cloned cDNA of rPhl p 5a d[P117, P180]+6His is re-cloned into the plasmid MPV.3+6His/pTrcHis2 Topo which is already present ("6His" disclosed as SEQ ID NO: 6).

In order to prepare the fusion component-free protein (MPV.5), the DNA is ligated into vector pTMP (Allergopharma, Reinbek) without the section encoding for the histidine fusion component. The correctness of the sequence is checked by DNA sequencing.

Expression of MPV.5 (+6His ("6His" Disclosed as SEQ ID NO: 6)):

The expression is carried out either as histidine fusion protein (expression vector pTrcHis2Topo; Invitrogen) in *Escherichia coli* (Top10 strain; Invitrogen) or without fusion component (expression vector pTMP; Allergopharma) in *Escherichia coli* (BL21 strain; Merck, Darmstadt).

In both cases, the recombinant proteins are deposited as inclusion bodies. The proteins are solubilised by means of a 6 molar solution of guanidinium hydrochloride.

Purification of MPV.5+6His ("6His" Disclosed as SEQ ID NO: 6):

The fusion protein is purified on a preparative scale by IMAC (HiTrap material, GE Healthcare) and SEC (Superdex 75 material, GE Healthcare) and is finally present in 25 mM sodium phosphate buffer with 150 mM NaCl, pH 7.5.

Purification of the Non-Fusion Protein:

The IB solution of the denatured non-fusion protein are firstly diluted 1:50 with 20 mM Tris, 150 mM NaCl, pH 9.0, analogously to the purification scheme of the fusion protein and kept at 4° overnight.

In a first purification step, the target protein is enriched by hydrophobic interaction chromatography (HIC). The dilute protein solution is firstly diluted further 1:2 with 20 mM Tris, 2 M ammonium sulfate, 150 mM NaCl, pH 9.0, in order to achieve a final ammonium sulfate concentration of 1 M. This protein solution is then passed through a HiTrap butyl-S FF HIC column (GE Healthcare, Uppsala, Sweden) and, after binding of the target protein, eluted gradually with 20 mM Tris, 150 mM NaCl, pH 9.0.

As preparation for the second purification step, the HIC eluates are re-buffered in 20 mM Tris, 50 mM NaCl, pH 8.0, via a Sephadex-G25 column (GE Healthcare). As the second purification step, the eluates are applied to an anion exchange chromatography column (HiTrap Q HP, GE Healthcare), and the material passing through the column, which comprises the target protein, is collected.

In the final step, the AIEX output is subsequently purified via an SEC column (Superdex 75, GE Healthcare), so that the target protein is finally present in 20 mM Tris, 150 mM NaCl, pH 8.0.

Biochemical Analysis of MPV.5 (+6His ("6His" Disclosed as SEQ ID NO: 6)):

The purity of the proteins is checked by SDS-PAGE. The absence of insoluble protein aggregates is confirmed by UV-Vis spectroscopy. The identity of the fusion component-free MPV.5 is confirmed by determination of the molecular weight by means of mass spectroscopy (MALDI-TOF) and sequencing of the N-terminal amino acid sequence (sequence: A-D-L-G-Y-G-P-A-T (SEQ ID NO: 7)) (Table 6).

Analysis of MPV.5 by SEC/MALS/RI shows that the protein is exclusively in the form of the monomer (FIG. 13, Table 6). A comparable result is obtained with the fusion protein. The high tendency towards dimerisation which is observed in the case of variant MPV.4 is thus dependent on the presence of mutation d[P146, P155].

Evidence of the Reduced IgE Binding of MPV.5 (+6His ("6His" Disclosed as SEQ ID NO: 6)):

The investigation of the IgE binding ability is carried out using an EAST inhibition test with IgE antibodies of allergy sufferers which are employed in the form of a representative serum pool. MPV.5 exhibits IgE binding ability which is reduced to an equal extent both with and without fusion component. The IgE binding ability is somewhat higher than that of variant MPV.4, which may be due to better accessibility of IgE epitopes in the case of MPV.5, which is exclusively in monomeric form (FIG. 18).

The results of variant MPV.5 in the strip test using individual grass pollen allergy sufferer sera are depicted in FIG. 17. It is clear that the Phl p 5-specific IgE antibodies of all allergy sufferer sera bind variant MPV.5 to a greatly reduced extent.

Evidence of the Reduction of the Functional Allergeneity of MPV.5 (+6His ("6His" Disclosed as SEQ ID NO: 6)):

The functional action of MPV.5 in the crosslinking of membrane-bound IgE of the effector cells and activation thereof is investigated both with fusion proteins and with non-fusion proteins in vitro. MPV.5 exhibits greatly reduced activation of basophilic granulocytes of grass pollen allergy sufferers here compared with rPhl p 5a wt and thus highly functionally reduced allergeneity (FIG. 21).

EXAMPLE 8: HYPOALLERGENIC VARIANT RPHL P 5A D[P57, P58, P117, P146, P155, P180, P229] P211 L (MPV.6)

The preparation and immunological characterisation of variant MPV.6 is described below by way of example for hypoallergenic variants of group 5 allergens of the Poaceae with combinations of deletions of proline residues 57, 58, 117, 146, 155, 180 or 229 corresponding to the amino acid positions in Phl p 5.0109, in which proline residue 211 is mutated into any desired other amino acid. The recombinant unmodified allergen (rPhl p 5 wt+6His ("6His" disclosed as SEQ ID NO: 6)) is prepared and investigated analogously, and the hypoallergenic variants of the other group 5 allergens according to the invention of the true grasses and their wild-type proteins, in particular Lol p 5 and Poa p 5, can also be prepared and investigated analogously.

Construction by Genetic Engineering:

For the preparation of the DNA, a DNA fragment of MPV.2+6His ("6His" disclosed as SEQ ID NO: 6) is ligated into vector rPhl p 5a d[57, 58, 117, 180, 229] P211 L/pTMP (Allergopharma) present at this time. The correctness of the sequence is checked by DNA sequencing.

Expression:

The expression is carried out exclusively as fusion component-free protein in expression vector pTMP (Allergopharma) in *Escherichia coli* (strain BL21; Merck, Darmstadt). The recombinant proteins are deposited as inclusion bodies (IB).

Purification:

The IB solution of the denatured non-fusion protein is firstly diluted 1:50 with 20 mM Tris, 150 mM NaCl, pH 9.0, and kept at 4° overnight.

In a first purification step, the target protein is enriched by hydrophobic interaction chromatography (HIC).

The dilute protein solution is firstly diluted further 1:2 with 20 mM Tris, 2 M ammonium sulfate, 150 mM NaCl, pH 9.0, in order to achieve a final ammonium sulfate concentration of 1 M. This protein solution is then passed through a HiTrap butyl-S FF HIC column (GE Healthcare, Uppsala, Sweden) and, after binding of the target protein, eluted gradually with 20 mM Tris, 150 mM NaCl, pH 9.0.

As preparation for the second purification step, the HIC eluates are re-buffered in 20 mM Tris, 50 mM NaCl, pH 8.0, via a Sephadex G25 column (GE Healthcare). As the second purification step, the eluates are applied to an anion exchange chromatography column (HiTrap Q HP, GE Healthcare), and the material passing through the column, which comprises the target protein, is collected. In the final step, the AIEX output is subsequently purified via an SEC column (Superdex 75, GE Healthcare), so that the target protein is finally present in 20 mM Tris, 150 mM NaCl, pH 8.0.

Biochemical Analysis:

The purity of the proteins is checked by SDS-PAGE. The identity of the fusion component-free MPV.6 is confirmed by determination of the molecular weight by means of mass spectroscopy (MALDI-TOF) and sequencing of the N-terminal amino acid sequence (sequence: A-D-L-G-Y-G-P-A-T (SEQ ID NO: 7)) (Table 6).

The absence of insoluble protein aggregates is confirmed by UV-Vis spectroscopy. In the analysis of MPV.6 by means of SEC/MALS/RI, the purified proteins elute in two peaks. Peak 1 represents the monomeric form and peak 2 the dimeric form (FIG. 16; Table 6).

The dimerisation ability is, as also shown with reference to variants MPV.4 and MPV.5, attributable to the presence of mutation d[P146, 155].

Evidence of Reduced IgE Binding:

The investigation of the IgE binding is carried out using an EAST inhibition test with IgE antibodies of allergy sufferers which are employed in the form of a representative serum pool. The results depicted in FIG. 19 show that MPV.6 has greatly reduced IgE binding. The results in the strip test using individual grass pollen allergy sufferer sera are depicted in FIG. 17. It is clear that the Phl p 5-specific IgE antibodies of all allergy sufferer sera bind variant MPV.6 to a greatly reduced extent.

Evidence of the Reduction of Functional Allergeneity:

The functional action of MPV.6 in the crosslinking of membrane-bound IgE and the activation of basophilic granulocytes is greatly reduced compared with rPhl p 5a wt, as shown by the results with whole blood of two grass-pollen allergy sufferers (FIG. 22).

EXAMPLE 9: HYPOALLERGENIC VARIANT RPHL P 5A D[P57, P58, P117, P180, P229] P211L (MPV.7)

The preparation and immunological characterisation of variant MPV.7 is described below by way of example for hypoallergenic variants of group 5 allergens of the Poaceae with combinations of deletions of proline residues 57, 58, 117, 180 or 229 corresponding to the amino acid positions in Phl p 5a wild-type or Phl p 5.0109, in which proline residue 211 is mutated into any desired other amino acid. The recombinant unmodified allergen (rPhl p 5 wt+6His ("6His" disclosed as SEQ ID NO: 6)) is prepared and investigated analogously, and the hypoallergenic variants of the other group 5 allergens according to the invention of the true grasses and their wild-type proteins, in particular Lol p 5 and Poa p 5, can also be prepared and investigated analogously.

Construction by Genetic Engineering:

The DNA is prepared by preparation of a DNA fragment by means of specific oligonucleotides by PCR processes and then re-cloning into vector rPhl p 5a d[P57, P58, P117, P180, P211, P229]/pTMP (Allergopharma) already present at this time. The correctness of the sequence is checked by DNA sequencing.

Expression:

The expression is carried out as fusion component-free protein in expression vector pTMP (Allergopharma) in *Escherichia coli* (strain BL21; Merck, Darmstadt). The recombinant proteins are deposited as inclusion bodies (IB).

Test of Solubility:

The series testing in order to check the solubility properties of the recombinant protein in a non-denaturing environment shows high solubility of the protein in the slightly basic pH range (Table 5).

Purification:

The IB solution of the denatured non-fusion protein is firstly diluted 1:50 with 20 mM Tris, 150 mM NaCl, pH 9.0, and kept at 4° overnight. In a first purification step, the target protein is enriched by hydrophobic interaction chromatography (HIC). The dilute protein solution is firstly diluted further 1:2 with 20 mM Tris, 2 M ammonium sulfate, 150 mM NaCl, pH 9.0, in order to achieve a final ammonium sulfate concentration of 1 M. This protein solution is then passed through a HiTrap butyl-S FF HIC column (GE Healthcare, Uppsala, Sweden) and, after binding of the target protein, eluted gradually with 20 mM Tris, 150 mM NaCl, pH 9.0.

As preparation for the second purification step, the HIC eluates are re-buffered in 20 mM Tris, 50 mM NaCl, pH 8.0, via a Sephadex G25 column (GE Healthcare). As the second purification step, the eluates are applied to an anion exchange chromatography column (HiTrap Q HP, GE Healthcare), and the material passing through the column, which comprises the target protein, is collected. In the final step, the AIEX output is subsequently purified via an SEC column (Superdex 75, GE Healthcare), so that the target protein is finally present in 20 mM Tris, 150 mM NaCl, pH 8.0.

Biochemical Analysis:

The purity of the proteins is checked by SDS-PAGE. The identity of the fusion component-free MPV.7 is confirmed by determination of the molecular weight by means of mass spectroscopy (MALDI-TOF) and sequencing of the N-terminal amino acid sequence (sequence: A-D-L-G-Y-G-P-A-T (SEQ ID NO: 7)) (Table 6). The absence of insoluble protein aggregates is confirmed by UV-Vis spectroscopy. Analysis by SEC/MALS/RI shows that the eluted proteins are exclusively in the form of monomers (FIG. 14; Table 6). This is attributable to the absence of mutation d[P146, P155].

Evidence of Reduced IgE Binding:

The investigation of the IgE binding is carried out using an EAST inhibition test with IgE antibodies of allergy sufferers which are employed in the form of a representative serum pool. The results depicted in FIG. 19 show that MPV.7 has greatly reduced IgE binding. The results in the strip test using individual grass pollen allergy sufferer sera are depicted in FIG. 17. It is clear that the Phl p 5-specific IgE antibodies of all allergy sufferer sera bind variant MPV.7 to a greatly reduced extent.

Evidence of the Reduction of Functional Allergenicity:

The functional action of MPV.7 in the crosslinking of membrane-bound IgE and the activation of basophilic granulocytes of grass pollen allergy sufferers is greatly reduced compared with rPhl p 5a wt (FIG. 23).

T-Cell Reactivity of the Hypoallergenic Phl p 5a Variants:

In order to investigate the T-cell reactivity, oligoclonal T-cell lines of grass pollen allergy sufferers are established by conventional methods with stimulation with natural nPhl p 5a or rPhl p 5a wt molecules. In a proliferation test, the different T-cell lines were stimulated with the reference allergen rPhl p 5a wt and the modified recombinant allergen variants. The proliferation rate was determined by conventional methods by the incorporation of [3H]-thymidine.

The results of the proliferation tests of MPV.4 and MPV.7 with T-cell lines of 12 grass pollen allergy sufferers are depicted here by way of example for the modified allergen variants described.

The T-cell reactivity of variant MPV.4, which carries the most mutations of all molecules investigated, is not reduced, in spite of the modifications of the amino acid sequence compared with unmodified rPhl p 5a wt, which demonstrates the retention of crucial T-cell epitopes (Table 7).

Mutant MPV.7 contains the smallest number of modified amino acid positions of all multiproline mutants investigated. As expected, the molecule stimulates human T-lymphocytes comparably well to the unmodified allergen rPhl p 5a (Table 8).

TABLE 1

Solubility behaviour of MPV.1 + 6His ("6His" disclosed as SEQ ID NO: 6)

| d[P57, 58] | d[P85] | d[P117] | d[146, 155] | d[P180] | d[P211] | d[P211L] | d[P229] | d[P256] | K61E, E205K |
|---|---|---|---|---|---|---|---|---|---|
| x | x | x | x | x | x | | x | x | |

| Soln. | pH | NaCl | Buffer substance | Additive | OC[1] | $A_{280}/A_{330}$[2] | Evaluation[3] |
|---|---|---|---|---|---|---|---|
| 1 | 4.5 | 0.15 M | 0.02 M Na acetate | none | – | n.p. | – |
| 2 | 5.5 | 0.15 M | 0.02 M Na citrate | none | – | n.p. | – |
| 3 | 6.5 | 0.15 M | 0.02 M Ka phosph. | none | – | n.p. | – |
| 4 | 7.5 | 0.15 M | 0.02 M Na phosph. | none | – | n.p. | – |
| 5 | 8.0 | 0.15 M | 0.02 M Tris | none | – | n.p. | – |
| 6 | 9.0 | 0.15 M | 0.02 M Tris | none | – | n.p. | – |
| 7 | 8.0 | 0.075 M | 0.02 M Tris | 0.5 M L-arginine HCl; 0.005% (w/v) Tween 80 | + | 12.5 (–) | – |
| 8 | 8.0 | none | 0.02 M Tris | 0.005% (w/v) Tween 80 | + | 10.2 (–) | – |
| 9 | 8.0 | none | 0.02 M Tris | 0.5 M L-arginine HCl | – | n.p. | – |
| 10 | 7.5 | none | 0.02 M Na phosph. | 10% (w/v) glycerine | – | n.p. | – |

[1]The proteins isolated from inclusion bodies were firstly denatured using 6 M guanidinium hydrochloride, subsequently diluted 1:50 in a non-denaturing solution (soln. 1-10) and kept at 4° C. overnight. On the following day, an organoleptic check (OC) with respect to turbidity caused by visible macroaggregates or precipitates was carried out. (–) turbidity; (+) clear solution.
[2]UV/Vis spectral analysis for the detection of insoluble microaggregates in clear solutions by determination of the ratio of the absorption at 280 and 330 nm. Test of the batches after centrifugation. $A_{280}/A_{330} \leq 20$: precipitation (–); $A_{280}/A_{330} \leq 30$: precipitation tendency (o); $A_{280}/A_{330} > 30$: no precipitation (+). (n.p.) not performed.
[3]Evaluation of the solubility behaviour based on organoleptic and spectrophotometric analysis. (–) tending towards insoluble; (+) soluble.

TABLE 2

Solubility behaviour of MPV.2 + 6His ("6His" disclosed as SEQ ID NO: 6)

| d[P57, 58] x | d[P85] | d[P117] x | d[146, 155] x | d[P180] x | d[P211] x | P211L | d[P229] x | d[P256] | K61E, E205K |
|---|---|---|---|---|---|---|---|---|---|

| Soln. | pH | NaCl | Buffer substance | Additive | OC[1] | $A_{280}/A_{330}$[2] | Evaluation[3] |
|---|---|---|---|---|---|---|---|
| 1 | 4.5 | 0.15 M | 0.02 M Na acetate | none | − | n.p. | − |
| 2 | 5.5 | 0.15 M | 0.02 M Na citrate | none | − | n.p. | − |
| 3 | 6.5 | 0.15 M | 0.02 M Ka phosph. | none | − | n.p. | − |
| 4 | 7.5 | 0.15 M | 0.02 M Na phosph. | none | − | n.p. | − |
| 5 | 8.0 | 0.15 M | 0.02 M Tris | none | − | n.p. | − |
| 6 | 9.0 | 0.15 M | 0.02 M Tris | none | − | n.p. | − |
| 7 | 8.0 | 0.075 M | 0.02 M Tris | 0.5 M L-arginine HCl; 0.005% (w/v) Tween 80 | + | 11.5 (−) | − |
| 8 | 8.0 | none | 0.02 M Tris | 0.005% (w/v) Tween 80 | − | n.p. | − |
| 9 | 8.0 | none | 0.02 M Tris | 0.5 M L-arginine HCl | − | n.p. | − |
| 10 | 7.5 | none | 0.02 M Na phosph. | 10% (w/y) glycerine | − | n.p. | − |

[1]The proteins isolated from inclusion bodies were firstly denatured using 6 M guanidinium hydrochloride, subsequently diluted 1:50 in a non-denaturing solution (soln. 1-10) and kept at 4° C. overnight. On the following day, an organoleptic check (OC) with respect to turbidity caused by visible macroaggregates or precipitates was carried out. (−) turbidity; (+) clear solution.
[2]UV/Vis spectral analysis for the detection of insoluble microaggregates in clear solutions by determination of the ratio of the absorption at 280 and 330 nm. Test of the batches after centrifugation. $A_{280}/A_{330} \leq 20$: precipitation (−); $A_{280}/A_{330} \leq 30$: precipitation tendency (○); $A_{280}/A_{330} > 30$: no precipitation (+). (n.p.) not performed.
[3]Evaluation of the solubility behaviour based on organoleptic and spectrophotometric analysis. (−) tending towards insoluble; (+) soluble.

TABLE 3

Solubility behaviour of MPV.3 + 6His ("6His" disclosed as SEQ ID NO: 6)

| d[P57, 58] x | d[P85] | d[P117] | d[146, 155] | d[P180] | d[P211] x | P211L | d[P229] x | d[P256] | K61E, E205K x |
|---|---|---|---|---|---|---|---|---|---|

| Soln. | pH | NaCl | Buffer substance | Additive | OC[1] | $A_{280}/A_{330}$[2] | Evaluation[3] |
|---|---|---|---|---|---|---|---|
| 1 | 4.5 | 0.15 M | 0.02 M Na acetate | none | − | n.p. | − |
| 2 | 5.5 | 0.15 M | 0.02 M Na citrate | none | − | n.p. | − |
| 3 | 6.5 | 0.15 M | 0.02 M Ka phosph. | none | − | n.p. | − |
| 4 | 7.5 | 0.15 M | 0.02 M Na phosph. | none | − | n.p. | − |
| 5 | 8.0 | 0.15 M | 0.02 M Tris | none | + | 36.0 (+) | + |
| 6 | 9.0 | 0.15 M | 0.02 M Tris | none | + | 42.6 (+) | + |
| 7 | 8.0 | 0.075 M | 0.02 M Tris | 0.5 M L-arginine HCl; 0.005% (w/v) Tween 80 | + | 37.5 (−) | + |
| 8 | 8.0 | none | 0.02 M Tris | 0.005% (w/v) Tween 80 | + | 26.0 (○) | − |
| 9 | 8.0 | none | 0.02 M Tris | 0.5 M L-arginine HCl | − | n.p. | − |
| 10 | 7.5 | none | 0.02 M Na phosph. | 10% (w/y) glycerine | − | n.p. | − |

[1]The proteins isolated from inclusion bodies were firstly denatured using 6 M guanidinium hydrochloride, subsequently diluted 1:50 in a non-denaturing solution (soln. 1-10) and kept at 4° C. overnight. On the following day, an organoleptic check (OC) with respect to turbidity caused by visible macroaggregates or precipitates was carried out. (−) turbidity; (+) clear solution.
[2]UV/Vis spectral analysis for the detection of insoluble microaggregates in clear solutions by determination of the ratio of the absorption at 280 and 330 nm. Test of the batches after centrifugation. $A_{280}/A_{330} \leq 20$: precipitation (−); $A_{280}/A_{330} \leq 30$: precipitation tendency (○); $A_{280}/A_{330} > 30$: no precipitation (+). (n.p.) not performed.
[3]Evaluation of the solubility behaviour based on organoleptic and spectrophotometric analysis. (−) tending towards insoluble; (+) soluble.

TABLE 4

Solubility behaviour of MPV.4 + 6His ("6His" disclosed as SEQ ID NO: 6)

| d[P57, 58] x | d[P85] | d[P117] x | d[146, 155] x | d[P180] x | d[P211] x | P211L | d[P229] x | d[P256] | K61E, E205K x |
|---|---|---|---|---|---|---|---|---|---|

| Soln. | pH | NaCl | Buffer substance | Additive | OC[1] | $A_{280}/A_{330}$[2] | Evaluation[3] |
|---|---|---|---|---|---|---|---|
| 1 | 4.5 | 0.15 M | 0.02 M Na acetate | none | − | n.p. | − |
| 2 | 5.5 | 0.15 M | 0.02 M Na citrate | none | − | n.p. | − |
| 3 | 6.5 | 0.15 M | 0.02 M Ka phosph. | none | − | n.p. | − |
| 4 | 7.5 | 0.15 M | 0.02 M Na phosph. | none | + | 33.6 (+) | + |
| 5 | 8.0 | 0.15 M | 0.02 M Tris | none | + | 34.3 (+) | + |

TABLE 4-continued

Solubility behaviour of MPV.4 + 6His ("6His" disclosed as SEQ ID NO: 6)

| | | | | | | | |
|---|---|---|---|---|---|---|---|
| 6 | 9.0 | 0.15 M | 0.02 M Tris | none | + | 32.0 (+) | + |
| 7 | 8.0 | 0.075 M | 0.02 M Tris | 0.5 M L-arginine HCl; 0.005% (w/v) Tween 80 | + | 34.8 (−) | + |
| 8 | 8.0 | none | 0.02 M Tris | 0.005% (w/v) Tween 80 | + | 23.9 (○) | − |
| 9 | 8.0 | none | 0.02 M Tris | 0.5 M L-arginine HCl | − | n.p. | − |
| 10 | 7.5 | none | 0.02 M Na phosph. | 10% (w/y) glycerine | − | n.p. | − |

[1] The proteins isolated from inclusion bodies were firstly denatured using 6 M guanidinium hydrochloride, subsequently diluted 1:50 in a non-denaturing solution (soln. 1-10) and kept at 4° C. overnight. On the following day, an organoleptic check (OC) with respect to turbidity caused by visible macroaggregates or precipitates was carried out. (−) turbidity; (+) clear solution.
[2] UV/Vis spectral analysis for the detection of insoluble microaggregates in clear solutions by determination of the ratio of the absorption at 280 and 330 nm. Test of the batches after centrifugation. $A_{280}/A_{330} \leq 20$: precipitation (−); $A_{280}/A_{330} \leq 30$: precipitation tendency (○); $A_{280}/A_{330} \geq 30$: no precipitation (+). (n.p.) not performed.
[3] Evaluation of the solubility behaviour based on organoleptic and spectrophotometric analysis. (−) tending towards insoluble; (+) soluble.

TABLE 5

Solubility behaviour of MPV.7 d[P57, 58] x d[P85] x d[P117] d[146, 155] x d[P180] d[P211] P211L x d[P229] x d[P256] K61E, E205K

| Soln. | pH | NaCl | Buffer substance | Additive | OC[1] | $A_{280}/A_{330}$[2] | Evaluation[3] |
|---|---|---|---|---|---|---|---|
| 1 | 4.5 | 0.15 M | 0.02 M Na acetate | none | − | n.p. | − |
| 2 | 5.5 | 0.15 M | 0.02 M Na citrate | none | − | n.p. | − |
| 3 | 6.5 | 0.15 M | 0.02 M Ka phosph. | none | − | n.p. | − |
| 4 | 7.5 | 0.15 M | 0.02 M Na phosph. | none | − | n.p. | + |
| 5 | 8.0 | 0.15 M | 0.02 M Tris | none | + | 32.5 (+) | + |
| 6 | 9.0 | 0.15 M | 0.02 M Tris | none | + | 72.5 (+) | + |
| 7 | 8.0 | 0.075 M | 0.02 M Tris | 0.5 M L-arginine HCl; 0.005% (w/v) Tween 80 | + | 37.6 (+) | + |
| 8 | 8.0 | none | 0.02 M Tris | 0.005% (w/v) Tween 80 | − | n.p. | − |
| 9 | 8.0 | none | 0.02 M Tris | 0.5 M L-arginine HCl | + | 30.4 (+) | + |
| 10 | 7.5 | none | 0.02 M Na phosph. | 10% (w/y) glycerine | + | 43.0 (+) | + |

[1] The proteins isolated from inclusion bodies were firstly denatured using 6 M guanidinium hydrochloride, subsequently diluted 1:50 in a non-denaturing solution (soln. 1-10) and kept at 4° C. overnight. On the following day, an organoleptic check (OC) with respect to turbidity caused by visible macroaggregates or precipitates was carried out. (−) turbidity; (+) clear solution.
[2] UV/Vis spectral analysis for the detection of insoluble microaggregates in clear solutions by determination of the ratio of the absorption at 280 and 330 nm. Test of the batches after centrifugation. $A_{280}/A_{330} \leq 20$: precipitation (−); $A_{280}/A_{330} \leq 30$: precipitation tendency (○); $A_{280}/A_{330} > 30$: no precipitation (+). (n.p.) not performed.
[3] Evaluation of the solubility behaviour based on organoleptic and spectrophotometric analysis. (−) tending towards insoluble; (+) soluble.

TABLE 6

Results of the molecular weight analysis of MPV.4, MPV.5, MPV.6 and MPV.7 compared with rPhl p 5a wt

| Phl p 5a variant | $MW_{calc.}$ [kD][1] | SEC-MALS-RI[2] Peak | MW [kD] | Assessment |
|---|---|---|---|---|
| Wild type | 28.3 | 1 | 27.3 | Only monomers detectable |
| MPV.4 | 27.6 | 1 | 28.2-49.3* | Monomer and dimers detectable in mixed peak |
| MPV.5 | 27.8 | 1 | 27.2 | Only monomers detectable |
| MPV.6 | 27.6 | 1 | 53.0 | Dimer peak — Monomers and dimmers detectable |
| | | 2 | 29.8 | Monomer peak |
| MPV.7 | 27.8 | 1 | 27.2 | Only monomers detectable |

[1] Calculated molecular weight ($MW_{calc.}$) without starting methionine on the basis of the amino acid sequence (Software: DNA-Star, Lasergene, USA)
[2] Determination of the particle mass by SEC-MALS. The figure quoted is the average mass of the eluted protein particles in the peak window set with the exception of the measurement of MPV.4 (*), in which the scattering range of the masses in the peak as a whole is indicated.
For online determination of the protein concentration, the OptilabrEX refractive index detector (RI) (Wyatt, Santa Barbara, USA) was employed. The light scattering by the particles was determined using the MiniDAWN Treos multiangle detector (Wyatt). The particle mass was calculated using ASTRA 5.3.2.17 software (Wyatt) via Debeye formalism with an assumed refractive-index increment of 0.180 ml/g.
Column: Superdex 200 GL 10/300 (GE Healthcare, Uppsala, Sweden). The size exclusion ($t_0$) is at 20.45 min (corresponds to ~670 kD).
Eluent: 20 mM Tris 8.0, 150 mM NaCl

TABLE 7

Evidence of the T-cell reactivity of MPV.4

| | | Stimulation index[1] | | Reactivity of MPV.4 relative to |
|---|---|---|---|---|
| Donor[2] | T-cell line | rPhl p 5a wt | MPV.4 | rPhl p 5a wt[3] |
| 3 | 3.10 | 3.0 | 4.0 | 1.33 |
| 8 | 8.2 | 13 | 12.7 | 0.98 |
| 8 | 8.3 | 2.9 | 4.0 | 1.38 |
| 19 | 19.1 | 7.2 | 9.9 | 1.38 |
| 19 | 19.2 | 3.5 | 4.9 | 1.40 |
| 21 | 21.210 | 4.5 | 5.8 | 1.29 |
| 23 | 23.22 | 4.3 | 2.2 | 0.51 |
| 55 | 55.184 | 26.7 | 28.5 | 1.07 |
| 55 | 55.193 | 49.9 | 46.2 | 0.93 |
| 59 | 59.57 | 4.1 | 4.4 | 1.07 |
| 59 | 59.91 | 7.7 | 9.0 | 1.17 |
| 60 | 60.162 | 4.9 | 2.6 | 0.53 |
| 65 | 65.115 | 6.7 | 9.1 | 1.36 |
| 116 | 116.34 | 9.4 | 2.8 | 0.30 |
| 128 | 128.40 | 8.8 | 8.9 | 1.01 |
| 137 | 137.41 | 2.8 | 6.5 | 2.32 |

TABLE 7-continued

Evidence of the T-cell reactivity of MPV.4

| Donor[2] | T-cell line | Stimulation index[1] rPhl p 5a wt | MPV.4 | Reactivity of MPV.4 relative to rPhl p 5a wt[3] |
|---|---|---|---|---|
| 137 | 137.43 | 2.6 | 2.5 | 0.96 |
| | | | | 1.12 average |
| | | | | 0.45 SD |

[1]Stimulation index (SI), calculated from [³H] measurement values of the proliferation test. cpm measurement values of allergen-stimulated cell cultures/cpm measurement values of unstimulated cell cultures.
[2]Donor: clinically defined grass pollen allergy sufferer.
[3]Calculated using SI (MPV.4)/SI (rPhl p 5a wt).
SD: standard deviation.

TABLE 8

Evidence of the T-cell reactivity of MPV.7

| Donor[2] | T-cell line | Stimulation index[1] rPhl p 5a wt | MPV.7 | Reactivity of MPV.7 relative to rPhl p 5a wt[3] |
|---|---|---|---|---|
| 3 | 3.10 | 2.0 | 2.2 | 1.10 |
| 8 | 8.2 | 27.7 | 23.6 | 0.85 |
| 8 | 8.3 | 5.2 | 8.2 | 1.58 |
| 11 | 11.2 | 2.1 | 2.7 | 1.29 |
| 11 | 11.3 | 2.4 | 2.4 | 1.00 |
| 19 | 19.1 | 4.8 | 6.5 | 1.35 |
| 21 | 21.2 | 3.7 | 3.4 | 0.92 |
| 21 | 21.210 | 3.9 | 5.4 | 1.38 |
| 55 | 55.181 | 12.4 | 14.8 | 1.19 |
| 55 | 55.184 | 123.6 | 149.5 | 1.21 |
| 59 | 59.91 | 4.5 | 5.0 | 1.11 |
| 60 | 60.162 | 2.9 | 2.6 | 0.90 |
| 65 | 65.115 | 4.6 | 4.7 | 1.02 |
| 70 | 70.126 | 6.5 | 6.5 | 1.00 |
| 116 | 116.34 | 8.5 | 2.5 | 0.29 |
| 128 | 128.40 | 4.8 | 3.5 | 0.73 |
| | | | | 1.06 average |
| | | | | 0.30 SD |

[1]Stimulation index (SI), calculated from [³H] measurement values of the proliferation test. cpm measurement values of allergen-stimulated cell cultures/cpm measurement values of unstimulated cell cultures.
[2]Donor: clinically defined grass pollen allergy sufferer.
[3]Calculated using SI (MPV.7)/SI (rPhl p 5a wt).
SD: standard deviation.

The invention claimed is:

1. A hypoallergenic variant of a group 5 allergen Phl p 5 of the true grass family (Poaceae), wherein
   (a) the prolines which correspond in an alignment to the prolines in positions 57, 58, 117, 180, and 229 in the amino acid sequence of wild-type Phl p 5.0109 of SEQ ID NO:2 have been mutated by point mutations consisting of deletion of said prolines, and
   (b) the proline which corresponds in an alignment to the proline in position 211 in the amino acid sequence of wild-type Phl p 5.0109 of SEQ ID NO:2 has been mutated by substitution with a leucine residue.

2. A hypoallergenic compound comprising
   (a) a multimer of one or more hypoallergenic variants of claim 1, or
   (b) a constituent of a recombinant fusion protein of one or more hypoallergenic variants of claim 1, or multimers thereof.

3. A medicament comprising a hypoallergenic variant of claim 1 and a carrier.

4. A method to reduce the likelihood or symptoms of an allergic reaction, and/or for the therapeutic treatment of type 1 allergies triggered by group 5 allergens of the true grasses, comprising administering to a subject in need thereof, a hypoallergenic variant of claim 1.

* * * * *